(12) United States Patent
Jarrell et al.

(10) Patent No.: US 7,579,146 B2
(45) Date of Patent: *Aug. 25, 2009

(54) NUCLEIC ACID CLONING

(75) Inventors: Kevin A. Jarrell, Lincoln, MA (US);
Vincent W. Coljee, Gentofte (DK);
William Donahue, Quincy, MA (US);
Svetlana Mikheeva, Allston, MA (US)

(73) Assignee: Trustees of Boston University, Boston, MA (US)

( * ) Notice: Subject to any disclaimer, the term of this patent is extended or adjusted under 35 U.S.C. 154(b) by 72 days.

This patent is subject to a terminal disclaimer.

(21) Appl. No.: 09/897,712

(22) Filed: Jun. 29, 2001

(65) Prior Publication Data

US 2005/0191623 A1  Sep. 1, 2005

Related U.S. Application Data

(63) Continuation-in-part of application No. PCT/US00/00189, filed on Jan. 5, 2000, and a continuation-in-part of application No. 09/225,990, filed on Jan. 5, 1999, now Pat. No. 6,358,712.

(60) Provisional application No. 60/114,909, filed on Jan. 5, 1999.

(51) Int. Cl.
*C12Q 1/68* (2006.01)
*C07H 21/04* (2006.01)
*C12N 15/00* (2006.01)

(52) U.S. Cl. .................. 435/6; 435/320.1; 435/254.2; 536/24.3; 536/24.33; 536/24.5

(58) Field of Classification Search .................. 435/6, 435/320.1, 254.2, 254, 2; 536/24.3, 24.33, 536/24.5
See application file for complete search history.

(56) References Cited

U.S. PATENT DOCUMENTS

| | | | |
|---|---|---|---|
| 4,237,224 A | 12/1980 | Cohen et al. | |
| 4,661,450 A | 4/1987 | Kempe et al. | 435/172.3 |
| 4,683,195 A | 7/1987 | Mullis et al. | |
| 4,683,202 A | 7/1987 | Mullis | |
| 4,740,470 A | 4/1988 | Cohen et al. | |
| 4,935,357 A | 6/1990 | Szybalski | 435/91 |
| 4,987,071 A | 1/1991 | Cech et al. | 435/91 |
| 5,093,246 A | 3/1992 | Cech et al. | 435/91 |
| 5,098,837 A | 3/1992 | Beckmann et al. | |
| 5,116,742 A | 5/1992 | Cech et al. | 435/91 |
| 5,180,818 A | 1/1993 | Cech et al. | 536/23.1 |
| 5,252,474 A | 10/1993 | Gewain et al. | |
| 5,270,185 A | 12/1993 | Margolskee | 435/91.41 |
| 5,333,675 A | 8/1994 | Mullis et al. | |
| 5,432,263 A | 7/1995 | Haviv et al. | 530/345 |
| 5,487,993 A | 1/1996 | Herrnstadt et al. | 435/172.3 |
| 5,498,531 A | 3/1996 | Jarrell | 435/91.31 |
| 5,523,221 A | 6/1996 | Weiner | 435/172.3 |
| 5,573,913 A | 11/1996 | Rosemeyer et al. | 435/6 |
| 5,580,723 A | 12/1996 | Wells et al. | 435/6 |
| 5,595,985 A | 1/1997 | Miki et al. | 435/172.3 |
| 5,603,793 A | 2/1997 | Yoshida et al. | |
| 5,605,793 A | 2/1997 | Stemmer | 435/6 |
| 5,641,673 A | 6/1997 | Hazeloff et al. | 435/235 |
| 5,643,766 A | 7/1997 | Scheele et al. | 435/912 |
| 5,652,116 A | 7/1997 | Grandi et al. | 435/69.1 |
| 5,660,985 A | 8/1997 | Pieken et al. | 435/6 |
| 5,667,969 A | 9/1997 | Sullenger et al. | 435/6 |
| 5,672,491 A * | 9/1997 | Khosla et al. | 435/148 |
| 5,688,670 A | 11/1997 | Szotak et al. | 435/91.21 |
| 5,698,421 A | 12/1997 | Lambowitz et al. | 435/91.1 |
| 5,712,146 A | 1/1998 | Khosla et al. | 435/252.35 |
| 5,716,849 A | 2/1998 | Ligon et al. | 435/419 |
| 5,723,323 A | 3/1998 | Kauffman et al. | 435/172.3 |
| 5,763,239 A | 6/1998 | Short et al. | |
| 5,780,272 A | 7/1998 | Jarrell | 435/91.31 |
| 5,792,607 A | 8/1998 | Backman et al. | 435/6 |
| 5,795,738 A | 8/1998 | Grandi et al. | 435/69.1 |
| 5,804,418 A | 9/1998 | Lambowitz et al. | 435/69.1 |
| 5,811,238 A | 9/1998 | Stemmer et al. | 435/6 |
| 5,814,476 A | 9/1998 | Kauffman et al. | 435/69.1 |
| 5,817,483 A | 10/1998 | Kauffman et al. | 435/69.1 |
| 5,824,513 A | 10/1998 | Katz et al. | 435/76 |

(Continued)

FOREIGN PATENT DOCUMENTS

EP  0550693  7/1993

(Continued)

OTHER PUBLICATIONS

Suzuki et al. Journal of Bacteriology, 1983, vol. 155(2), p. 747-754.*

(Continued)

*Primary Examiner*—Kenneth R. Horlick
*Assistant Examiner*—Joyce Tung
(74) *Attorney, Agent, or Firm*—Margo H. Furman, JD; Choate, Hall & Stewart, LLP

(57) ABSTRACT

The present invention provides an improved system for linking nucleic acids to one another. In particular, the present invention provides techniques for producing DNA product molecules that may be easily and directly ligated to recipient molecules. The product molecules need not be cleaved with restriction enzymes in order to undergo such ligation. In preferred embodiments of the invention, the DNA product molecules are produced through iterative DNA synthesis reactions, so that the product molecules are amplified products. The invention further provides methods for directed ligation of product molecules (i.e., for selective ligation of certain molecules within a collection of molecules), and also for methods of exon shuffling, in which multiple different product molecules are produced in a single ligation reaction. Preferred embodiments of the invention involve ligation of product molecules encoding functional protein domains, particularly domains naturally found in conserved gene families. The inventive DNA manipulation system is readily integrated with other nucleic acid manipulation systems, such as ribozyme-mediated systems, and also is susceptible to automation.

47 Claims, 47 Drawing Sheets

U.S. PATENT DOCUMENTS

| | | | |
|---|---|---|---|
| 5,824,514 A | 10/1998 | Kauffman et al. | 435/91.1 |
| 5,824,774 A | 10/1998 | Chappell et al. | 530/350 |
| 5,827,657 A | 10/1998 | Herrnstadt et al. | |
| 5,827,704 A | 10/1998 | Cease et al. | 435/172.3 |
| 5,830,721 A | 11/1998 | Stemmer et al. | 435/172.1 |
| 5,834,250 A | 11/1998 | Wells et al. | 435/7.1 |
| 5,834,252 A | 11/1998 | Stemmer et al. | |
| 5,837,458 A | 11/1998 | Minshull et al. | |
| 5,837,855 A | 11/1998 | Chowrira et al. | |
| 5,843,718 A | 12/1998 | Khosla et al. | 435/69.1 |
| 5,856,144 A | 1/1999 | Mierendorf | 435/6 |
| 5,869,254 A | 2/1999 | Sullenger et al. | 435/6 |
| 5,869,634 A | 2/1999 | Lambowitz et al. | 536/23.1 |
| 5,928,906 A * | 7/1999 | Koster et al. | 435/91.2 |
| 5,935,788 A | 8/1999 | Burmer | 435/6 |
| 5,939,250 A | 8/1999 | Short | |
| 5,958,672 A | 9/1999 | Short | |
| 5,965,408 A | 10/1999 | Short | |
| 5,976,862 A | 11/1999 | Kauffman et al. | 435/252.3 |
| 6,001,574 A | 12/1999 | Short et al. | |
| 6,001,608 A | 12/1999 | Lambowitz et al. | |
| 6,013,478 A | 1/2000 | Wells et al. | 435/69.1 |
| 6,027,894 A | 2/2000 | Sapolsky et al. | 435/6 |
| 6,027,895 A | 2/2000 | Lambowitz et al. | |
| 6,030,779 A | 2/2000 | Short | |
| 6,054,267 A | 4/2000 | Short | |
| 6,057,103 A | 5/2000 | Short | |
| 6,083,702 A | 7/2000 | Mitchell et al. | |
| 6,117,679 A | 9/2000 | Stemmer | |
| 6,132,970 A | 10/2000 | Stemmer | |
| 6,165,793 A | 12/2000 | Stemmer | |
| 6,168,919 B1 | 1/2001 | Short | |
| 6,171,820 B1 | 1/2001 | Short | 435/69.1 |
| 6,180,406 B1 | 1/2001 | Stemmer | 435/440 |
| 6,277,632 B1 | 8/2001 | Harney | 435/320.1 |
| 6,297,007 B1 | 10/2001 | Waters et al. | 435/6 |
| 6,358,712 B1 | 3/2002 | Jarrell et al. | |
| 6,495,318 B2 | 12/2002 | Harney | 435/6 |
| 6,537,776 B1 | 3/2003 | Short | 435/69.1 |
| 6,579,678 B1 | 6/2003 | Patten et al. | 435/6 |
| 6,605,449 B1 | 8/2003 | Short | 435/69.1 |
| 6,607,889 B1 | 8/2003 | Couli et al. | |
| 6,613,514 B2 | 9/2003 | Patten et al. | 435/6 |
| 6,939,689 B2 | 9/2005 | Short et al. | 435/69.1 |
| 6,946,296 B2 | 9/2005 | Patten et al. | 435/440 |
| 6,972,183 B1 | 12/2005 | Lafferty et al. | 435/7.4 |
| 6,979,733 B2 | 12/2005 | Zhao et al. | 536/23.2 |
| 6,995,017 B1 | 2/2006 | Stemmer | 435/440 |
| 7,018,793 B1 | 3/2006 | Short | 435/6 |
| 7,024,312 B1 | 4/2006 | Selifonov et al. | 702/19 |
| 7,078,035 B2 | 7/2006 | Short et al. | |
| 7,078,504 B2 | 7/2006 | Short et al. | |
| 7,105,297 B2 | 9/2006 | Minshull et al. | |
| 7,148,054 B2 | 12/2006 | Del Cardayre et al. | |
| 7,232,672 B2 | 6/2007 | Weiner et al. | 435/189 |
| 7,232,677 B2 | 6/2007 | Short et al. | 435/196 |
| 7,314,613 B2 | 1/2008 | Patten et al. | |
| 7,318,918 B2 | 1/2008 | Patten et al. | |
| 7,439,021 B2 | 10/2008 | Jarrell et al. | |
| 2005/0129059 A1 | 6/2005 | Jiang et al. | |
| 2005/0186622 A1 | 8/2005 | Stemmer et al. | |
| 2005/0191623 A1 | 9/2005 | Jarrell et al. | |
| 2005/0191688 A1 | 9/2005 | Selifonov et al. | |
| 2005/0266465 A1 | 12/2005 | Williams et al. | |
| 2006/0008844 A1 | 1/2006 | Stemmer et al. | |
| 2006/0045888 A1 | 3/2006 | Punnonen et al. | |
| 2006/0047611 A1 | 3/2006 | Selifonov et al. | |
| 2006/0051795 A1 | 3/2006 | Crameri et al. | |
| 2006/0084091 A1 | 4/2006 | Patten et al. | |
| 2006/0166225 A1 | 7/2006 | Patten et al. | |
| 2006/0177831 A1 | 8/2006 | Stemmer et al. | |
| 2006/0205003 A1 | 9/2006 | Gustafsson et al. | |
| 2006/0223143 A1 | 10/2006 | Patten et al. | |
| 2006/0234299 A1 | 10/2006 | Stemmer et al. | |
| 2006/0257890 A1 | 11/2006 | Minshull et al. | |
| 2006/0259995 A1 | 11/2006 | Cayouette et al. | |
| 2006/0275804 A1 | 12/2006 | Short et al. | |
| 2006/0286603 A1 | 12/2006 | Kolkman et al. | |
| 2007/0020235 A1 | 1/2007 | Patten et al. | |
| 2007/0020734 A1 | 1/2007 | Patten et al. | |
| 2007/0025966 A1 | 2/2007 | Patten et al. | |
| 2007/0026446 A1 | 2/2007 | del Cardayre et al. | |
| 2007/0031878 A1 | 2/2007 | Patten et al. | |
| 2007/0031943 A1 | 2/2007 | Jarrell | |
| 2007/0048775 A1 | 3/2007 | Cardayre et al. | |
| 2007/0054313 A1 | 3/2007 | Crameri et al. | |
| 2007/0056053 A1 | 3/2007 | Gray et al. | |
| 2007/0065407 A1 | 3/2007 | Patten et al. | |
| 2007/0065838 A1 | 3/2007 | Crameri et al. | |
| 2007/0087373 A1 | 4/2007 | Punnonen et al. | |
| 2007/0087374 A1 | 4/2007 | Punnonen et al. | |
| 2007/0092887 A1 | 4/2007 | Stemmer et al. | |
| 2007/0274950 A1 | 11/2007 | Patten et al. | |
| 2007/0292954 A1 | 12/2007 | Elledge | |
| 2008/0031853 A1 | 2/2008 | Patten et al. | |
| 2008/0032378 A1 | 2/2008 | Callen et al. | |
| 2008/0047037 A1 | 2/2008 | Callen et al. | |
| 2008/0076710 A1 | 3/2008 | Patten et al. | |

FOREIGN PATENT DOCUMENTS

| | | |
|---|---|---|
| EP | 0 625 572 | 11/1994 |
| EP | 0625572 | 11/1994 |
| EP | 0738779 | 10/1996 |
| EP | 0 773 294 A2 | 5/1997 |
| EP | 0773294 A2 | 5/1997 |
| EP | 0 773 294 A3 | 9/1997 |
| EP | 0773294 A3 | 9/1997 |
| EP | 0911396 | 4/1999 |
| EP | 0934999 | 8/1999 |
| EP | 1 002 860 | 5/2000 |
| EP | 1002860 | 5/2000 |
| EP | 0791655 | 10/2000 |
| EP | 0791656 | 10/2000 |
| EP | 1094108 | 4/2001 |
| EP | 01528067 | 5/2005 |
| EP | 01555316 | 7/2005 |
| EP | 1565 205 | 8/2005 |
| EP | 1576 108 | 9/2005 |
| EP | 1201 768 | 12/2005 |
| EP | 01108058 | 2/2006 |
| EP | 01690868 A1 | 8/2006 |
| EP | 01696025 A2 | 8/2006 |
| EP | 01696025 A3 | 9/2006 |
| EP | 01707641 A2 | 10/2006 |
| EP | 0839185 B1 | 11/2006 |
| EP | 01717322 A2 | 11/2006 |
| EP | 01707641 A3 | 12/2006 |
| EP | 01717322 | 1/2007 |
| EP | 01888633 | 2/2008 |
| JP | 2005/245453 | 9/2005 |
| JP | 2007244399 | 9/2007 |
| JP | 2007252382 | 10/2007 |
| WO | WO 86/05803 | 10/1986 |
| WO | WO-86/05803 | 10/1986 |
| WO | WO 89/05358 | 6/1989 |
| WO | WO 91/02077 | 2/1991 |
| WO | WO-92/06189 | 4/1992 |
| WO | WO-92/14819 | 9/1992 |
| WO | WO 94/16736 | 8/1994 |
| WO | WO 95/07347 | 3/1995 |
| WO | WO 95/07351 | 3/1995 |
| WO | WO 95/08548 | 3/1995 |
| WO | WO 95/13379 | 5/1995 |

| | | |
|---|---|---|
| WO | WO 95/22625 | 8/1995 |
| WO | WO-97/08185 | 3/1997 |
| WO | WO-97/10362 | 3/1997 |
| WO | WO 97/20078 | 6/1997 |
| WO | WO-97/28282 | 8/1997 |
| WO | WO 97/35966 | 10/1997 |
| WO | WO 98/01546 | 1/1998 |
| WO | WO-98/13485 | 4/1998 |
| WO | WO 98/13487 | 4/1998 |
| WO | WO-98/23756 | 6/1998 |
| WO | WO 98/27203 | 6/1998 |
| WO | WO 98/27230 | 6/1998 |
| WO | WO 98/31837 | 7/1998 |
| WO | WO 98/36097 | 8/1998 |
| WO | WO 98/38337 | 9/1998 |
| WO | WO-98/40519 | 9/1998 |
| WO | WO 98/49315 | 11/1998 |
| WO | WO 98/51695 | 11/1998 |
| WO | WO 98/53097 | 11/1998 |
| WO | WO 98/54353 | 12/1998 |
| WO | WO 98/56943 | 12/1998 |
| WO | WO 99/02669 | 1/1999 |
| WO | WO-99/23236 | 5/1999 |
| WO | WO 99/36546 | 7/1999 |
| WO | WO-99/41369 | 8/1999 |
| WO | WO-99/43854 | 9/1999 |
| WO | WO-99/51766 | 10/1999 |
| WO | WO-99/55857 | 11/1999 |
| WO | WO-99/65927 | 12/1999 |
| WO | WO-00/09727 | 2/2000 |
| WO | WO-00/12680 | 3/2000 |
| WO | WO 00/12687 | 3/2000 |
| WO | WO-00/18906 | 4/2000 |
| WO | WO-00/36088 | 6/2000 |
| WO | WO 00/40704 | 7/2000 |
| WO | WO-00/40715 | 7/2000 |
| WO | WO 00/42195 | 7/2000 |
| WO | WO-00/42559 | 7/2000 |
| WO | WO-00/42561 | 7/2000 |
| WO | WO-00/52155 | 9/2000 |
| WO | WO-00/77262 | 12/2000 |
| WO | WO 01/18253 | 3/2001 |
| WO | WO 01/32845 | 5/2001 |
| WO | WO 01/38489 | 5/2001 |
| WO | WO 01/59126 | 8/2001 |
| WO | WO 02/24736 | 3/2002 |
| WO | WO-03/030623 | 4/2003 |
| WO | EP01644394 | 3/2005 |
| WO | WO 2005/026184 | 3/2005 |
| WO | WO-05/093099 | 10/2005 |
| WO | WO-05/093101 | 10/2005 |
| WO | WO-05/097992 | 10/2005 |
| WO | WO 2005/093099 | 10/2005 |
| WO | WO 2005/093101 | 10/2005 |
| WO | WO 2005/097992 | 10/2005 |
| WO | 2005113592 | 12/2005 |
| WO | WO-05/113592 | 12/2005 |
| WO | WO-05/118853 | 12/2005 |
| WO | WO 2005/113592 | 12/2005 |
| WO | WO 2005/118853 | 12/2005 |
| WO | WO 2006/009888 | 1/2006 |
| WO | WO 2006/028684 | 3/2006 |
| WO | WO-2006/028684 A2 | 3/2006 |
| WO | WO-2006/083276 A2 | 8/2006 |
| WO | WO-2006/096527 A2 | 9/2006 |
| WO | WO-2006/099207 A2 | 9/2006 |
| WO | WO-2006/101584 A2 | 9/2006 |
| WO | WO-2006/127040 A2 | 11/2006 |
| WO | WO-2007044083 | 4/2007 |
| WO | WO-2007/124065 | 11/2007 |

OTHER PUBLICATIONS

Abelian, A., et al., "Targeting The A Site RNA Of The Escherichia Coli Ribosomal 30 S Subunit By 2'-0-Methyl Oligoribonucleotides: A Quantitative Equilibrium Dialysis Binding Assay And Differential Effects Of Aminoglycoside Antibiotics.", *Biochem. Journal* 383(2): 201-208, 2004.

Kierzek, E., et al., "The Influence Of Locked Nucleic Acid Residues On The Thermodynamic Properties Of 2'-O-Methyl RNA/RNA Heteroduplexes.", *Nucleic Acid Research* 33(16): 5082-5093, 2005.

Sandbrink, J., et al., "Investigation Of Potential RNA Bulge Stabilizing Elements.", *J Mol Recognit* 18(4): 318-326, 2005.

Suzuki, Y., et al., "A Novel High-Throughput (HTP) Cloning Strategy For Site-Directed Designed Chimeragenesis And Mutation Using The Gateway Cloning System.", *Nucleic Acid Research* 33(12): e109 (1-6), 2005.

Wright, A., et al., "Diverse Plasmid DNA Vectors By Directed Molecular Evolution Of Cytomegalovirus Promoters.", *Human Gene Therapy* 16(7): 881-892, 2005.

Gade, et al., "Incorporation of Nonbase Residues into Synthetic Oligonucleotides and Their Use in the PCR", *GATA*, 10(2): 61-65, 1993.

Newton, et al., "The Production of PCR Products with 5' Single-Stranded Tails Using Primers that Incorporate Novel Phosphoramidite Intermediates", *Nucleic Acids Research*, 21(5): 1155-1162, 1993.

Gade, et al., "Incorporation Of Nonbase Residues Into Synthetic Oligonucleotides And Their Use In The PCR." *GATA* 10(2): 61-65, 1993.

Stump, et al., "The Use Of Modified Primers To Eliminate Cycle Sequencing Artifacts" *Nucleic Acids Research* 27(23): 4642-4648, 1999.

Agabian et al., Trans Splicing of Nuclear Pre-m-RNA's, *Cell*, 61:1157-1160, 1990.

Aharonowitz, et al., "Penicillin and Cephalosporin Biosynthetic Genes: Structure, Organization, Regulation, and Evolution", *Annu. Rev. Microbiol*, 46: 461-495, 1992.

Ahsen, et al., "Footprinting the Sites of Interaction of Antibiotics with Catalytic Group I Intron RNA", *Science*, 260: 1500-1503, 1993.

Akiyama, et al., "P-Coumaroyltriacetic Acid Synthase, A New Homologue of Chalcone Synthase, from Hydrangea Macrophylla Var, Thunbergii", *Eur. J. Biochem.* 263: 834-839, 1999.

Aparicio, et al., "The Biosynthetic Gene Cluster for the 26-Membered Ring Polyene Macrolide Pimaricin", The Journal of Biological Chemistry, *Eur. J. Biochem.* 274(15): 10133-10139, 1999.

Aparicio, et al., "Limited Proteolysis and Active-Site Studies of the First Multienzyme Component of the Erythromycin-Producing Polyketide Synthase", *The Journal of Biological Chemistry*, 269(11): 8524-8528, 1994.

Aparicio, et al., "Organization of the Biosynthetic Gene Cluster for Rapamycin in Streptomyces Hygroscopicus: Analysis of the Enzymatic Domains in the Modular Polyketide Synthase", *Gene*, 169: 9-16, 1996.

Aslanidis, et al., Ligation-Independent Cloning of PCR Products (LIC-PCR), *Nucleic Acids Research*, 18(20): 6069-6074.

Augustin et al., "Reverse Self-Splicing of Group II Intron RNAs in Vitro" *Nature*, 343:383-386, 1990.

Baldwin, T., "Reverse Self-Splicing of Group II Intron RNAs in Vitro" *Nature*, 343: 383-386, 1990.

Beaudry et al., "Directed Evolution of an RNA Enzyme" *Science*, 257:635-641, 1992.

Bedford, et al., "Expression of a Functional Fungal Polyketide Synthase in the Bacterium Streptomyces Coelicolor A3(2)", *Journal of Bacteriology*, 177(15): 4544-4548, 1995.

Bedford, et al., "A Functional Chimeric Modular Polyketide Synthase Generated Via Domain Replacement", *Chemistry & Biology*, 3(10): 1996.

Been et al., "One Binding Site Determines Sequence Specificity of Therahymena Pre-rRNA Self-Splicing, Trans-Splicing, and RNA Enzyme Activity", *Cell*, 47:207-216, 1986.

Bevitt, et al., "6-Deoxyerythronolide-B Synthase 2 From Saccharopolyspora Erythraea, Cloning of the Structural Gene, Sequence Analysis and Inferred Domain Structure of the Multifunctional Enzyme".
Bevitt, et al., "Mutagenesis of the Dehydratase Active Site in the Erythromycin-Producing Polyketide Synthase", *Biochemical Society Transaction*, 1992.
Bibb, et al., "Analysis of the Nucleotide Sequence of the Streptomyces Glaucescens Teml Genes Provides Key Information about the Enzymology of Polyketide Antibiotic Biosynthesis", *The EMBO Journal*, 8(9): 2727-2736, 1989.
Bonen et al., "Trans-Splicing of Pre-mRNA in Plants, Animals and Protists" the *FASEB J.*, 7:40-46, 1993.
Blumenthal et al., "Cis and Trans mRNA Splicing in C. Elegans", *TIG*, 4(11): 305-308, 1988.
Blumenthal, T. Mammalian Cells Can Trans-Splice. But Do They? *BioEssays*, 15(5): 347-348, 1993.
Blumenthal, "Trans-Splicing and Polycistronic Transcription in Caenorhabditis Elegans" *TIG*, 11(4): 132-136, 1995.
Brown, et al., "Aspergillus Has Distinct Fatty Acid Synthases for Primary and Secondary Metabolism", *Proc. Natl. Acid. Sci, USA*, 93: 14873-14877, 1996.
Bryk et al., "Spontaneous Shuffling of Domains Between Introns of Phage T4", *Nature*, 346: 394-396, 1990.
Burke, et al., "Sequences and Classification of Group I and Group II Introns", *Methods in Enzym.* 180: 533-545, 1989.
Buckler et al., "Exon Amplification; A Strategy to Isolate Mammalian Genes Based on RNA Splicing" *Proc. Natl. Acad. Sci.*, 88:4005-4009, 1991.
Butler, et al., "Impact of Thioesterase Activity on Tylosin Biosynthesis in Streptomyces Fradiae", *Chemistry & Biology*, 6(5): 287-292.
Caffrey, et al., "Identification of DEBS 1, DEBS 2 and DEBS3, the Multienzyme Polypeptides of the Erythromycin-Producing Polyketide Synthase from Saccharopolyspora Erythraea", 304: 2, 3, 225-228, 1992.
Campbell et al., "Alternative Approaches for the Application of Ribozymes as Gene Therapies for Retroviral Infections" *Adv. In Pharm.* 33: 143-178, 1995.
Cane, et al., "Highly Efficient Incorporation of Polyketide Chain Elongation Intermediates into 6-Deoxyerthronolide B in an Engineered Streptomyces Host", The Journal of Antibiotics 48(7): 647-651.
Cane, et al., "Harnessing the Biosynthetic Code: Combinations, Permutations, and Mutations", *Science*, 282: 1998.
Cane, et al., "Polyketide Biosynthesis: Molecular Recognition of Genetic Programming?", *Science*, 263: 1994.
Capel, et al., "Circular Transcripts of the Testis-Determining Gene Sry in Adult Mouse Testis", *Cell.* 73: 1019-1030, 1993.
Carreras, et al., "The Chemistry and Biology of Fatty Acid, Polyketide, and Nonribosomal Peptide Biosynthesis", Topics in Current.
Carter, et al., "Improved Oligonucleotide Site-Directed Mutagenesis Using M13 Vectors" Nucl. Acids Res.13: 4431-4443, 1985.
Cech et al., "Self-Splicing of Group I Introns" *Annu. Rev. Biochem.* 59:543-568, 1990.
Chapdelaine et al., "The Wheat Mitochondrial Gene for Subunit I of the NADH Dehydrogenase Complex: A Trans-Splicing Model for this Gene-in-Pieces", *Cell*, 65:465-472, 1991.
Chuat et al., "Can Ribosymes Be Used to Regulate Procaryote Gene Expression?" *Biochem. And Biophys. Res. Commun.*, 162(3): 1025-1029, 1989.
Conklin et al., "Multiple Trans-Splicing Events are Required to Produce a Mature Nad 1 Transcript in a Plant Mitochondrion" Genetics and Devel., Cornell Univ. Ithica, NY 14853, USA, May 1-9, 1991.
Conrad et al., "Conversion of a Trans-Spliced C. Elegans Gene into a Conventional Gene by Introduction of a Splice Donor Site", *EMBO J.*, 12(3): 1249-1255, 1993.
Conrad et al., "Insertion of Part of an Intron into the 5' Untranslated Region of a Caenorhabditis Elegans Gene Converts it Into a Trans-Spliced Gene", *Molec. And Cellul. Biol.*, 11(4): 1921-1926, 1991.

Conti, et al., "Crystal Structure of Firefly Luciferase Throws Light on a Superfamily of Adenylate-Forming Enzymes", *Research Article*, 4(3): 1996.
Conti, et al., "Structural Basis for the Activation of Phenylalanine in the Non-Ribosomal Biosynthesis of Gramididin S", *The EMBO Journal*, 16(14): 4174-4183, 1997.
Cortes, et al., "Repositioning of a Domain in a Modular Polyketide Synthase to Promote Specific Chain Cleavage", *Science*, 268: 1487-1489, 1995.
Cosmina, et al., "Sequence and Analysis of the Genetic Locus Responsible for Surfactin Synthesis in Bacillus Subtilis", *Molecular Microbiology*, 8(5): 821-831, 1993.
Cotton et al., "Ribozyme Mediated Destruction of RNA in Vivo", *EMBO J.*, 8(12): 3861-3866, 1989.
Couto et al., "A Trans-Acting Suppressor Restores Splicing of a Yeast Intron with a Branch Point Mutation" *Genes & Devel., Cold Spring Harbor Lab.*, 445-455, 1987.
Cripe, et al., "Structure of the Gene for Human Coagulation Factor V" *Biochemistry*, 31: 3777-3785, 1992.
Crosby, et al., "Polyketide Synthase Acyl Carrier Proteins from Streptomyces: Expression in Escherichia Coli, Purification and Partial Characterization", *Biochimica et Biophysica Acta* 1251: 32-42, 1995.
Curcio, et al., "Retrohoming: cDNA-Mediated Mobility Minireview of Group II Introns Requires a Catalytic RNA", *Cell*, 84: 9-12, 1996.
Da'Dara et al., "A Novel Trans-Spliced mRNA from Onchocerca Volvulus Encodes a Functional S-Adenosylmethionine Decarboxylase" *Biochem. J.*, 320:519-530, 1996.
Dairi, et al., "Development of Self-Cloning System for Actinomadura Verrucosospora and Identification of Polyketide Synthase Genes Essential for Production of the Angucyclic Antibiotic Pradimicin", Appl. Environ. Microbiol. 65(6): 2703-2709.
Davis et al., "RNA Trans-Splicing in Flatworms" *J. Biol. Chem.*, 270(37): 21813-21819, 1995.
Davis, et al., "The Production of Surfaction in Batch Culture by Bacillus Subtilis ATCC 21332 is Strongly Influenced by the Conditions of Nitrogen Metabolism" *Enzyme and Microbial Technology*, 25: 322-329, 1999.
Decker, et al., "Identification of Streptomyces Olivaceus Tü 2353 Genes Involved in the Production of the Polyketide Elloramycin", *Gene*, 166: 121-126, 1995.
De Giorgi et al., "A Silent Trans-Splicing Signal in the Cuticlin-Encoding Gene of the Plant-Parasitic Nematode Meloidogyne Artiellia.", *Gene*, 170(2): 261-265, 1996.
De Vries et al., "Artificial Exon Shuffling between Tissue-Type Plasminogen Activator (t-PA) and Urokinase (u-PA): A Comparative Study on the Fibrinolytic Properties of t-PA/U-PA Hybrid Proteins" *Biochemistry*, 27:2565-2572, 1988.
Dib-Hajj, "Domain 5 Interacts with Domain 6 and Influences the Second Transesterification Reaction of Group II Intron Self-Splicing", *Nucl. Acids Res.*, 21(8): 1797-1804, 1993.
Dieckmann, et al., "The Adenylation Domain of Tyrocidine Synthetase 1 Structural and Functional Role of the Interdomain Linker Region and the (S/T) GT (T/S) GXPKG Core Sequence", *Eur. J. Biochem.* 247: 1074-1082, 1997.
Dieckmann, et al., "Probing the Domain Structure and Ligand-Induced Conformational Changes by Limited Proteolysis of Tyrocidine Synthetase 1", *J. Mol. Biol.*, 288: 129-140, 1999.
Donadio, et al., "Biosynthesis of the Eryrthromycin Macrolactone and a Rational Approach for Producing Hybrid Macrolides", *Gene*, 115: 97-103, 1992.
Donadio, et al., "Organization of the Enzymatic Domains in the Multifunctional Polyketide Synthase Involved in Erythromycin Formation in Saccharopolyspora Erythraea", *Gene*, 111: 51-60, 1992.
Donadio, et al., "Modular Organization of Genes Required for Complex Polyketide Biosynthesis", *Science*, 252: 675-679, 1991.
Dorit et al., "How Big is the Universe of Exons?" *Sci.* 250: 1377-1382, 1990.
Doudna et al., "RNA Structure not Sequence, Determines the 5'Splice-Site Specificity of a Group I Intron" *Proceedings of the National Academy of Sciences*, 86:7402-7406, 1989.
Eul et al., "Experimental Evidence for RNA Trans-Splicing in Mammalian Cells", *EMBO J.* 14(13): 3226-3235, 1995.

Eul et al., "Trans-Splicing and Alternative-Tandem-Cis-Splicing: Two Ways by Which Mammalian Cells Generate a Truncated SV40 T-Antigen" *Nucl. Acids. Res.* 24(9): 1653-1661, 1996.

Fedorov et al., "Analysis of Nonuniformity in Intorn Phase Distribution" *Nucl. Acid Res.*, 20(10): 2553-2557, 1992.

Franzen et al., Kinetic Analysis of the 5'Splice Junction Hydrolysis of a Group II Intron Promoted by Domain 5' Nucleic Acid Research, 21(3): 627-634, 1993.

Fu, et al., "Engineered Biosynthesis of Novel Polyketides: Stereochemical Course of Two Reactions Catalyzed by a Polyketide Synthase", *Biochemistry*, 33: 9321-9326, 1994.

Fujii, et al., "Heterologous Expression and Product Identification of Colletotrichum Lagenarium Polyketide Synthase Encoded by the PKS1 Gene Involved in Melanin Biosynthesis", *Biosci. Biotechnol. Biochem.* 63(8): 1445-1452, 1999.

Fuma, et al., "Nucleotide Sequence of 5' Portion of srfA That Contains the Region Required for Competence Establishment in Bacillus Subtilus", *Nucleic Acids Research*, 21(1): 93-97, 1993.

Gaisser, et al., "Sugaring the Pill by Design", *Nature Biotechnology*, 16: 19-20, 1998.

Garriga et al., "Mechanism of Recognition of the 5'Splice Site in Self-Splicing Group I Introns", *Nature*, 322:3, 86-89, 1986.

Ghetti et al., "In Vitro Trans-Splicing in Saccharomyces Cerevisiae", Proc. Natl. Acad. Sci. USA., 92: 11461-11464, 1995.

Gocht, et al., "Analysis of Core Sequences in the D-Phe Activating Domain of the Multifunctional Peptide Synthetase TycA by Site-Directed Mutagenesis", *Journal of Bacteriology*, 176(9): 2654-2662, 1994.

Gokhale, et al., "Mechanism and Specificity of the Terminal Thioesterase Domain from the Erythromycin Polyketide Synthase", *Chemistry & Biology*, 6(2): 117-125.

Goldschmidt-Clermont et al., "A Small Cholorplast RNA May Be Required for Trans-Splicing in Chlamydomonas Reinhardtii", *Cell*, 65:135-143, 1991.

Goldschmiti-Clermont et al., Trans-Splicing Mutants of Chlamydomonas Reinhardtii, Mol. Gen. Genet., 223:417-425, 1990.

Graham, et al., "Identification of Mycobacterium Tuberculosis RNAs Synthesized in Respone to Phagocytosis by Human Macrophages by Selective Capture of Transcribed Sequences (SCOTS)", *Proc. Natl. Acad. Sci, USA*, 96: 11554-11559, 1999.

Grangemard, et al., "Lichenysins G, a Novel Family of Lipopeptide Biosurfactants from Bacillus Licheniformis IM 1307: Production, Isolation and Structural Evaluation by NMR and Mass Spectrometry", The Journal of Antibiotics, 52(4): 363-373, 1999.

Haese, et al., "Bacterial Expression of Catalytically Active Fragments of the Multifunctional Enzyme Enniatin Synthetase", *Academic Press Limited*, 116-122, 1994.

Hall et al., "Exon Shuffling by Recombination Between Self-Splicing Introns of Bacteriophage T4" *Nature*, 340:574-576, 1989.

Haydock, et al., "Divergent Sequence Motifs with the Substrate Specificity of (methyl) Malonyl-CoA: Acyl Carrier Protein Transacylase Domains in Modular Polyketide Synthases", *FEBS Letters*, 374: 246-248, 1995.

Hazell, et al., "□-Tocopherol Does Not Inhibit Hypochlorite-Induced Oxidation of Apolipoprotein B-100 of Low-Density Lipoprotein", *FEBS Letters*, 414: 541-544, 1997.

Henderickson, et al., "Lovastatin Biosynthesis in Aspergillus Terreus: Characterization of Blocked Mutants, Enzyme Activities and a Multifunctional Polyketide Synthase Gene" *Chemistry & Biology*, 6(7): 1999.

Herrin et al., "Trans-Splicing of Transcripts for the Chloroplast psaA1 Gene", *J. Biol. Chem.*, 263(29): 14601-14604, 1988.

Herzog et al., "Overlapping Gene Structure of the Human Neuropeptide Y Receptor Subtypes Y1 and Y5 Suggests Coordinate Transcriptional Regulation" *Genomics*, 41(3): 315-319, 1997.

Hetzer et al., "Trans-Activation of Group II Intron Splicing by Nuclear U5 snRNA" Nature, 386(6623): 417-420, 1997.

Holländer, et al., "Splicing of the Mitochondrial Group II Intron rII: Conserved Intron-Exon Interactions Diminish Splicing Efficiency" *Curr. Genet*, 33(2): 117-123, 1998.

Holzbaur, et al., "Molecular Basis of Celmer's Rules: The Role of Two Ketoreductase Domains in the Control of Chirality by Erythromycin Modular Polyketide Synthase", *Chemistry & Biology*, 6(4): 1999.

Hong, et al., "Cloning and Heterologous Expression of the Entire Gene Clusters for PD 116740 From Streptomyces Strain WP 4669 and Tetrangulol and Tetrangomycin from Streptomyces Rimosus NRRL 3016", Journal of Bacteriology, 179(2): 470-476, 1997.

Hopwood, et al., "Genes for Polyketide Secondary Metabolic Pathways in Microorganisms and Plants", 89-112.

Hu, et al., "Repeated Polyketide Synthase Modules Involved in the Biosynthesis of a Heptaene Macrolide by Streptomyces sp. FR-008", *Molecular Microbiology*, 14(1): 163-172, 1994.

Hutchinson, C., "Microbial Polyketide Synthases: More and More Prolific", *Proc. Natl. Acad. Sci, USA*, 96: 3336-3338, 1999.

Hutchinson, C., "Drug Synthesis by Genetically Engineered Microorganisms", *Bio/Technology*, 12: 375-380.

Ikeda, et al., "Organization of the Biosynthetic Gene Cluster for the Polyketide Anthelminitic Macrolide Avermectin in Streptomyces Avermitilis", *Proc. Natl. Acad. Sco, USA*, 96: 9509-9514, 1999.

Jacobson, et al., "Precursor-Directed Biosynthesis of 12-Ethyl Erythromycin", *Bioorganic & Medicinal Chemistry*, 6: 1171-1177, 1998.

Jacquier et al., "Efficient Trans-Splicing of a Yeast Mitochondrial RNA Group II Intron Implicates a Strong 5'Exon-Intron Interaction" *Sci*., 234:1099-1104, 1986.

Jacquier et al., "Multiple Exon-Binding Sites in Class II Self-Splicing Introns" *Cell*, 50:17-29,1987.

Jarrell et al., "Group II Intron Domain 5 Facilitates a Trans-Splicing Reaction" *Molecular and Cell. Biol.*, 8(6): 2361-2366, 1988.

Jarrell et al., "Group II Intron Self-Splicing" *J. Biol. Chem.* 263(7): 3432-3439, 1988.

Jarrell, "Iverse Splicing of a Group II Intron", *Proc. Natl. Acad. Sci. USA*, 90: 9624-8627, 1993.

Jones et al., "Evaluating and Enhancing Ribozyme Reaction Efficiency in Mammalian Cells", *Nature Biotech*, 15:902-905, 1997.

Jones et al., "Tagging Ribozyme Reaction Sites to Follow Trans-Splicing in Mammalian Cells", *Nat. Med.*, 2(6): 643-648, 1996.

Jordan, et al., "The Biosynthesis of Tetraketides: Enzymololgy, Mechanism and Molecular Programming", *Biochemical Society Transactions*, 21: 222-228, 1993.

Kao, et al., "Engineered Biosynthesis of a Complete Macrolactone in a Heterologous Host", *Science*, 265: 509-512, 1994.

Kao, et al., "Evidence for Two Catalytically Independent Clusters of Active Sites in a Functional Modular Polyketide Synthase", *Biochemistry*, 35: 12363-12368, 1996.

Katz, et al., "Polyketide Synthesis: Prospects for Hybrid Antibiotics", *Annu. Rev. Microbiol.*, 47: 875-912, 1993.

Kealey, et al., "Production of a Polyketide Natural Product in Nonpolyketide Producing Prokaryotic and Eukaryotic Hosts" *Proc. Natl. Acad. Sci. USA*, 95: 505-509, 1998.

Kennedy, et al., "Nurturing Nature: Engineering New Antiobiotics", *Nature Biotechnology*, 17: 538-39, Jun. 1999.

Khosla, et al., "Genetic Construction and Functional Analysis of Hybrid Polyketide Synthases Containing Heterologous Acyl Carrier Proteins", *Journal of Bacteriology*, 175(8):2197-2204, 1993.

Khosla, et al., "Generation of Polyketide Libraries via Combinatorial Biosynthesis", *Focus*, 14: 335-41, 1996.

Khosla, et al., "Targeted Gene Replacements in a Streptomyces Polyketide Synthase Gene Cluster: Role for the Acyl Carrier Protein", *Molecular Microbiology*, 6(21): 3237-49, 1992.

Kim et al., "Pre-mRNA splicing within an assembled yeast spliceosome requires an RNA-dependent ATPase and ATP hydrolysis" *Proc. Natl. Acad. Sci.*, 90:888-92, Feb. 1993.

Kleinkauf, et al., "A Nonribosomal System of Peptide Biosynthesis" *Eur. J. Biochem.*, 236:335-51, 1996.

Kleinkauf, et al., "Linking Peptide and Polyketide Biosynthesis", *The Journal of Antiobiotics* 48:7, 563-67.

Knoop et al., "A Tripartite Group II Intron in Mitochondria of an Angiosperm Plant" *Mol. Gen Genet.*, 255(3): 269-276, 1996.

Knoop et al., "Promiscuous Mitochondrial Group II Intron Sequences in Plant Nuclear Genomes" *J. Mol Evol.*, 39(2): 144-150, 1994.

Knoop et al., "Trans Splicing Integrates an Exon of 22 Nucleotides into the nad5 mRNA in Higher Plant Mitochondria" *EMBO J.*, 10(11): 3483-3493, 1991.

Koch et al., "Group II Introns Delected for Multiple Substructures Retain Self-Splicing Activity" *Molec. And Cell Biol.*, 12(5): 1950-1958, 1992.

Kohchi et al., "A Nicked Group II Intron and Trans-Splicing in Liverwort, Marchantia Polymorpha, Chloroplasts" *Nucleic Acids Res.*, 16(21): 10025-10036, 1988.

Koller et al., "Evidence for In Vivo Trans Splicing of Pre-mRNAs in Tobacco Chloroplasts" *Cell.*, 48(1): 111-119, 1987.

Konarska et al., "Trans Splicing of mRNA Precursors In Vitro" *Cell*, 42: 165-171, 1985.

Kracht, et al., "Antiviral and Hemolytic Activities of Surfactin Isoforms and their Methyl Ester Derivatives", *The Journal of Antibiotics*, 52(7): 613-19, Jul. 1999.

Kuhstos, et al., "Production of a Novel Polyketide through the Construction of a Hybrid Polyketide Synthase", *Gene*, 183: 231-236, 1996.

Lan et al., "Ribozyme-Mediated Repair of Sickle☐-Globin mRNAs in Erythrocyte Precursors" *Sci.*, 280(5369):1593-96, Jun. 5, 1998.

Lan et al., "Ribozyme-Mediated Repair of Sickle—Globin mRNAs in Erthrocyte Precursors" *Sci.*, 280(5369): 1593-1596, 1998.

Langer-Safer et al., "Replacement of Finger and Growth Factor Domains of Tissue Plasminogen Activator with Plasminogen Kringle 1" J. Biolog. Chem., 266(6): 3715-3723, 1991.

Lau, et al., "Dissecting the Role of Acyltransferase Domains of Modular Polyketide Synthases in the Choice and Stereochemical Fate of Extender Units", *Biochemistry*, 1643-51, 1999.

Leadlay, et al., "The Erythromycin-Producing Polyketide Synthase", *Biochemical Society Transactions*, 21: 218-22, 1993.

Lee et al., "Conservation of Gene Organization and Trans-Splicing in the Glyceraldehyde—3-Phosphate Dehydrogenase-Encoding Genes of Caenorhabditis Briggsae" Gene, 121(2): 227-235, 1992.

Leenders, et al., "Rapid Typing of Bacillus Subtilis Strains by Their Secondary Metabolites Using Matrix-Assisted Laser Desorption/Ionization Mass Spectrometry of Intacts Cells", *Rapid Communications in Mass Spectrometry*, 13: 943-949, 1999.

Liempt, et al., "Principles of the Molecular Construction of Multienzyme Templates for Peptide Biosynthesis in Integrated Reaction Sequences", *Biomed. Biochim. Acta*, 50: 256-59, 1991.

Lin, et al., "General Approach for the Development of High-Perfomance Liquid Chromatography Methods for Biosurfactant Analysis and Purification", *Journal of Chromatography A*, 825: 149-59, 1998.

Lücke et al., "Spliced leader RNA of trypanosomes: in vivo mutational analysis reveals extensive and distinct requirements for *trans* splicing and cap4 formation" *EMBO J.*, 15(16): 4380-91, 1996.

Luo, et al., "Eryrthromycin Biosynthesis: Exploiting the Catalytic Versatility of the Modular Polyketide Synthase", *Bioorganic & Medicinal Chemistry*, 4(7): 995-99, 1996.

MacNeil, et al., "Complex Organization of the Streptomyces Avermitilis Genes Encoding the Avermectin Polyketide Synthase", *Gene*, 115, 119-125, (1992).

Malek, et al., "Evolution of trans-splicing plant mitochondrial introns in pre-Permian times", *Proc. Natl. Acad. Sci. USA.*, 94(2):553-58, Jan. 21, 1997.

Mann, John, "Rules for the Manipulation of Polyketides", *Nature*, 375: 1995.

Marahiel, et al., "Multidomain Enzymes Involved in Peptide Synthesis", *Federation of European Biochemical Societies*, 307(1): 40-43, Jul. 1992.

Maroney et al., "Intramolecular base pairing between the nematode spliced leader and its 5' splice site is not essential for *trans*-splicing in vitro", *EMBO J.*, 10(12):3869-75, Dec. 1991.

Marsden, et al., "Stereospecific Acyl Transfers on the Erythromycin-Producing Polyketide Synthase", *Science*, 263, 378-80, 1994.

Metzenberg, et al., "Human and Fungal 3' Splice Sites are Used by Trypanosoma Brucei for Trans Splicing", *Molcular and Biochemical Parasitology*, 83: 11-23, 1996.

Michel et al., "Comparative and functional anatomy of group II catalytic introns: a review" *Gene*, 82:5-30, 1989.

Mikheeva, et al., "Use of Engineered Ribozymes to Catalyze Chimeric Gene Assembly" *Proc. Natl. Acad. Sci. USA*, 93:7486-90, Jul. 1996.

Miller et al., "*trans* splicing in *Leishmania enriettii* and identification of ribonucleoprotein complexes containing the spliced leader and U2 equivalent RNAs" *Mol Cell Biol.*, 8(6): 2597-2603, Jun. 1988.

Mofid, et al., "Cystallization and Preliminary Crystallographic Studies of Sfp: a Phosphopanthetheinyl Transferase of Modular Peptide Synthetases", *Acta Cryst*.D55: 1098-1100, 1999.

Mohr, et al., "Integration of a Group I Intron into a Ribosomal RNA Sequence Promoted by a Tyrosyl tRNA Synthetase", *Nature*, 354: 164-167, 1991.

Moore, et al., "Site-Specific Modification of Pre-mRNA: The 2'-Hydroxyl Groups at the Splice Sites" *Science*, 256: 992-97, May 15, 1992.

Mootz, et al., "The Tyrocidine Biosynthesis Operon of Bacillus Brevis: Complete Nucleotide Sequence and Biochemical Characterization of Functional Internal Adenylation Domains", *Journal of Bacteriology*, 179(21): 6843-50.

Mootz, et al., "Design and Application of Multimodular Peptide Synthetases", *Current Opinion in Biotechnology*, 10: 341-348, 1999.

Mörl et al., "New Reactions Catalyzed by a Group II Intron Ribozyme with RNA and DNA Substrates", *Cell*, 70, 803-810, Sep. 1992.

Mörl et al., "Integration of Group II Intron b11 into a Foreign RNA by Reversal of the Self-Slicing Reaction In Vitro" *Cell*, 60:629-36, Feb. 23, 1990.

Mörl, et al., "New Reactions Catalyzed by Group II Intron Ribozyme with RNA and DNA Substrates", *Cell*, 70: 803-810, 1992.

Mueller et al., "Group II Intron RNA Catalysis of Progressive Nucleotide Insertion: A Model for RNA Editing" *Sci.*, 261:1035-37, Aug. 20, 1993.

Murphy et al., "Identification of a Novel Y Branch Structure as an Intermediate in Trypanosome mRNA Processing: Evidence for *Trans* Splicing" *Cell*, 47(4):517-525, Nov. 21, 1986.

Nielsen, et al., "Viscosinamide, a New Cyclic Depsipeptide With Surfactant and Antifungal Properties Produced by Pseudomonas Fluorescens DR54", *Journal of Applied Microbiology*, 86: 80-90, 1999.

Ny et al., "The structure of the human tissue-type plasonogen activator gene: Gorrelation of intron and exon structures to functional and structural domains" *Proc. Natl. Acad. Sci.*, 81: 5355-59, Sep. 1984.

Ohno, et al., "Production of a Lipopeptide Antibiotic, Surfactin, by Recombinant Bacillus Subtilis in Solid State Fermentation", *Biotechnology and Bioengineering*, 47: 209-14, 1995.

Olano, et al., "Analysis of a Streptomyces Antibioticus Chromosomal Region Involved in Oleandomycin Biosynthesis, which encodes two glycosyltransferases responsible for glycosylation of the macrolactone ring", *Mol. Gen. Genet.*, 259: 299-08; 1998.

Oliynyk, et al., "A Hybrid Modular Polyketide Synthase Obtained by Domain Swapping", *Chemistry & Biology*, 3(10): 833-39, 1996.

Pasman, et al., "Exon Circularization in Mammalian Nuclear Extracts", *Cambridge University Press*, 2: 603, 10, 1996.

Patel, et al., "Cis-Trans-Splicing and RNA Editing are Required for the Expression of nad2 in Wheat Mitochondria", *Mol. Gen. Genet.* 258: 503-511, 1998.

Patthy et al., "Intron-dependent evolution: preferred types of exons and introns" *FEBS Letters*, 214(1):1-7, Apr. 1987.

Peebles et al., "Group II Intron Selt-splicing: Development of Alternative Reaction Conditions and Identification of a Predicted Intermediate" *Cold Spring Harbor Symp. on Quantitative Bio.*, LII:223-32, 1987.

Peebles et al., "Mutation of the Conserved First Nucleotide of a Group II Intron from Yeast Mitochondrial DNA Reduces the Rate But Allows Accurate Splicing" *J. of Biol. Chem.* 268(16):11929-38, Jun. 5, 1993.

Pereia de Souza et al., "A *trans*-splicing model for the expression of the tripartite *nad*5 gene in wheat and maize mitochondria" *Plant Cell*, 3(12):1363-78, Dec. 1991.

Pestov, et al., "Recombinant Polyketide Synthesis in Streptomyces: Engineering of Improved Host Strains", *Bio Techniques* 26: 106-10, Jan. 1999.

Peypoux, et al., "Recent Trends in the Biochemistry of Surfactin", 554-563.

Peypoux, et al., "[Ala4], Surfactin, A Novel Isoform From Bacillus Subtilis Studied by Mass and NMR Spectroscopies", *Eur. J. Biochem.*, 224, 89-96, 1994.

Phylactou et al., "Ribozyme-Mediated Trans Splicing of a Trinucleotide Repeat", *Nat. Genet.*, 18(4): 378-381, 1998.

Pieper, et al., "Arrangement of Catalytic Sites in the Multifunctional Enzyme Enniatin Synthetase", *Eur. J. Biochem.*, 230: 119-26, 1995.

Pieper, et al., "Erythromycin Biosynthesis: Kinetic Studies on a Fully Active Modular Polyketide Synthase Using Natural and Unnatural Substrates", *Biochemistry*, 35: 2054-60, 1996.

Pieper, et al., "Cell-Free Synthesis of Polyketides by Recombinant Erythromycin Polyketide Synthases", *Nature*, 378: 263-66, 1995.

Puttaraju et al., "Group I permuted intron-exon (PIE) sequences self-splice to produce circular exons" *Nucleic Acids Res.*, 20(20):5357-64, 1992.

Roberts, et al., "6-Deoxyerythronolide B Synthase 3 From Saccharopolyspora Erythrea: Over-Expression in Escherichia Coli, Purification and Characterisation", Biochemical Society Transactions, 1992.

Roberts, et al., "Heterologous Expression in Escherichia Coli of an Intact Multienzyme Component of the Erythromycin-Producing Polyketide Synthase", *Eur. J. Biochem*. 214:305-11, 1993.

Rodriguez, et al., "A Cytochrome P450-Like Gene Possibly Involved in Oleandomycin Biosynthesis by Streptomyces Antibiotics", *FEMS Microbiology Letters*, 127: 117-120, 1995.

Ruan, et al., "A Second Type-I PKS Gene Cluster Isolated from Streptomyces Hygroscopicus ATCC 29253, a Rapamycin-Producing Strain", *Gene*, 203: 1-9, 1997.

Saito, et al., "Entire Nucleotide Sequence for Bacillus Brevis Nagano Grs2 Gene Encoding Gramicidin S Synthetase 2: a Multifunctional Peptide Synthetase[1]", *J. Biochem.*, 116: 357-67, 1994.

Saldanha et al., "Group I and group II introns" *FASEB J.*, 7:15-24, Jan. 1993.

Salvo, et al., "Deletion-Tolerance and *Trans*-Splicing of the Bacteriophage T4 *td* Intron Analysis of the P6-L6a Region", *J. Mol. Biol*. 211: 537-49, 1990.

Sargueil et al., "A Shortened Form of the *Tetrahymena thermophila* Group I Intron Can Catalyze the Complete Splicing Reaction *in trans*" *J. Mol. Biol.*, vol. 233(4):629-43, Oct. 20, 1993.

Sarver et al., "Ribozyme trans-splicing and RNA tagging: Following the messenger" *Nat Med.*, 2(6):641-42, Jun. 1996.

Schmeizer et al., "Self-Splicing of Group II Introns In Vitro: Mapping of the Branch Point and Mutation Inhibition of Lariat Formation" *Cell*, 46:557-65, Aug. 15, 1986.

Schröder, et al., "Plant Polyketide Synthases: A Chalcone Synthase-Type Enzyme Which Performs a Condensation Reaction with Methylmalonyl-CoA in the Biosynthesis of C-Methylated Chalcones", *Biochemistry*, 37: 8417-25, 1998.

Schroeder, et al., "Splice-Site Selection and Decoding: Are They Related?" *Science*, 260: 1443-1444.

Schupp, et al., "A Sorangium Cellulosum (Myxobacterium) Gene Cluster for the Biosynthesis of the Macrolide Antibiotic Soraphen A: Cloning, Characterization, and Homology to Polyketide Synthase Genes From Actinomycetes" *Journal of Bacteriology*, 177(13): 3673-79, 1995.

Schwecke, et al., "The Biosynthetic Gene Cluster for the Polyketide Immunosuppressant Rapamycin", *Proc. Natl. Acad. Sci, USA*, 92 7839-43, Aug. 1995.

Seidel et al., "Exons as Microgenes?" *Science*, 257:1489-90, Sep. 11, 1992.

Sharp et al., "On the Origin of RNA Splicing and Introns" *Cell*, 42:397-400, Sep. 1985.

Sharp et al., "Trans Splicing: Variation on the Familiar Theme?" *Cell*, 50:147-48, Jul. 17, 1987.

Shen, et al., "Enzymatic Synthesis of a Bacterial Polyketide from Acetyl and Malonyl Coenzyme A", *Science*, 262: 1535-40, 1993.

Shen, et al., "Ectopic Expression of the Minimal WhiE Polyketide Synthase Generates a Library of Aromatic Polyketides of Diverse Sizes and Shapes" *Proc. Natl.Acad. Sci. USA*, 96: 3622-27, Mar. 1999.

Sherman, et al., "Functional Replacement of Genes for Individual Polyketide Synthase Components in Streptomyces Coelicolar A3(2) by Heterologous Genes from a Different Polyketide Pathway", *Journal of Bacteriology*, 174:19, 6184-90, 1992.

Solnick et al., "Trans Splicing of mRNA Precursors" *Cell*, 42:157-64, Aug. 1985.

Stachelhaus, et al., "Modular Structure of Genes Encoding Multifunctional Peptide synthetases Required for Non-Ribosomal Peptide Synthesis", *FEMS Microbiology Letters*, 125: 3-14, 1995.

Stassi, et al., "Ethyl-Substituted Erythromycin Derivatives Produced by Directed Metabolic Engineering", *Proc. Natl., Acad. Sci. USA.*, 95: 7305-09, Jun. 1998.

Steitz et al., "Splicing Takes a Holiday" *Sci.*, 257:888-89, Aug. 14, 1992.

Sturm et al., "Efficient *trans*-splicing of Mutated Spliced Leader Exons in *Leishmania tarentolae*" *J. Biol. Chem.*, 273(30):18689-92, Jul. 24, 1998.

Suchy et al., "Restoration of the Self-splicing Activity of a Defective Group II Intron by a Small Trans-acting RNA" *Institut für Genetik Mikrobiologie der Universität München, pp. 179-187, Academic Press Limited* 1991.

Sullenger et al., "Ribozymes-mediated repair of defective mRNA by targeted *trans*-splicing" *Nature*, 371, Oct. 13, 1995.

Sullenger et al., "Tethering Ribozymes to a Retroviral Packaging Signal for Destruction of Viral RNA" *Sci.*, 262:1566-69, Dec. 3, 1993.

Sullenger, et al., "Colocalizing Ribozymes with Substrate RNSs to Increase Their Efficacy as Gene Inhibitors", *Applice Biochem. and Biotech:*, 54: 57-61, 1995.

Summers, et al., "Malonyl-Coenzyme A:Acyl Carrier Protein Acyltransferase of Strepotomyces Glaucescens: A Possible Link Between Fatty Acid and Polyketide Biosynthesis", *Biochemistry*, 34(29): 9389-9402.

Sutton, et al., "Trypanosome Trans-Splicing Utilizes 2'-5' Branches and a Corresponding Debranching Activity", *The EMBO Journal*, 7:1431-37, 1988.

Szostak, et al., "Enzymatic Activity of the Conserved core of a Group I Self-Splicing Intron", *Nature*, 322:3, 83-86, Jul. 1986.

Tang, et al., "Characterization of the Enzymatic Domains in the Modular Polyketide Synthase Involved in Rifamycin B Biosynthesis by Amycolatopsis Mediterranei", *Gene*, 216: 255-65, 1998.

Tasiouka et al., "A modified group I intron can function as both a ribozyme and a 5' exon in a *trans*-exon ligation reaction" *Gene*, 144:1-7, 1994.

Thompson, et al., Identification and Sequence Analysis of the Genes Encoding a Polyketide Synthase Required for Pyoluteorin Biosynthesis in Pseudomonas Fluorescens Pf-5, *Gene*, 204: 17-24, 1997.

Tschudi et al., "Destruction of U2, U4, or U6 Small Nuclear RNA Blocks *Trans* Splicing in Trypanosome Cells" *Cell*, 61:459-66, May 4, 1990.

Turgay, et al., "Four Homologous Domains in the Primary Structure of GrsB are related to Domains in a Superfamily of Adenylate-Forming Enzymes", *Molecular Microbiology*, 6(4): 529-46, 1992.

Turmel et al., "The *trans*-spliced intron 1 in the *psa*A gene of the *Chlamydomonas* chloroplast: a comparative analysis" *Curr Genet.*, 27:270-9, 1995.

Ullu et al., "Permeable trypanosome cells as a model system for transcription and trans-splicing" *Nucleic Acids Res.*, 18(11):3319-26, 1990.

Vater, et al., "The Modular Organization of Multifunctional Peptide Synthetases", *Journal of Protein Chemistry*,16(5): 557-64, 1997.

Wallasch et al., "Structural requirements for section of 5'- and 3' splice sites of group II introns" *Nucleic Acids Res.*, 19(12):3307-14, 1991.

Wang et al., "Movement of the Guide Sequece During RNA Catalysis by a Group I Ribozyme" *Science*, 260:504-8, Apr. 23, 1993.

Watakabe et al., "The role of exon sequences in splice site selection" *Genes & Devel., Cold Spring Harbor Lab. Press*, 7:407-18, 1993.

Watanabe, et al., "Demonstration of the Catalytic Roles and Evidence For The Physical Association of Type I Fatty Acid Synthases and A Polyketide Synthase in the Biosynthesis of Aflatoxin $B_1$" *Chemistry and Biology*, 3, 463-69, Jun. 1996.

Weissman, et al., "The Molecular Basis of Celmer's Rules: The Stereochemistry of the Condensation Step in Chain Extension on the Erythromycin Polyketide Synthase", *Biochemistry*, 36: 13849-55, 1997.

Weissman, et al., "Origin of Starter Units for Erythromycin Biosynthesis", *Biochemistry*, 37: 11012-17, 1998.

Weinreb, et al., "Stoichiometry and Specificity of In Vitro Phosphopantetheinylation and Aminoacylation of the Valine-Activating Module of Surfactin Synthetase", *Biochemistry*, 37:1575-84, 1998.

Weissman, et al., "Evaluating Precursor-Directed Biosynthesis Towards Novel Erythromycins through In Vitro Studies on a Bimodular Polyketide Synthase", *Chemistry & Biology*, 5(12): 743-54.

Winter et al., "The mechanism of group I self-splicing: an internal guide sequence can be provided in *trans*" *EMBO J*., 9(6):1923-28, 1990.

Wissinger et al., "*Trans* Splicing in Oenothera Mitochondria: *nad1* mRNAs Are Edited in Exon and *Trans*-Splicing Group II Intron Sequences" *Cell*, 65(3):473-82, May 3, 1991.

Woodson et al., "Reverse Self-Splicing of the Tetrahymena Group I Intron: Implication of the Directionality of Splicing and for Intron Transposition" *Cell*, 57:335-45, Apr. 21, 1989.

Xiang et al., "Sequence Specificity of a Group II Intron Ribozyme: Multiple Mechanisms for Promoting Unusually High Discrimination against Mismatched Targets" *Biochem*., 37: 3839-49, Feb. 27, 1998.

Xue, et al., "A Gene Cluster for Macrolide Antibiotic Biosynthesis in Streptomyces Venezuelae: Architecture of Metabolic Diversity", *Proc. Natl. Acad. Sci, USA*. 95: 12111-116, Oct. 1998.

Yang, et al., "Efficient Integration of an Intron RNA into Double-Stranded DNA by Reverse Splicing", *Nature*, 381: 332-35, May 23, 1996.

Yu, et al., "Direct Evidence that the Rifamycin Polyketide Synthase Assembles Polyketide Chains Processively", *Proc. Natl. Acad. Sci, USA*. 96: 9051-56, 1999.

Zhou, et al., Polyketide Synthase Acyl Carrier Protein (ACP) as a Substrate and a Catalyst for Malonyl ACP Biosynthesis, *Chemistry & Biology*, 6(8): 577-84 1999.

Zimmerly, et al., "Group II Intron Mobility Occurs by Target DNA-Primed Reverse Transcription", *Cell*, 82, 545-54, Aug. 25, 1995.

Zimmerly, et al., "A Group II Intron RNA is a Catalytic Component of a DNA Endonuclease Involved in Intron Mobility", *Cell*, 83: 529-538, 1995.

Doyle, "High-throughput Cloning For Proteomics Research," *Methods Mol. Biol*., 310: 107-113, 2005.

Li, et al., "Ligation Independent Cloning Irrespective Of Restriction Site Compatability," *Nucl. Acids Res*., 25(20): 4165-4166, 1997.

Nisson, "Rapid And Efficient Cloning Of Alu-PCR Products Using Uracil DNA Glycosylase," *PCR Methods Appl*., 1(2): 120-123, 1991.

Patten, et al., "Applications Of DNA Shuffling To Pharmaceuticals And Vaccines," *Curr Opin Biotechnol*., 8(6): 724-733, 1997.

Silverman, et al., "Multivalent Avimer Proteins Evolved By Exon Shuffling Of A Family Of Human Receptor Domains," *Nature Biotech*., 23: 1556-1561, 2005.

Doyle, "High-Throughput Cloning For Proteomics Research," *Methods Mol. Biol*., 310: 107-113, 2005.

Li and Evans, "Ligation Independent Cloning Irrespective Of Restriction Site Compatability," *Nucl. Acids Res*., 25(20): 4165-4166, 1997.

Nisson, "Rapid And Efficient Cloning Of Alu-PCR Products Using Uracil DNA Glycosylase," *PCR Methods Appl*., 1(2): 120-123, 1991.

Patten, et al., "Applications Of DNA Shuffling To Pharmaceuticals And Vaccines," *Curr Opin Biotechnol*., 8(6): 724-733, 1997.

Silverman, et al., "Multivalent Avimer Proteins Evolved By Exon Shuffling Of A Family Of Human Receptor Domains," *Nature Biotech*., 23: 1556-1561, 2005.

Notice of Allowance mailed Oct. 12, 2007 for U.S. Appl. No. 11/132,356, publication No. US 2005-0191623 A1.

Barnes, *PNAS*, 91: 2216-2220, 1994.

Bolivar, et al., *Gene*, 2: 75-93, 1977.

Cadwell, et al., *PCR Methods Appl*., 2: 28-33, 1992.

Chen, et al., *J. Am. Chem. Soc*., 11: 8799-8800, 1994.

Crameri, et al., *BioTechniques*, 18: 194-196, 1995.

Dillon, et al., *BioTechniques*, 9: 298-300, 1990.

Goeddel, et al., *PNAS*, 76: 106-110, 1979.

Hayashi, et al., *BioTechniques*, 17: 310-314, 1994.

Heyneker, et al., *Nature*, 263: 748-752, 1976.

Hermes, et al., *Gene*, 84: 143-151, 1989.

Itakura, et al., *Science*, 198: 1056-1063, 1977.

Lashkari, et al., *PNAS*, 92: 7912-7915, 1995.

Mandecki, et al., *Gene*, 68: 101-107, 1988.

Mandecki, et al., *Gene*, 94: 103-107, 1992.

Prodromou, et al., *Protein Eng*., 5: 827-829, 1992.

Stemmer, *Nature*, 370: 389-391, 1994.

Stemmer, *PNAS*, 91: 10747-10751, 1994.

Watson, *Gene*, 70: 399-403, 1988.

Demarest et al., "Engineering stability into Escherchia coli secreted Fabs leads to increased functional expression", *Protein Eng Des Sel*, 19(7): 325-36, 2006.

Silverman et al., "Multivalent avimer proteins evolved byexon shuffling of a family of human receptor domains", *Nature Biotechnology*, 23(12): 1556-61, 2005.

Li, et al., *Applied Microbio. And Biotech*., 75(3): 703-709, 2007.

Li, et al., *Nature Methods YNat. Methods*, 4(3): 251-256, 2007.

Stemmer et al., "Single-step assembly of a gene and entire plasmid from large numbers of oligodeoxyribonucleotides", *Gene*, 164: 49-53, 1995.

Li et al., "Harnessing homologous recombination in vitro to generate recombinant DNA via SLIC", Nature Methods, 4 (3): 251-56, 2007.

Wu et al., "Simplified gene synthesis: A one-step approach to PCR-based gene construction", Journal of Biotechnology, 124: 496-503, 2006.

Kodumal et al., "Total synthesis of long DNA sequences: Synthesis of a contiguous 32-kb polyketide synthase gene cluster", PNAS, 101(44): 15573-78, 2004.

Zhu, *Biotechniques*, 43: 356-359, 2007.

Ailenberg, et al., "Description of a PCR-based technique for DNA splicing and mutagenesis by producing 5' overhangs with run through stop DNA synthesis utilizing Ara-C", BMC Biotechnology, Biomed Central LTD., 5(1):23-28, 2005.

Ailenberg, et al., "Site-directed mutagenesis using a PCR-based staggered re-annealing method without restriction enzymes", Biotechniques, 22(4):624-630, 1997.

Coljee, et al., "Seamless gene engineering using RNA- and DNA-overhang cloning", Nature Biotechnology, 18:789-791, 2000.

Donahue, et al., "Rapid gene cloning using terminator primers and modular vectors", Nucleic Acids Research, 30(18):E95, 2002.

Arnold et al., "A Working Strategy for Directed Enzyme Evolution," *Adv. Biochem. Eng. Biotechnol*. 58:2-14 (1997).

Bailey, "Toward A Science of Metabolic Engineering," *Science* 252:1668-1674 (1991).

Bebenek et al., "Analyzing Fidelity of DNA Polymerases," *Met. Enzymol*. 262:217-232 (1995).

Carter, "Improved Oligonucleotide-Directed Mutagenesis Using M13 Vectors" *Methods in Enzymol*. 154:382-403 (1987).

Crameri et al., "Construction and Evolution of Antibody-Phage Libraries by DNA Shuffling," *Nature Medicine* 2(1):100-103 (1996).

Crameri et al., "DNA Shuffling of a Family of Genes From Diverse Species Accelerates Directed Evolution," *Nature* 391:288-291 (1998).

Crameri et al., "Improved Green Fluorescent Protein by Molecular Evolution Using DNA Shuffling," *Nature Biotech*. 15:436-438 (1997).

Erlich, "PCR Technology," Stockton Press, NY, 60-70 (1989).

Gál et al., "Directional Cloning of Native PCR Products with Preformed Sticky Ends," *Mol. Gen. Genet*. 260(6):569-573 (1999).

gō et al., "Protein Structures and Split Genes," *Adv. Biophys*. 19:91-131 (1985).

Guo et al., "Group II Introns Designed to Insert into Therapeutically Relevant DNA Target Sites in Human Cells," *Science* 289:452-456 (2000).

Higuchi, "Using PCR to Engineer DNA," *PCR Technology: Principles and Applications for DNA Amplification*, New York, NY, Stockton Press (1989), 61-70 (XP-002142432).

Horsch et al., "Inheritance of Functional Foreign Genes in Plants," *Science*, 223:496-498 (1984).

Hutchinson et al., "Polyketide Synthase Gene Manipulation: A Structure-Function Approach in Engineering Novel Antibiotics," *Annu. Rev. Microbiol.* 49:201-238 (1995).

Jung, "A Simple and Efficient Method for the Oligodeoxyribonucleotide-Directed Mutagenesis of Double-Stranded Plasmid DNA," *Gene* 121:17-24 (1992).

Klein et al., "High-Velocity Microprojectiles for Delivering Nucleic Acids into Living Cells," *Nature* 327(7):70-73 (1987).

Kleinkauf et al., "Biosynthesis of Peptide Antibiotics," *Annu. Rev. Microbiol.* 41:259-289 (1987).

Kramer et al., "Oligonucleotide-Directed Construction of Mutations via Gapped Duplex DNA," *Methods in Enzymol.* 154:350-367 (1987).

Kramer et al., "Different Base/Base Mismatches Are Corrected with Different Effciencies by the Methyl-Directed DNA Mismatch-Repair System of *E. Coli*," *Cell* 38:879-887 (1984).

Levichkin et al., "A New Approach to Construction of Hybrid Genes: Homolog Recombination Method," *Mol. Biology*, 29:572-577 (1995).

Liao, "Modeling and Analysis of Metabolic Pathways," *Curr. Opin. Biotech.* 4:211-316 (1993).

López, et al., "The Pneumococcal Cell Wall Degrading Enzymes: A Modular Design to Create New Lysins?" *Microb. Drug Resist.* 3:199-211 (1997).

Nambiar et al., "Total Synthesis and Cloning of a Gene Coding for the Ribonuclease S Protein," *Science* 223:1299-1301 (1984).

Padgett et al., "Creating Seamless Junctions Independent of Restriction Sites in PCR Cloning," *Gene* 168(1):31-35 (1996).

Smith, "In Vitro Mutagenesis," *Ann. Rev. Genet.* 19:423-462 (1985).

Stemmer, "Searching Sequence Space," *Bio/Technology* 13:549-553 (1995).

Stemmer, "The Evolution of Molecular Computation," *Science* 270:1510 (1995).

Stephanopoulos, "Metabolic Engineering," *Curr. Opin. Biotech.* 5:196-200 (1994).

Stephanopoulos et al., "Metabolic Engineering - Methodologies and Future Prospects," *Trends. Biotechnol.* 11:392-396 (1993).

Van Liempt et al., "Principles of the Molecular Construction of Multienzyme Templates for Peptide Biosynthesis in Integrated Reaction Sequences," *Biomed. Biochim. Acta*, 50:256-59 (1991).

Wang, "Replication of M13 Single-Stranded Viral DNA Bearing Single Site-Specific Adducts by *Escherichia coli* Cell Extracts: Differential Efficiency of Translesion DNA Dynthesis for SOS-Dependent and SOS-Independent Lesions," *Biochemistry* 36:9486-9492 (1997).

Wells et al., "Cassette Mutagenesis: An Efficient Method for Generation of Multiple Mutations at Defined Sites," *Gene* 34:315-323 (1985).

Wold, "Replication Protein A: A Heterotrimeric, Single-Stranded DNA-Binding Protein Required for Eukaryotic DNA Metabolism," *Annu. Rev. Biochem.* 66:61-92 (1997).

Xin et al., "Assembly of linear functional expression elements with DNA fragments digested with asymmetric restriction endonucleases," *Biotechnol. Lett.* 25(11):901-904 (2003).

Yang et al., "Amplification, Cloning and Sequence Analyses of the VH and VK Genes of an Anti-Human CD3 Monoclonal Antibody," *Chinese Biochemical Journal* 10(2):213-217 (1994).

Baldwin, T., "Firefly Luciferase: The Structure is Known, But the Mystery Remains," *Structure*, Mar. 15, 1996; 4(3):223-8.

Baron, et al., "Protein Modules", *Trends Biochem. Sci.* 16: 13-17, 1997.

Bartel, et al., "Biosynthesis of Anthraquinones by Interspecies Cloning of Actinorhodin Biosynthesis Genes in Streptomycetes: Clarification of Actinorhodin Gene Functions", *J. Bacteriol.* 172: 4816-4826, 1990.

Böhm, et al., "Engineering of a minimal modular polyketide synthase, and targeted alteration of the stereospecificity of polyketide chain extension," *Chem Biol.*, Aug. 1998; 5(8):407-12.

Bork, "The Modular Architecture of Vertebrate Collagens" *FEBS Letter*, 307: 49-54, 1992.

Botstein and Shortle, "Strategies and Applications of in Vitro Mutagensis", *Science*, 229: 1193-1201, 1985.

Campbell, et al., The Modular Architecture of Leukocyte Cell-Surface Receptors, *Immunol. Rev.* 163:11-18, 1998.

Carter, "Site-Directed Mutagenesis", *Biochem. J.*, 237: 1-7, 1986.

Clever, "Recombinational Repair in Yeast: Functional Interactions Between Rad51 and Rad54 Proteins", *EMBO J.*, 16: 2535-2544, 1997.

Cline, "PCR Fidelity of Pfu DNA Polymerase and Other Thermostable DNA Polymerases", *Nucleic Acids Res.* 24: 3546-3551, 1996.

Cohen, et al., "Construction of Biologically Functional Bacterial Plasmids In Vitro" *Proc. Natl. Acad. Sci. USA*. 70: 3240-3244, 1973.

Cohen, et al., "Recircularization and Autonomous Replication of a Sheared R-Factor DNA Segment in *Escherichia Coli* Transformants", *Proc. Natl. Acad. Sci. USA*. 70: 1293-1297, 1973.

Coque, et al., "The Cephamycin Biosynthetic Genes pcbAB, Encoding a Large Multidomain Peptide Synthetase, and pcbC of Nocardia Lactamdurans are Clustered Together in an Organization Different from the Same Genes in Acremonium Chrysogenum and Penicillium Chrysogenum", *Mol. Microbiol.* 5: 1125-1133, 1991.

Cortes, et al., "An Unusually Large Multifunctional Polypeptide in the Erythromycin-Producing Polyketide Synthase of Saccharopolyspora Erythraea" *Nature*, 348: 176-178, 1990.

Decker, et al., "Identification of Streptomyces Olivaceus Tü 2353 Genes Involved in the Production of the Polyketide Elloramycin", *Gene*, 166: 121-126, 1995.

Diez, et al., "Cluster of Penicillin Biosynthetic Genes" *J. Biol. Chem.* 265: 16358-16365, 1990.

Eghtedarzadeh and Henikoff, "Use of Oligonucleotides to Generate Large Deletions", *Nucl. Acids Res.* 14: 5115, 1986.

Engel, "Common Structural Motifs in Proteins of the Extracellular Matrix" *Curr. Opin. Cell. Biol.* 3: 779-785, 1991.

Engel, "Domain Organizations of Modular Extracellular Matrix Proteins and Their Evolution" *Matrix Biol.* 15: 295-299, 1996.

Fernandez-Moreno, et al., "Nucleotide Sequence and Deduced Functions of a Set of Cotranscribed Genes of Streptomyces Coelicolor A3(2) Including the Polyketide Synthase for the Antibiotic Actinorhodin", *J. Biol. Chem.* 267: 19278-19290, 1992.

Fraley, et al., "Expression of Bacterial Genes in Plant Cells", *Proc. Natl. Acad. Sci. USA*. 80:4803, 1983.

Fritz, et al., "Oligonucleotide-Directed Construction of Mutations: A Gapped Duplex DNA Procedure Without Enzymatic Reactions in Vitro", *Nucl. Acids Res.* 16: 6987-6999, 1988.

Fromm, et al., "Expression of Genes Transferred into Monocot and Dicot Plant Cells by Electroporation", *Proc. Natl. Acad. Sci. USA*. 82: 5824, 1985.

Gibson, et al., "Wild Potato Repels Aphids by Release of Aphid Alarm Pheromone", *Nature*, 302: 608-609, 1983.

Gilbert, et al., "Origin of Genes" *Proc. Natl. Acad. Sci. USA*. 94: 7698-7703, 1997.

Grundström, et al., "Oligonucleotide-Directed Mutagenesis by Microscale "Shot-Gun" Gene Synthesis", *Nucl. Acids Res.* 13: 3305-3316, 1985.

Hegyi, et al., "On the Classification and Evolution of Protein Modules", *J. Protein Chem* 16: 545-551, 1997.

International Search Report, Int'l Pub. No. WO 2003/030623 A3, PCT/US2000/00189, date of mailing Oct. 18, 2000.

International Search Report, Int'l Pub. No. WO 00/40715 A3, PCT/US2002/033023, date of mailing Dec. 24, 2003.

Kiianitsa, "Helical Repeat of DNA in the Region of Homologous Pairing", *Proc. Natl. Acad. Sci. USA*, 94: 7837-7840, 1997.

Kishore, et al., "Modular Organization of Carbohydrate Recognition Domains in Animal Ledtins" *Matrix Biol.* 15: 583-592, 1997.

Kramer, et al., "Improved Enzymatic in Vitro Reactions in the Gapped Duplex DNA Approach to Oligonucleotide-Directed Construction of Mutations" *Nucl. Acids Res.* 16: 7207, 1988.

Kramer, et al., "The Gaped Duplex DNA Approach to Oligonucleotide-Directed Mutation Construction", *Nucl. Acids Res.* 12: 9441-9456, 1984.

Kratzschmar, et al., "Gramicidin S Biosynthesis Operon Containing the Structural Genes grsA and grsB Has an Open Reading Frame Encoding a Protein Homologous to Fatty Acid Thioesterases" *J. Bacteriol.* 171: 5422-5429, 1989.

Kunkel, "The Efficiency of Oligonucleotide-Directed Mutagenesis", *Proc. Natl. Acad. Sci. USA*, 82: 488-492, 1985.

Kunkel, et al., "Rapid and Efficient Site-Specific Mutagenesis Without Phenotypic Selection", *Methods in Enzymol*, 154: 367-382.

Lal, et al., "Engineering Antibiotic Procedures to Overcome the Limitations of Classical Strain Improvement Programs," *Crit Rev Microbio.*, 1996; 22(4):201-55.

Lebedenko, et al., "Method of Artificial DNA Splicing by Directed Ligation," *Nucleic Acids Research*, 19(24): 6757-6761, 1991.

MacCabe, et al., "δ-(L-α-Aminoadipyl)-L-Cysteinyl-D-Valine Synthetase from Aspergillus Nidulans" *J. Biol. Chem.* 266: 1264612654, 1991.

Marban, et al., "Structure and Function of Voltage-Gated Sodium Channels" *J. Physiol.* 508: 647-657, 1998.

Mootz, et al., "Biosynthetic Systems for Nonribosomal Peptide Antibiotic Assembly" *Curr. Op. Chem. Biol.* 1:543-551, 1997.

Mörl, et al., "Group II intron RNA-catalyzed recombination of RNA in vitro," Nov. 25, 1990; 18(22):6545-51.

Musacchio, et al., "The PH Domain: A Common Piece in the Structural Patchwork of Signalling Proteins" *Trends Biochem Sci.* 18: 343-348, 1993.

Myers, et al., "Reverse Transcription and DNA Amplification by a Thermus Thermophilus DNA Polymerase", *Biochem.* 6: 7661-7672, 1991.

Naismith, et al., "Tumor Necrosis Factor Receptor Superfamily", *J. Inflamm.* 47: 1-7, 1995.

Nakamaye and Eckstein, "Inhibition of Restriction Endonuclease Nci I Clevage by Phosphorothioate Groups and Its Application to Oligonucleotide-Directed Mutagenesis", *Nucl. Acids. Res.* 14: 1299-1301, 1984.

Rapley, "The Biotechnology and Applications of Antibody Engineering" *Mol. Biotechnol.* 3: 139-154, 1995.

Rashtchian, et al., "Uracil DNA Glycosylase-Mediated Cloning of Polymerase Chain Reaction-Amplified DNA: Application to Genomic and cDNA Cloning" *Analytical Biochemistry*, 206: 91-97, 1992.

Sakmar and Khorana, "Total Synthesis and Expression of a Gene for the α-Submit of Bovine Rod Outer Segment Guanine Nucleotide-Binding Protein (Transducin)" *Nucl. Acids Res.* 14: 6361-6372, 1988.

Sancar, "Mechanisms of DNA Excision Repair", *Science*, 266: 1954-1956, 1994.

Sayers, et al., "5'-3' Exonucleases in Phosphorothioate-Based Oligonucleotide-Directed Mutagenesis" *Nucl. Acids Res.* 16: 791-802, 1988.

Sayers, et al., "Strand Specific Cleavage of Phosphorothioate-Containing DNA by Reaction with Restriction Endonucleases in Presence of Ethiodum Bromide" Nucl. Acids Res. 16: 803-814, 1988.

Schaffhausen, "SH2 Domain Structure and Function" *Biochim. Biophys. Acta.* 28:61-75, 1995.

Schmeizer et al., "Self-Splicing of Group II Introns In Vitro: Mapping of the Branch Point and Mutation Inhibition of Lariat Formation" *Cell*, 46:557-65, Aug. 15, 1986.

Sherman, et al., Structure and Deduced Function of the Granaticin-Producing Polyketide Synthase Gene Cluster of Streptomyces Violaceoruber T22*EMBO, J.*, 8: 2717, 1989.

Shokat, "Tyrosine Kinases: Modular Signaling Enzymes with Tunable Specificities", *Chem. Biol.* 2: 509-514, 1995.

Smith, "The Animal Fatty Acid Synthase: One Gene, One Polypeptide, Seven Enzymes" *FASEB J.*, 8: 1248-1259, 1994.

Smith, et al., "Multifunctional Peptide Synthetase Performing the First Step of Penicillin Biosynthesis in Penicillium Chrysogenum is a 421 073 Dalton Protein Similar to *Bacillus Brevis* Peptide Antibiotic Synthetases" *EMBO J.* 9: 2743-2750, 1990.

Smith, et al., "β-Lactam Antibiotic Biosynthetic Genes have Been Conserved in Clusters in Porkaryotes and Eukaryotes", *EMBO J.* 9: 741-747, 1990.

Stoessl, et al., "Sesquiterpenoid Stress Compounds of the Solanaceae" *Phytochemistry*, 15: 855-872, 1976.

Strelets, et al., "Ancient Splice Junction Shadows with Relation to Blocks in Protein Structure" *Biosystems*, 36: 37-41, 1995.

Sudol, From Src Homology Domains to Other Signaling Modules: Proposal of the "Protein Recognition Code" *Oncogene*, 17: 1469-1474, 1998.

Sung, "Yeast Rad55 and Rad57 Proteins Form a Heterodimer that Functions with Replication Protein A to Promote DNA Strand Exchange by Rad51 Recombinase" *Genes Dev.*, 11: 1111-1121, 1997.

Taylor, et al., "Modular Domains of Focal Adhesion-Associated Proteins" *Curr. Top Microbiol. Imunol.* 228: 135-163, 1998.

Taylor, et al., The Rapid Generation of Oligonucleotide-Directed Mutation at High Frequency Using Phosphorothioate-Modified DNA *Nucl. Acids Res.* 13: 8765-8787, 1985.

Taylor, et al., "The Use of Phosphorothioate-Modified DNA in Restriction Enzyme Reactions to Prepare Nicked DNA" *Nucl. Acids Res.* 13: 8749-8764, 1985.

Traut, "Are Proteins Made of Modules?" *Mol. Cell Biochem.* 70: 3-10, 1986.

Wells, et al., "Importance of Hydrogen-Bond Formation in Stabilizing The Transition State of Subtilisin" *Phil. Trans. R. Soc. Lond.*, A 317: 415-423, 1986.

Zhang, et al., "Directed Evolution of a Fucosidase From a Galactosidase by DNA Shuffling and Screening" *Proc. Natl. Acad. Sci. USA*, 94: 4504-4509, 1997.

Zhao, et al., "Optimization of DNA Shuffling for High Fidelity Recombination" *Nucleic Acids Res.* 25: 1307-1308, 1997.

\* cited by examiner

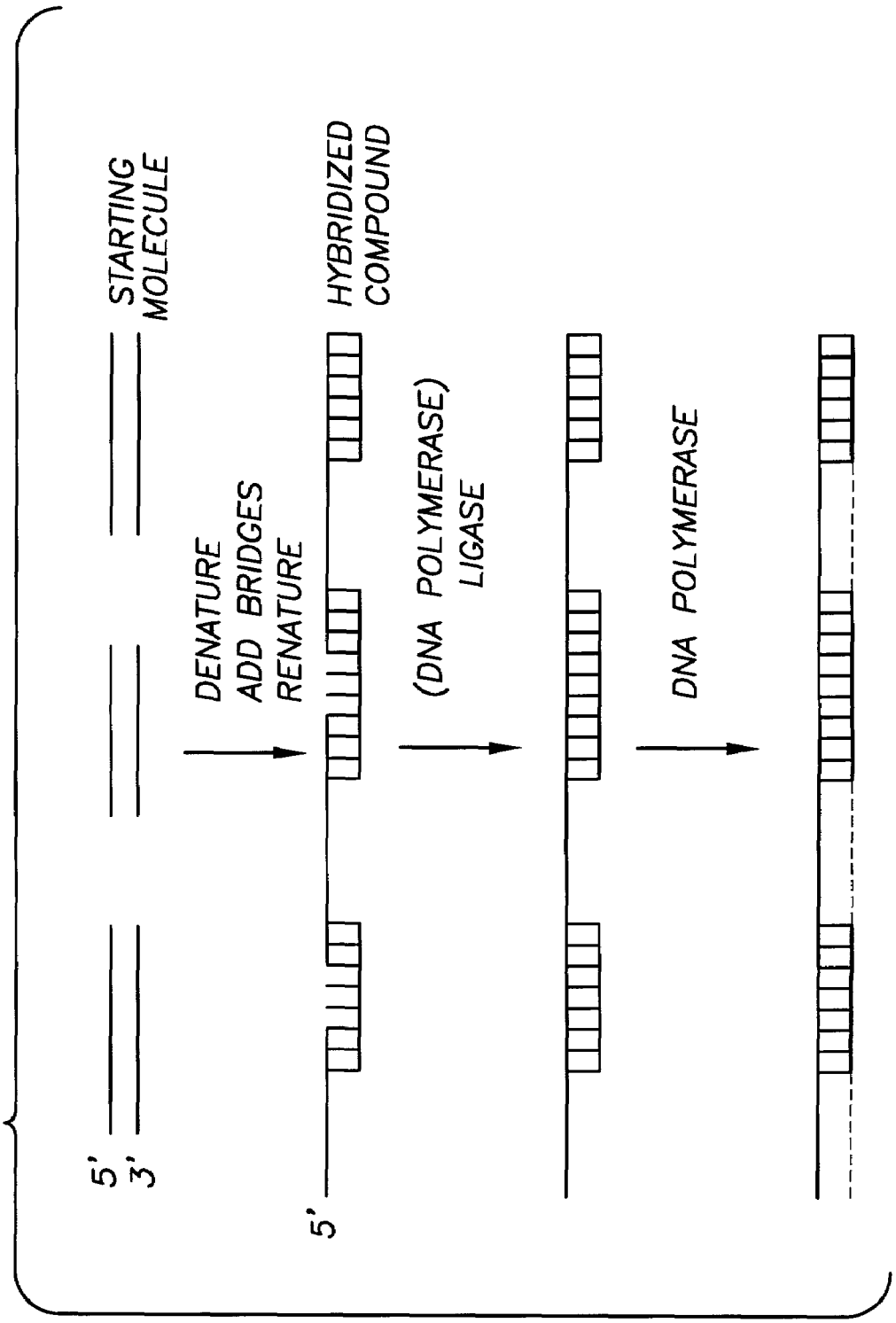

FIG. 7

Drugs Synthesized by Polyketide Synthases

| | |
|---|---|
| Azithromycin | Idarubicin (Idamycin) |
| Clarithromycin | Amphotericin B |
| Erythromycin | Candicidin |
| Dalfopristin | Griseofulvin |
| Josamycin | Nystatin/Mycostatin |
| Minocycline (Dynacil) | Spirmycin |
| Miokamycin | Mevacor (Lovastatin) |
| Mycinamicin | Mevastatin (Compactin) |
| Oleandomycin | Pravastatin |
| Pristinamycin | Zocor |
| Pseudomonic acid | Zearalenone |
| Rifamycins (Rifampin) | Ascomycin (Immunomycin) |
| Rokitamycin (Ricamycin) | FK506 |
| Roxithromycin | Sirolimus (Rapamycin) |
| Tetracyclines | Avermectin |
| Aclarubicin (aclacinomycin) | Doramectin |
| Adriamycin (Doxorubicin) | Lasalocid A |
| Chromomycin | Milbemycin |
| Daunorubicin | Monensin |
| Enediynes | Tylosin |

AT= acyl transferase
ACP= acyl carrier protein
KS= β-ketoacyl synthase
KR= β-ketoacyl reductase
ER= enoyl reductase
DH= dehydratase
TE= thioesterase Intermediates in Chain extension Cycles

TO FIG. 8-2

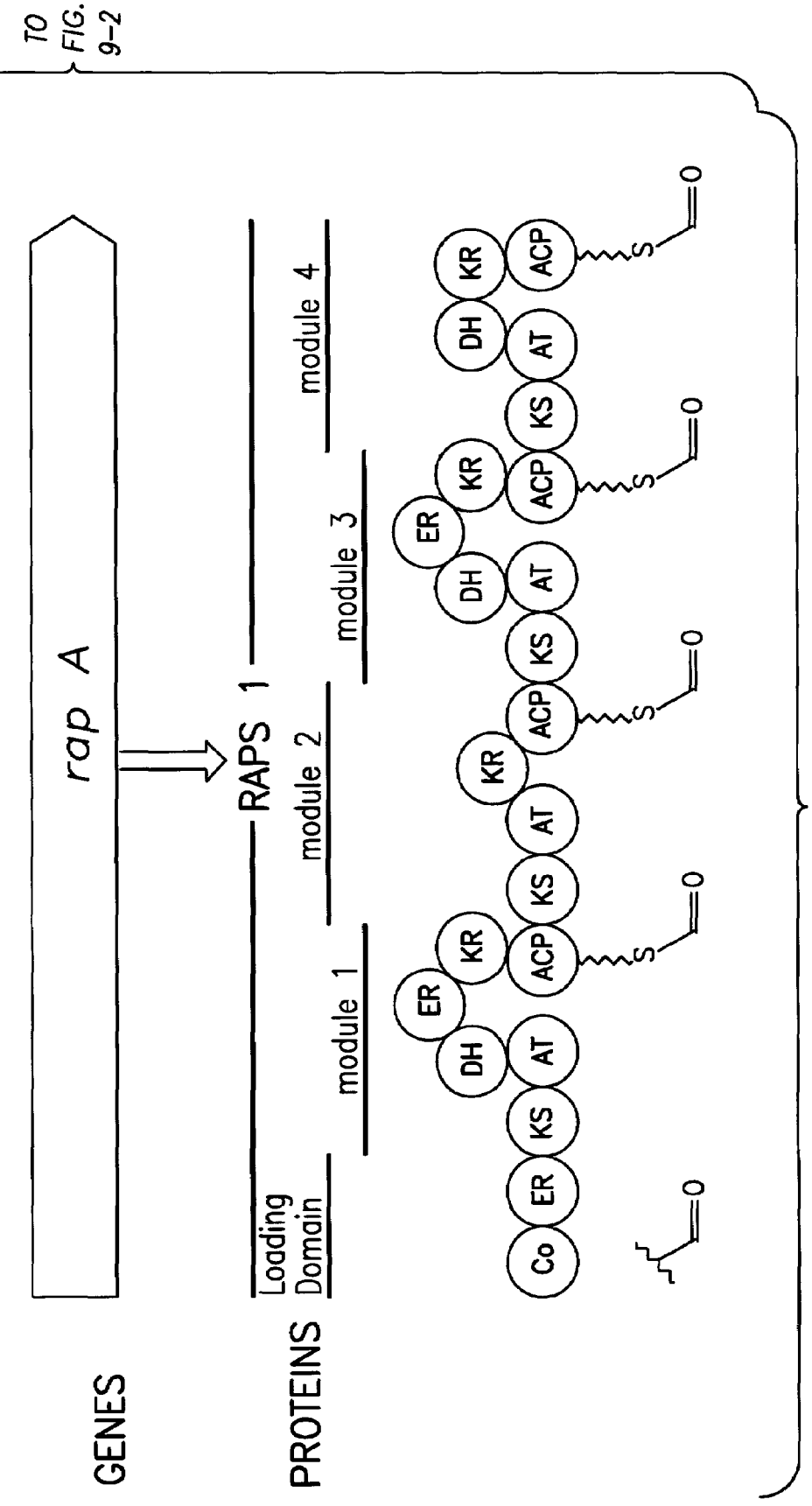

RAPS 1 — 8566 amino acids
RAPS 2 — 10222 amino acids
RAPS 3 — 6250 amino acids

FIG.11

Drugs Synthesized by Peptide Synthetases

| |
|---|
| Pencillin |
| Cephalosporins |
| Clavulanic acid |
| Bialaphos |
| Pristinamycins |
| Actinomycin |
| Viridogrisein |
| Enniatins |
| A47934 |
| Vanocomycin |
| Teichoplanin |
| Ardacin |
| Surfactin |
| Bacitracin |
| Cyclosporin |

FIG.19A

ORIGIN
```
  1 tcattaggaa cccagtaaa tcttgcagta ttgaaactca gtgagcaagg cgtcttagac
 61 aagctgaaaa acaaatggtg gtacgataaa ggtgaatgtg gagccaagga ctctggaagt
121 aagaaagac cagtgccctc agtctgagca acgttgctgg agtattctac atccttgtcg
181 ggggcctt
```

FIG.19B

ORIGIN
```
  1 tcattaggaa atgcggttaa cctcgcagta ctaaaactga atgaacaagg cctgttggac
 61 aaattgaaaa acaaatggtg gtacgacaaa ggagagtgcg gcagcggggg agtgattcc
121 aagggaaag accagtgccc tcagtctgag caacgttgct ggagtattat acatccttgt
181 cggggccttt
```

Individual PCR amplified fragments and the PCR amplidied chimeric contruct

The Flop/β-globin intron/Flip chimera ligation site sequences

TO FIG.22A-2

FROM FIG.22A-1

FIG.22B-1

```
                            Ple I
                            Hinf I
       Nla  III      Mbo II
      Nsph I         Bby II
      Nsp7524 I
       ||            |   |
      CTGGGCATGTGGAGACAGAGAAGACTCTTGGGTTTCTGATAGGCA
      GACCCGTACACCTCTGTCTCTTCTGAGAACCCAAAGACTATCCGT
       ||     •      |   |      •        •
       165           180
       165           180
        166                 183
                            183
                      Flip (115bp)
```

```
      Dde I                                 Dde I
       |                                     |
      CTTAG AACCCCAGTAAATCTTGCAGTATTGAAACTCAGTGAGCAA
      GAATC TTGGGGTCATTTAGAACGTCATAACTTTGAGTCACTCGTT
       | **  •        •        •        •   |     •
      241                                   274
```

```
                             Ple I
                             Sty I
                             Sec I  Ava I
      Hph I       Nla IV     Hinf I
       |           |   |      |  |
      CGATAAAGGTGAATGTGGAGCCAAGGACTCGGGAAGTAAG    360
      GCTATTTCCACTTACACCTCGGTTCCTGAGCCCTTCATTC
       | •         |   • |    | |  •           •
       328         337        346
                              348
                   341
                   341
                       346
```

```
       Ple I
       Hinf I
       |
       CTGACTCTCTCTGCCTATTGGTCTATTTTCCCACC    240
       GACTGAGAGAGACGGATAACCAGATAAAAGGGTGG
       | •         •       •      •       •
       208
       208

Dde I
       Hga I
       Aha II              Alu I                      Rsa I
       |||                 |                          |
       GGCGTCTTAGACAAGCTGAAAAACAAATGGTGGTA    320
       CCGCAGAATCTGTTCGACTTTTTGTTTACCACCAT
       || •|               | •         •   | •
       286                 299              318
        287
          291
```

\* Ribonucleotide in primer

FROM FIG. 22B-1

FIG.24
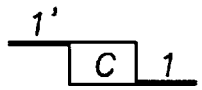
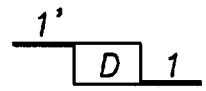
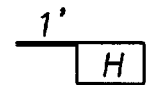

FIG.25

LIBRARY ASSEMBLY USING
RNA/DNA CHIMERIC OLIGOS

A | OVERHANG 1

OVERHANG 1'
| B | OVERHANG 2

OVERHANG 2'
| B |

COMBINATORIAL POTENTIAL $10 \times 3 = 30$
$10^3 = 1000$

FIG. 26  LIBRARY ASSEMBLY USING RNA/DNA CHIMERIC OLIGOS AND INTRON SPLICING

FIG. 30
EXON SHUFFLING WITH HETEROLOGOUS INTRONS
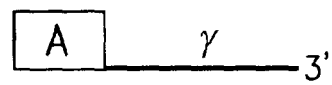
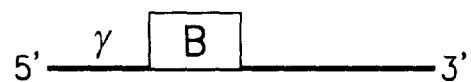
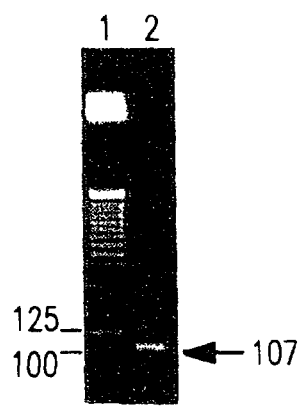
COMPINATORIAL POTENTIAL
$10 \times 3 = 30$
$10^3 = 1000$

SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer 1 in
      Figure 18

<400> SEQUENCE: 1
aaatgcggtt aacctcgcag                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Combined DNA/RNA Molecule:
      oligonucleotide in which first four residues are RNA; remainder
      residue DNA
<220> FEATURE:
<223> OTHER INFORMATION: Primer 2 in Figure 18; oligonucleotide in which
      first four residues are RNA; remainder residues are DNA

<400> SEQUENCE: 2
accutggaat caccctccccc                                             20

<210> SEQ ID NO 3
<211> LENGTH: 20
<212> TYPE: DNA
<213> ORGANISM: Artificial Sequence
<220> FEATURE:
<223> OTHER INFORMATION: Description of Combined DNA/RNA Molecule:
      oligonucleotide in which first four residues are RNA; remainder
      residue DNA
<220> FEATURE:
<223> OTHER INFORMATION: Description of Artificial Sequence: Primer 3 in
      Figure 18; oligonucleotide in which first four residues are RNA;
      remainder residues are DNA

<400> SEQUENCE: 3
aggutggtat caaggttaca                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Combined DNA/RNA Molecule:
      oligonucleotide in which first two residues are RNA; remainder
      residue DNA
<220> FEATURE:
<223> OTHER INFORMATION: Description of Artificial Sequence: Primer 4 in
      Figure 18; oligonucleotide in which first two residues are RNA;
      remainder residue DNA

<400> SEQUENCE: 4
cuaaccccag taaatcttgc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Combined DNA/RNA Molecule:
      oligonucleotide in which first two residues are RNA; remainder
      residue DNA

```
<220> FEATURE:
<223> OTHER INFORMATION: Description of Artificial Sequence: Primer 5 in
      Figure 18; oligonucleotide in which first two residues are RNA;
      remainder residue DNA

<400> SEQUENCE: 5
agaagggtgg gaaaatagac                                                      20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer 6 in
      Figure 18

<400> SEQUENCE: 6
cttacttccc gagtccttgg                                                      20

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer
      BAMHI.E5

<400> SEQUENCE: 7
acgggatcca tacttactac gtggtgggac                                           30

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Primer
      D4.SAII

<400> SEQUENCE: 8
acggtcgacc ctcctatctt ttttaatttt ttttt                                     35

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Primer
      KpnI.D4

<400> SEQUENCE: 9
acgggtacct ttatatataa ctgataaata tttatt                                    36

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Primer
      E3.BamHI

<400> SEQUENCE: 10
acgggatcca gaaaatagca cccattgata a                                         31

<210> SEQ ID NO 11
<211> LENGTH: 30
<212> TYPE: DNA
<213> ORGANISM: Artificial Sequence
```

```
<220> FEATURE:
<223> OTHER INFORMATION: Description of Artificial Sequence: Expected
      sequence in pD4.E3(dc).B 3'exon

<400> SEQUENCE: 11
actatgtatt atcaatgggt gctattttct                                          30

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Observed
      sequence in pD4.E3(d c) B 3'exon

<400> SEQUENCE: 12
actatgtatt ataatgggtg ctattttct                                           29

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Primer
      E3.BamHI(2)

<400> SEQUENCE: 13
ctctagagga tccagaaaat aggatccatt ataatacata gtatcccg                      48

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Primer
      E3.BamHI(2) Complement

<400> SEQUENCE: 14
cgggatacta tgtattataa tggatcctat tttctggatc ctctagag                      48

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Primer
      5'transM.E.5'

<400> SEQUENCE: 15
cacgggatcc gaacacatcc ataacgtgc                                           29

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Primer
      5'sht3'

<400> SEQUENCE: 16
cagcgtcgac gtacccottt gccatgt                                             27

<210> SEQ ID NO 17
<211> LENGTH: 43
<212> TYPE: DNA
<213> ORGANISM: Artificial Sequence
<220> FEATURE:
```

```
<223> OTHER INFORMATION: Description of Artificial Sequence: Primer
      3'transM.E.5'

<400> SEQUENCE: 17
cacggagctc ttattgtgta ctaaaattaa aaattgatta ggg                    43

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Primer
      3'transM.E.3'

<400> SEQUENCE: 18
cagcggatcc cgtagaatta aaaatgatat ggtgaagtag                        40

<210> SEQ ID NO 19
<211> LENGTH: 188
<212> TYPE: DNA
<213> ORGANISM: Human GLU-R2 glutamate receptor subunit

<400> SEQUENCE: 19
tcattaggaa ccccagtaaa tcttgcagta ttgaaactca gtgagcaagg cgtcttagac    60
aagctgaaaa acaaatggtg gtacgataaa ggtgaatgtg gagccaagga ctctggaagt   120
aagaaaagac cagtgccctc agtctgagca acgttgctgg agtattctac atccttgtcg   180
ggggcctt                                                           188

<210> SEQ ID NO 20
<211> LENGTH: 190
<212> TYPE: DNA
<213> ORGANISM: Human GLU-R2 glutamate receptor subunit

<400> SEQUENCE: 20
tcattaggaa atgcggttaa cctcgcagta ctaaaactga atgaacaagg cctgttggac    60
aaattgaaaa acaaatggtg gtacgacaaa ggagagtgcg gcagcggggg aggtgattcc   120
aagggaaaag accagtgccc tcagtctgag caacgttgct ggagtattct acatccttgt   180
cgggggcctt                                                         190

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: The
      Flop/B-globin intron/flip chimera ligation site sequences.

<400> SEQUENCE: 21
gggaatcttg ggg                                                     13

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: The
      flop/B-globin intron/flip chimera ligation site sequences

<400> SEQUENCE: 22
tggttggaac c                                                       11
```

-continued

```
<210> SEQ ID NO 23
<211> LENGTH: 360
<212> TYPE: DNA
<213> ORGANISM: Artificial Sequence
<220> FEATURE:
<223> OTHER INFORMATION: Description of Artificial Sequence: Artificial
      sequence of ligated product.

<400> SEQUENCE: 23
aaatgcggtt aacctcgcag tactaaaact gaatgaacaa ggcctgttgg acaaattgaa      60
aaacaaatgg tggtacgaca aaggagagtg cggcagcggg ggaggtgatt ccaaggttgg     120
tatcaaggtt acaagacagg tttaaggaga ccaatagaaa ctgggcatgt ggagacagag    180
aagactcttg ggtttctgat aggcactgac tctctctgcc tattggtcta ttttcccacc    240
cttagaaccc cagtaaatct tgcagtattg aaactcagtg agcaaggcgt cttagacaag    300
ctgaaaaaca aatggtggta cgataaaggt gaatgtggag ccaaggactc gggaagtaag    360

<210> SEQ ID NO 24
<211> LENGTH: 20
<212> TYPE: DNA
<213> ORGANISM: Artificial Sequence
<220> FEATURE:
<223> OTHER INFORMATION: Description of Combined DNA/RNA Molecule:
      oligonucleotide in which first two residues are RNA; remainder
      residue DNA
<220> FEATURE:
<223> OTHER INFORMATION: Description of Artificial Sequence: Primer 4,
      oligonucleotidek in which first two residues are RNA; remainder
      residue DNA

<400> SEQUENCE: 24
uucuaagggt gggaaaatag                                                  20

<210> SEQ ID NO 25
<211> LENGTH: 19
<212> TYPE: DNA
<213> ORGANISM: Artificial Sequence
<220> FEATURE:
<223> OTHER INFORMATION: Description of Combined DNA/RNA Molecule:
      oligonucleotide in which first two residues are RNA; remainder
      residue DNA
<220> FEATURE:
<223> OTHER INFORMATION: Description of Artificial Sequence: primer 5;
      oligonucleotide in which first two residues are RNA; remainder
      residue DNA.

<400> SEQUENCE: 25
agaacccagt aaatcttgc                                                   19
```

NUCLEIC ACID CLONING

The present application is a Continuation-in-part of U.S. National patent application Ser. No. 09/225,990, filed Jan. 5, 1999 now U.S. Pat. No. 6,358,712, and is also a U.S. National Application PCT/US00/00189 filed Jan. 5, 2000 under 35 USC § 271. This application also claims priority to U.S. Provisional Patent Application Ser. No. U.S.S.N. 60/114,909, filed on Jan. 5, 1999. Each of these three priority applications is incorporated herein by reference in its entirety.

GOVERNMENT FUNDING

Some or all of the work described herein was supported by grant number RO1 GM 52409 from the National Institutes of Health and by grant number MCB9604458 from the National Science Foundation; the United States Government may have certain rights in this invention.

BACKGROUND

The Molecular Biology revolution began with the discovery of enzymes that were capable of cleaving double stranded DNA, so that DNA fragments were produced that could be ligated to one another to generate new, so-called "recombinant" molecules (see, for example, Cohen et al., *Proc. Natl. Acad. Sci. USA* 70:1293, 1973; Cohen et al., *Proc. Natl. Acad. Sci. USA* 70:3274, 1973; see also U.S. Pat. Nos. 4,740,470; 4,468,464; 4,237,224). The revolution was extended by the discovery of the polymerase chain reaction (PCR), which allowed rapid amplification of particular DNA segments, producing large amounts of material that could subsequently be cleaved and ligated to other DNA molecules (see, for example, U.S. Pat. Nos. 4,683,195; 4,683,202; 5,333,675).

Despite the power of these digestion and amplification techniques, however, there remains substantial room for improvement. Reliance on digesting enzymes, called "restriction enzymes", can render molecular biological experiments quite expensive. Moreover, many of the enzymes are inefficient or are only available in crude preparations that may be contaminated with undesirable entities.

At first, it seemed that PCR amplification might itself avoid many of the difficulties associated with traditional cut-and-paste cloning methods since it was thought that PCR would generate DNA molecules that could be directly ligated to other molecules, without first being cleaved with a restriction enzyme. However, experience indicates that most PCR products are refractory to direct cloning. One possible explanation for this observation has come from research revealing that many thermophilic DNA polymerases (including Taq, the most commonly used enzyme) add terminal 3'-dAMP residues to the products they amplify. Invitrogen (Carlsbad, Calif.) has recently developed a system for direct cloning of such terminally-dAMP-tagged products (TA Cloning Kit®; see U.S. Pat. No. 5,487,993) if the molecule to which they are to be ligated is processed to contain a single unpaired 3'-dTMP residue. While the Invitrogen system has proven to be very useful, it is itself limited in application by being restricted to ligation of products with only a single nucleotide overhang (an A residue), and is further restricted in that the overhang must be present at the 3' end of the DNA molecule to be ligated.

There is a need for the development of improved systems for nucleic acid cloning. Particularly desirable systems would allow DNA ligation with minimal reliance on restriction enzymes, would provide for efficient ligation, and would be generally useful for the ligation of DNAs having a wide variety of chemical structures. Optimal systems would even provide for directional ligation (i.e., ligation in which the DNA molecules to be linked together will only connect to one another in one orientation).

SUMMARY OF THE INVENTION

The present invention provides an improved system for linking nucleic acids to one another. In particular, the present invention provides techniques for producing DNA product molecules that may be easily and directly ligated to recipient molecules. The product molecules need not be cleaved with restriction enzymes in order to undergo such ligation. In preferred embodiments of the invention, the DNA product molecules are produced through iterative DNA synthesis reactions, so that the product molecules are amplified products.

The inventive system provides techniques and reagents for generating product molecules with 3' overhangs, 5' overhangs, or no overhangs, and further provides tools for ligating those product molecules with recipient molecules. Where overhangs are employed, the length and sequence of the overhang may be varied according to the desires of the practitioner. Overhang-containing products may be linked to one another by any available means including, for example, enzymatic ligation or transformation into a host cell. For example, molecules containing at least 12 nt overhangs may be annealed to one another and linked together by transformation into *E. coli* without first being ligated (see, for Example, Rashtchian, et al. *Annalytical Biochemistry* 206:91, 1992).

The inventive system further provides methods for directed ligation of product molecules (i.e., for selective ligation of certain molecules within a collection of molecules), and also for methods of exon shuffling, in which multiple different product molecules are produced in a single ligation reaction. Preferred embodiments of the invention involve ligation of product molecules encoding functional protein domains, particularly domains naturally found in conserved gene families. Alternative or additional preferred embodiments of the invention involve multi-component ligation reactions, in which three or more nucleic acid molecules are ligated together. In some embodiments, these multiple molecules are linked in only a single arrangement; in others, multiple arrangements can be achieved.

The inventive DNA manipulation system is readily integrated with other nucleic acid manipulation systems, such as ribozyme-mediated systems, and also is susceptible to automation. Specifically, in one aspect, a double stranded DNA molecule with a single stranded overhang comprised of RNA is provided. Additionally, in another aspect, a library of nucleic acid molecules is provided wherein each member of the library comprises 1) at least one nucleic acid portion that is common to all members of the library; and 2) at least two nucleic acid portions that differ in different members of the library, is also provided by the present invention. In a preferred embodiment, each of the nucleic acid portions in the library comprises protein-coding sequence and each library member encodes a continuous polypeptide. In yet another particularly preferred embodiment, each of the variable nucleic acid portions encodes a functional domain of a protein. This functional domain is preferably one that is naturally found in a gene family selected from the group consisting of the tissue plasminogen activator gene family, the animal fatty acid synthase gene family, the polyketide synthase gene family, the peptide synthetase gene family, and the terpene synthase gene family.

In yet another aspect of the present invention, a method of generating a hybrid double-stranded DNA molecule is provided. This method comprises the steps of 1) providing a first double-stranded DNA molecule, which double-stranded DNA molecule contains at least one single stranded overhang comprised of RNA; 2) providing a second double-stranded DNA molecule containing at least one single-strand overhang that is complementary to the RNA overhang on the first double-stranded DNA molecule; and 3) ligating the first and second double-stranded DNA molecules to one another so that a hybrid double-stranded DNA molecule is produced. In certain preferred embodiments, the method comprises providing and ligating at least three double-stranded DNA molecules.

A further aspect of the present invention includes a method of generating a hybrid double-stranded DNA molecule, the method comprising 1) generating a first double-stranded DNA molecule by extension of first and second primers, at least one of which includes at least one base that is not copied during the extension reaction so that the extension reaction produces a product molecule containing a first overhang; 2) providing a second double-stranded DNA molecule containing a second overhang complementary to the first overhang; and 3) ligating the first and second double-stranded DNA molecules to one another, so that a hybrid doable-stranded DNA molecule is produced. In certain preferred embodiments, the method comprises providing and ligating at least three double-stranded DNA molecules.

In still a further aspect of the present invention, a method of generating a hybrid double-stranded DNA molecule is provided, the method comprising: 1) generating a first double-stranded DNA molecule by extension of first and second primers, at least one of which includes at least one potential point of cleavage; 2) exposing the first double-stranded DNA molecule to conditions that result in cleavage of the cleavable primer at the potential point of cleavage, so that a first overhang is generated on the first DNA molecule; 3) providing a second double-stranded DNA molecule containing a second overhang complementary to the first overhang; and 4) ligating the first and second double-stranded DNA molecules to one another, so that a hybrid double-stranded DNA molecule is produced. In certain preferred embodiments, the method comprises providing and ligating at least three double-stranded DNA molecules.

DESCRIPTION OF THE DRAWING

FIG. 11 presents a list of products generated by peptide synthetases that are currently used as pharmacologic agents.

FIG. 19A depicts the nucleotide sequence of the glutamate receptor exons known as Flip (GenBank accession number X64829).

FIG. 19B depicts the nucleotide sequence of the glutamate receptor exons utilized are known as Flop (GenBank accession number X64830).

FIG. 22 presents the nucleotide sequence of the human β-globin gene.

FIG. 24 shows an inventive positional exon shuffling reaction.

FIG. 25 shows the combinatorial potential of certain inventive directed ligation techniques.

FIG. 30 shows a ribozyme mediated directional ligation reaction.

DEFINITIONS

Figure 1:
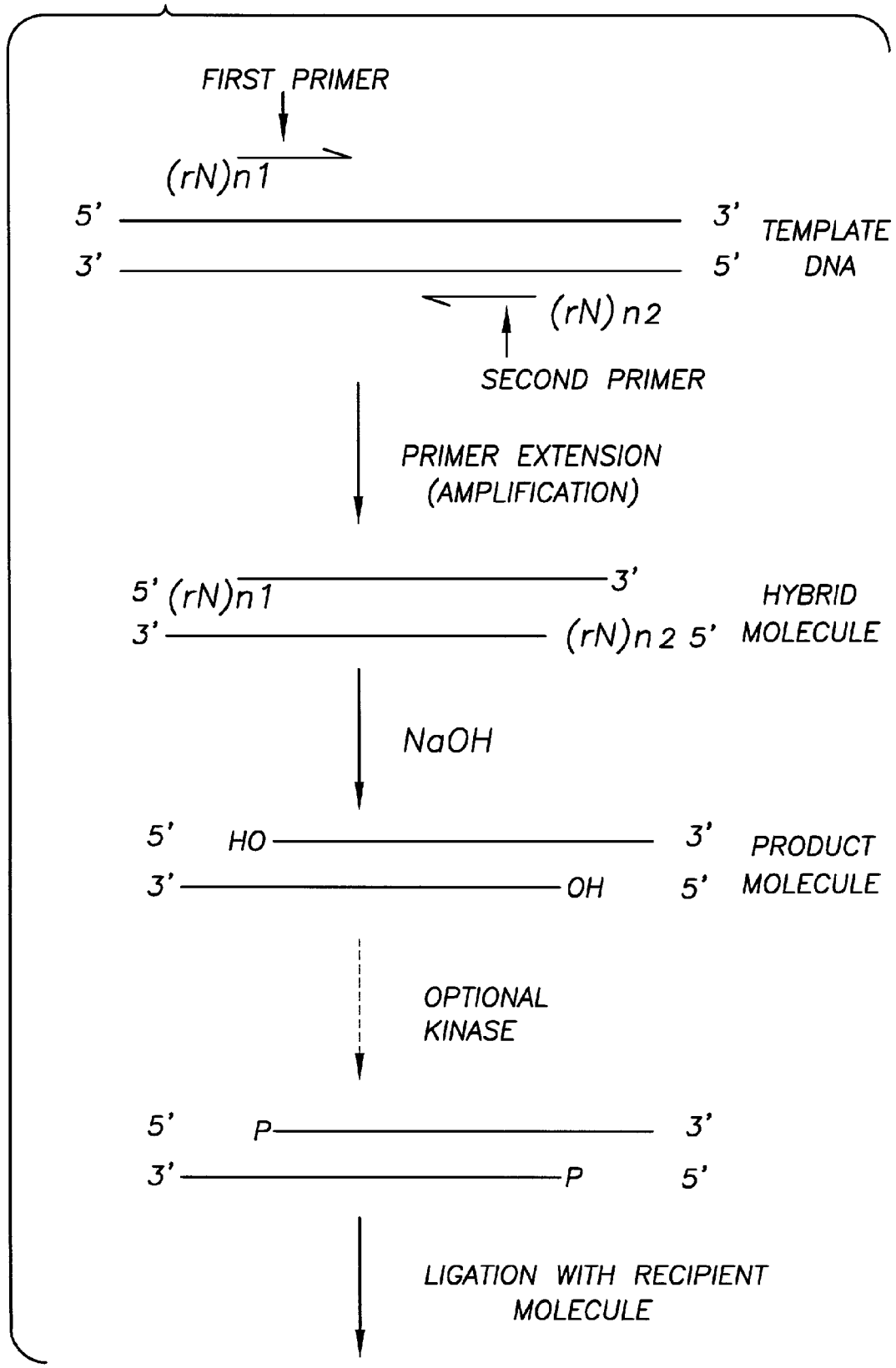
FIG. 1 depicts an inventive process for generating DNA product molecules with 3' overhangs.

"Cloning"—The term "cloning", when used herein, means the production of a new nucleic acid molecule through the ligation of previously unlinked nucleic acid pieces to one another. A molecule produced by such ligation is considered a "clone" for the purposes of the present application, even before it has been replicated.

"Direct ligation"—The term "direct ligation", as applied to product molecules herein, means that a product molecule may be ligated to one or more recipient molecules without first being cleaved with a restriction enzyme. Preferably, no processing of the product molecule is required at all prior to ligation.

"Expression"—"Expression" of nucleic acid sequences, as that term is used herein, means that one or more of (i) production of an RNA template from a DNA sequence; (ii) processing (e.g., splicing and/or 3' end formation) of a pre-mRNA to produce an mRNA; and (iii) translation of an mRNA has occurred.

"Gene"—For the purposes of the present invention, the term "gene" has its art understood meaning. However, it will be appreciated by those of ordinary skill in the art that the term "gene" has a variety of meanings in the art, some of which include gene regulatory sequences (e.g., promoters, enhancers, etc.) and/or intron sequences, and others of which are limited to coding sequences. It will further be appreciated that art definitions of "gene" include references to nucleic acids that do not encode proteins but rather encode functional RNA molecules, such as tRNAs. For the purpose clarity, we note that, as used in the present application, the term "gene" generally refers to a portion of a nucleic acid that encodes a protein; the term may optionally encompass regulatory sequences. This definition is not intended to exclude application of the term "gene" to non-protein-coding expression units, but rather to clarify that, in most cases, the term as used in this document happens to be applied to a protein-coding nucleic acid.

"Gene fragment"—A "gene fragment", as that term is used herein, means a piece of a protein-coding DNA molecule that is shorter than the complete protein-coding molecule. Preferably, the fragment is at least about 12 bases long, more preferably at least about 15-20 bases long, and may be several hundred or thousands of base pairs long. It should be understood that the fragment need not include protein-coding sequence, but rather may represent a non-coding portion of the original gene.

"Hybrid nucleic acid"—A "hybrid nucleic acid", as that term is used herein, means a nucleic acid molecule comprising at least a first segment and a second segment, each of which occurs in nature but is not linked directly with the other in nature, the first and second segments being directly linked to one another in the hybrid nucleic acid.

"Overhang sequence"—An "overhang sequence", as that term is used herein, means a single stranded region of nucleic acid extending from a double stranded region.

"Primer"—The term "primer", as used herein, refers to a polynucleotide molecule that is characterized by an ability to be extended against a template nucleic acid molecule, so that a polynucleotide molecule whose sequence is complementary to that of at least a portion of the template molecule, is linked to the primer. Preferred primers are at least approximately 15 nt long. Particularly preferred primers have a length within the range of about 18-30, preferably longer than approximately 20 nucleotides "Product molecule"—A "product molecule", as that term is used herein, is a nucleic acid molecule produced as described herein. Preferably, the product molecule is produced by extension of an oligonucleotide primer according to the present invention. A product molecule may be single stranded or double stranded. In certain preferred embodiments of the invention, a product molecule that includes a double-stranded portion also includes a single-stranded 3'- or 5'-overhang. In other preferred embodiments, the product molecule is blunt-ended. Where a product molecule is produced in an iterative DNA synthesis reaction (e.g., a PCR reaction), it is referred to as an "amplified product".

"Recipient molecule"—A "recipient molecule", as that term is used herein, is a nucleic acid molecule to which a product molecule is to be ligated. The recipient molecule may be, but is not required to be, a vector. In general, the recipient molecule can be any molecule selected by the practitioner.

"Vector"—A "vector", as that term is used herein, is a nucleic acid molecule that includes sequences sufficient to direct in vivo or in vitro replication of the molecule. Where the vector includes in vivo replication sequences, these sequences may be self-replication sequences, or sequences sufficient to direct integration of the vector into another nucleic acid already present in the cell, so that the vector sequences are replicated during replication of the already-present nucleic acid. Such already-present nucleic acid may be endogenous to the cell, or may have been introduced into the cell through experimental manipulation. Preferred vectors include a cloning site, at which foreign nucleic acid molecules, preferably inventive product molecules, may be introduced and ligated to the vectors. Particularly preferred vectors further include control sequences selected for their ability to direct in vivo or in vitro expression of nucleic acid sequences introduced into the vector. Such control sequences may include, for example, transcriptional control sequences (e.g., one or more promoters, regulator binding sites, enhancers, terminators, etc.), splicing control sequences (e.g., one or more splice donor sites, splice acceptor sites, splicing enhancers, etc.), and translational control sequences (e.g., a Shine Dalgarno sequence, a start codon, a termination codon, etc.). Vectors may also include some coding sequence, so that transcription and translation of sequences introduced into the vector results in production of a fusion protein.

DESCRIPTION OF CERTAIN PREFERRED EMBODIMENTS

Product Molecules with 3' Overhangs

In one aspect, the present invention provides reagents and methods for generating product molecules with 3' overhangs that can be directly ligated to recipient molecules. The length and sequence of the 3' overhang may be determined by the user.

FIG. 1 depicts one embodiment of this aspect of the invention. As shown in that Figure, first and second primers are provided that flank a target region of a template nucleic acid molecule. At least one of the primers includes one or more ribonucleotides at its 5' end. Specifically, if primer 1 is x nucleotides long and primer 2 is y nucleotides long, then n1=a whole number (including 0) from 0 to x and n2=a whole number (including 0) from 0 to y except that (i) n1 and n2 cannot both be 0; and (ii) n1 can only be x (or n2 can only be y) if the DNA polymerase employed in the extension reaction is capable of extending an RNA primer. The characteristics (e.g., ability to extend an RNA primer, ability to copy RNA into DNA [whether the RNA is presented alone or as part of a hybrid RNA/DNA molecule) of a wide variety of DNA polymerases are well known in the art (see, for example, manufacturer's catalogs, Myers et al., *Biochem.* 6:7661, 1991), and where such characteristics are not known for a particular DNA polymerase, routine assays are available for determining them (see, for example, Bebenek et al., *Met. Enzymol.* 262:217, 1995; see also Example 3).

In certain preferred embodiments of the invention, each of primers 1 and 2 includes at least one 5'-terminal ribonucleotide residue. In other preferred embodiments, at least one primer includes at least 2 ribonucleotide residues, one of which is the 5'-terminal residue. The primer may include at least 3, 4, 5, 6-10, or more ribonucleotide residues and even, as mentioned above, may be entirely RNA. Preferably, the ribonucleotide residues are contiguous with one another.

The nucleotide sequence of each of primer 1 and primer 2 is selected by the practitioner and need not be fully complementary with the sequence of the target nucleic acid. As is known in the art, perfect complementarity is not required for successful DNA synthesis, though it is generally desired that at least the 3'-terminal nucleotide of the primer be perfectly paired with the template. The 5' end of the primer, however, need not be paired at all, and it is common in the art to add additional sequences to a target sequence by including them in the primer. Of course, it is also acceptable for the primer to include a portion, 5' of the extendible 3' terminus, that does not hybridize with the template, and also to include a yet more 5' portion that does hybridize with the template. For the purposes of the present invention, any such variation on primer sequence, or any other available variation, is acceptable, so long as (i) at least one primer includes a ribonucleotide that either is present at the 5' end of the primer or will generate a new 5' end of the primer upon being removed from the primer (e.g., by alkaline treatment, preferably followed by kinase treatment); and (ii) each primer hybridizes sufficiently well and sufficiently specifically under the conditions of the reaction that a product molecule is produced.

Other considerations of primer design are well known in the art (see, for example, Newton et al. (eds), *PCR: Essential Data Series*, John Wiley & Sons, New York, N.Y., 1995; Dieffenbach (ed), *PCR Primer: a Laboratory Manual*, Cold Spring Harbor Laboratory Press, Cold Spring Harbor, N.Y., 1995; White et al. (eds), *PCR Protocols: Current Methods and Applications; Methods in Molecular Biology*, The Humana Press, Totowa, N.J., 1993; Innis et al., *PCR Protocols: A Guide to Methods and Applications*, Academic Press, San Diego, Calif., 1990; Griffin et al. (eds), *PCR Technology, Current Innovations*, CRC Press, Boca Raton, Fla. 1994, each of which is incorporated herein by reference). For instance, it is often desirable for approximately 50% of the hybridizing residues to be Gs or Cs; and may be desirable, for optimal extension, for the 3'-terminal residue to also be a G or a C.

Primers such as those depicted in FIG. 1, that contain at least one ribonucleotide residue as their 5' terminal residue (or as a residue whose removal will create a new 5'-terminal primer residue), may be prepared by any technique available in the art. For example, such primers may be chemically synthesized. Companies (e.g., Oligos, Etc., Inc., Bethel, Me.) that supply oligonucleotide reagents will typically prepare hybrid RNA/DNA oligonucleotides, or RNA only nucleotides, as preferred by the practitioner. Alternatively, RNA sequences may be ligated to DNA sequences using standard techniques (see, for example, Moore et al., Science 256:992, 1992; Smith (ed), *RNA: Protein Interactions, A Practical Approach*, Oxford University Press, 1998, which particularly discusses construction of RNA molecules containing site-specific modifications by RNA ligation; each of these references is incorporated herein by reference).

As shown in FIG. 1, an extension reaction is performed so that DNA synthesis is primed from each of the first and second primers, and a double stranded DNA/RNA hybrid molecule is created with at least one ribonucleotide residue at the 5' end of at least one strand. Preferably, but not essentially, the DNA polymerase utilized in the extension reaction is one that does not add extraneous 3' nucleotides. Also, as mentioned above, if one or both of the primers has a ribonucleotide as its 3' residue, the DNA polymerase utilized in the extension step must be one that is capable of extending from a ribonucleotide primer.

FIG. 1 shows that the hybrid molecule is then exposed to a treatment that removes the ribonucleotide residues. As depicted in FIG. 1, that treatment is exposure to elevated pH (e.g., treatment with a base such as sodium hydroxide [NaOH]). Any other treatment that removes RNA residues without disturbing DNA residues (e.g., exposure to RNase, etc.) could alternatively be employed at this step.

When the ribonucleotide residues are removed from the hybrid molecule, the resultant molecule is left with a double stranded portion and a single stranded 3' overhang on at least one of its ends. FIG. 1 depicts a product molecule with single-stranded 3' overhangs at both ends. The sequence and length of the overhang was determined by the sequence and length of RNA present at the 5' end of the primers. Clearly, any sequence and length of overhang can be selected. In certain preferred embodiments of the invention, the sequence and length of the overhang corresponds with that produced by cleavage of double-stranded DNA by a commercially available restriction enzyme, so that the product molecule can be ligated to recipient molecules that have been cut with that enzyme. A variety of enzymes that leave 3' overhangs are known in the art, including but not limited to AatII, AlwnI, NsiI, SphI, etc.

In other preferred embodiments, the 3' overhang sequence and length is selected to base pair with a 3' overhang generated in another inventive product molecule, so that the two molecules may readily be ligated together (see, for example, Example 1).

Furthermore, it will be appreciated that the 3' overhangs at the two ends of the product molecule need not have the same sequence or length (see, for example, Example 1). It is often desirable to generate a nucleic acid molecule that can be ligated to a recipient molecule in only one orientation, or that can be ligated to two different recipient nucleic acid molecules (e.g., a three-way ligation) in a particular arrangement. Accordingly, it is quite valuable to be able to engineer the sequence and length of the 3' overhangs of the inventive product molecule.

As can be seen with reference to FIG. 1, the nature of the ends left by the ribonucleotide-removal treatment can affect the behavior of the product molecule in subsequent ligation reactions. In particular, alkaline hydrolysis of ribonucleotides leaves 5'-OH groups rather than 5'-phosphate groups. As is known in the art, at least one terminal phosphate group is typically required for successful ligation of nucleic acid molecules. Thus, if the product molecule depicted in FIG. 1 is to be ligated to a recipient molecule that lacks the appropriate terminal phosphate groups (e.g., because of exposure to treatment with a phosphatase), it will be desirable to add 5' phosphate groups to the recipient molecule prior to ligation. Any available technique may be utilized to achieve such phosphate group addition; most commonly, the phosphate groups will be added by treatment with polynucleotide kinase.

The product molecules depicted in FIG. 1 may be ligated to any desired recipient molecule. Preferably, the recipient molecule has at least one 3' overhang that is complementary to at least a portion of the at least one 3' overhang on the product molecule. It will be appreciated that, if the recipient molecule has a 3' overhang whose 3' terminal portion is complementary to the 3' terminal portion of the product molecule 3' overhang, but is not otherwise complementary to the product molecule 3' overhang, then one or more gaps will be present after hybridization, which gaps can be filled in with DNA polymerase prior to ligation. Since the sequence and length of the product molecule 3' overhang is selected by the practitioner, this approach may be employed to add sequence to the recombinant molecule that would not be present if complete 3' overhang hybridization had occurred. For the purposes of the present invention, the complementary 3'-terminal portions of the product and recipient molecules should be at least one nucleotide long, and can be 2, 3, 4, 5, 6-10 nucleotides long, or longer. In certain preferred embodiments, the complementary 3'-terminal portions are less than about 6 nucleotides long, so that efficiency of ligation (usually performed at 4° C. or 14° C.) is preserved and complications associated with annealing longer sequences are avoided.

Preferred recipient molecules include, but are not limited to, linearized vectors. Such vectors may be linearized, for example by digestion with a restriction enzyme that produces a 3' overhang complementary to that present on the product molecule. Alternatively, such linearized vectors may be prepared as product molecules as described herein, containing one or more 3' overhangs selected by the practitioner to be compatible with the 3' overhangs present on other product molecules.

Those of ordinary skill in the art will appreciate that product molecules can readily be generated according to the present invention so that each end of a given product molecule has a different 3' overhang. Such molecules can be used in directional cloning experiments, where they can be ligated to one or more other molecules in only a single orientation. Such directional ligation strategies are particularly useful where three or more molecules are desired to be linked to one another. In such multi-component ligation reactions, it is often useful to minimize the possibility of self-ligation by individual molecules, and also to reduce the chance that the molecules will link together with one or more molecule being in an improper orientation.

Product Molecules with 5' Overhangs

Figure 2:
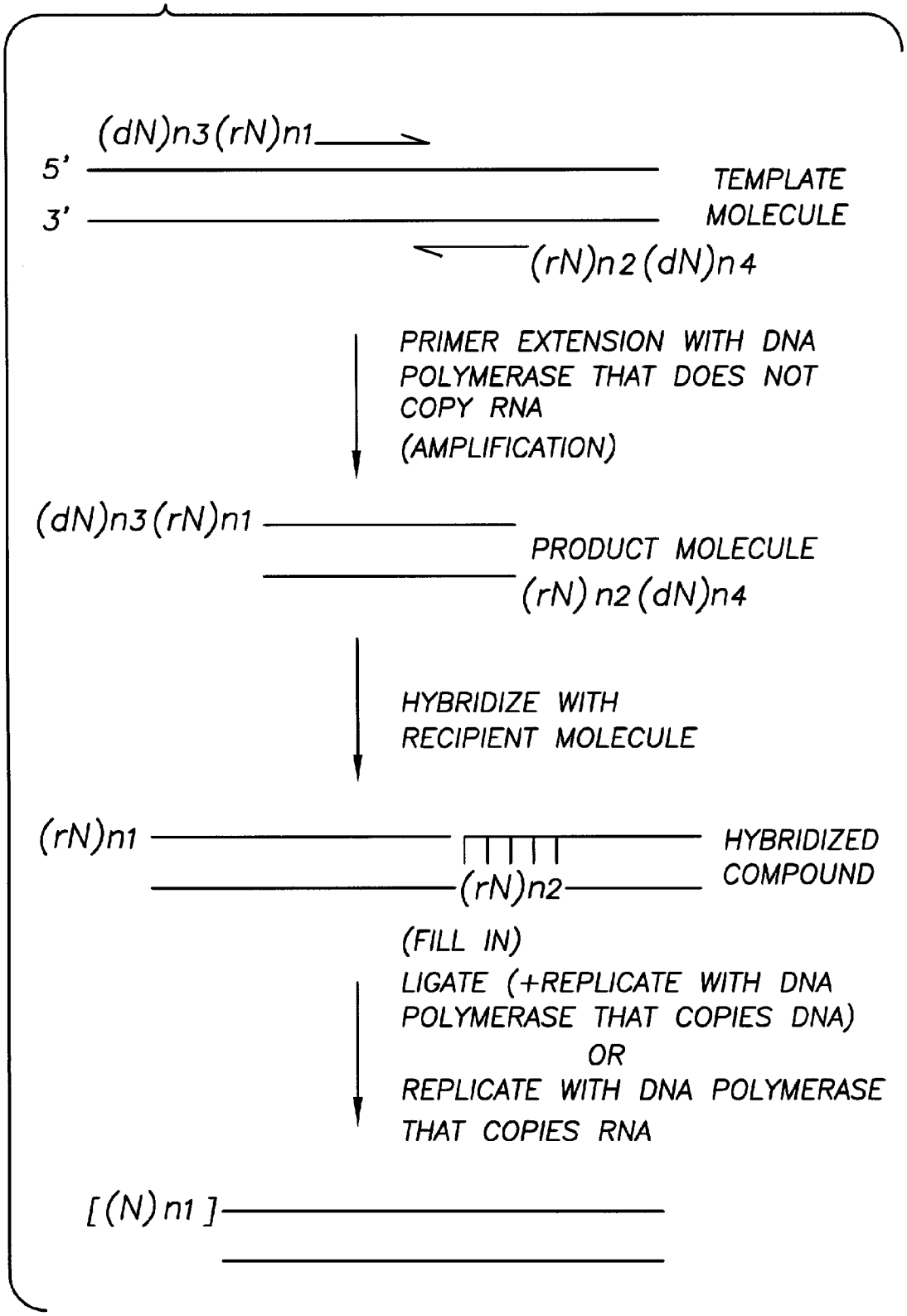
FIG. 2 depicts a process for producing 5' overhangs by hybridizing a template molecule with one or more primers including at least one ribonucleotide primer.
Figure 3:
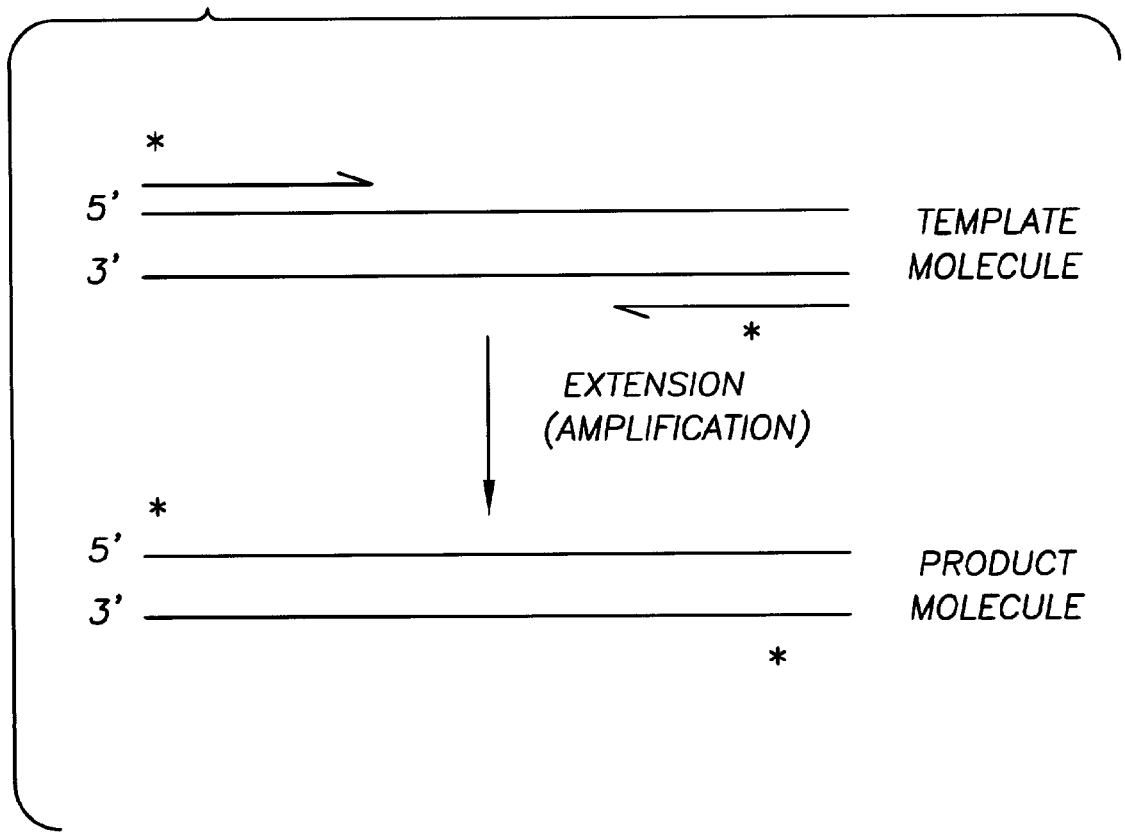
FIG. 3 depicts an inventive process for generating DNA product molecules with one or more 5' overhangs.
Figures 2, 9:
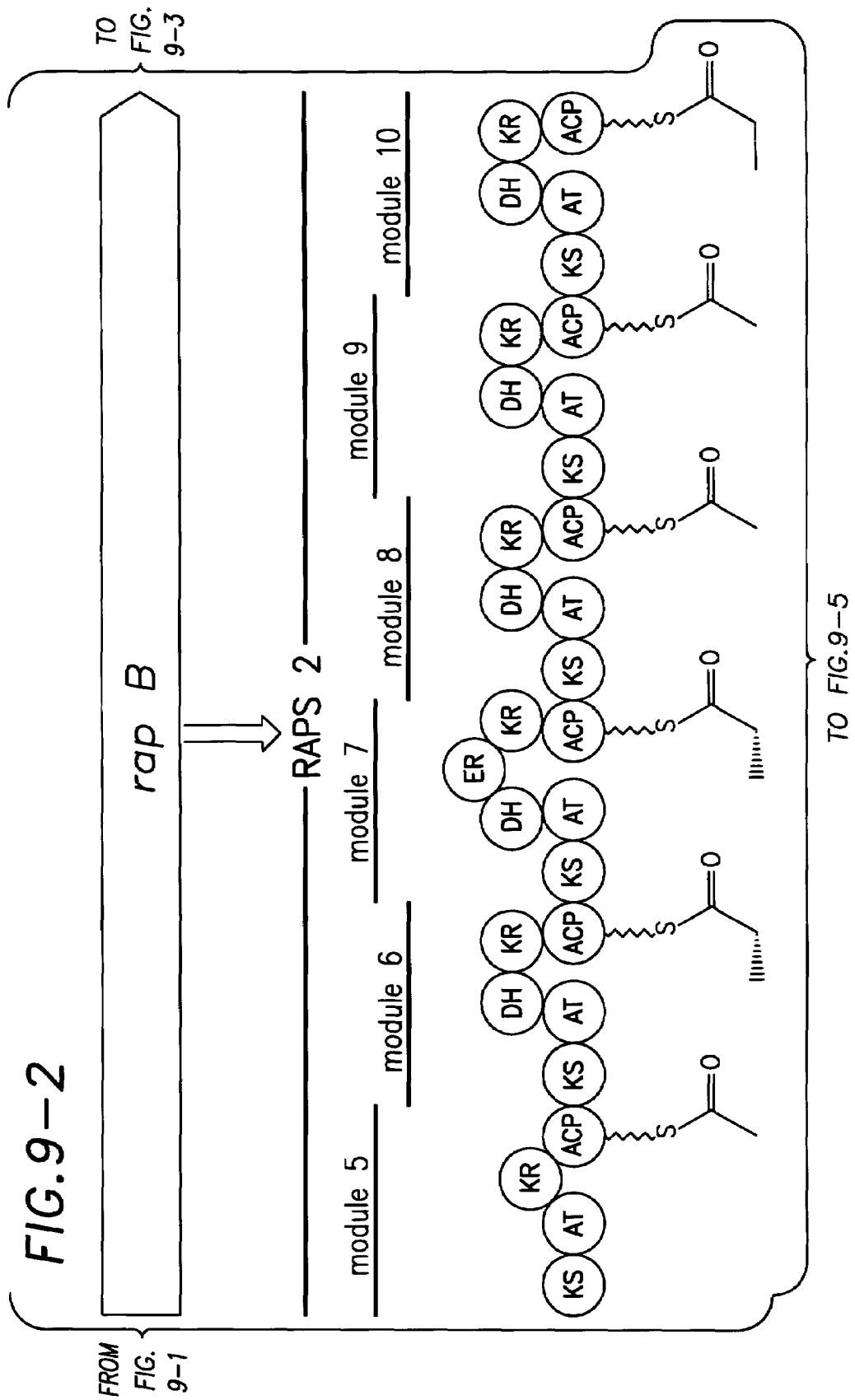
FIG. 9 depicts the different functional domains of bacterial polyketide synthase genes responsible for the production of erythromycin and rapamycin.
Figures 3, 9:
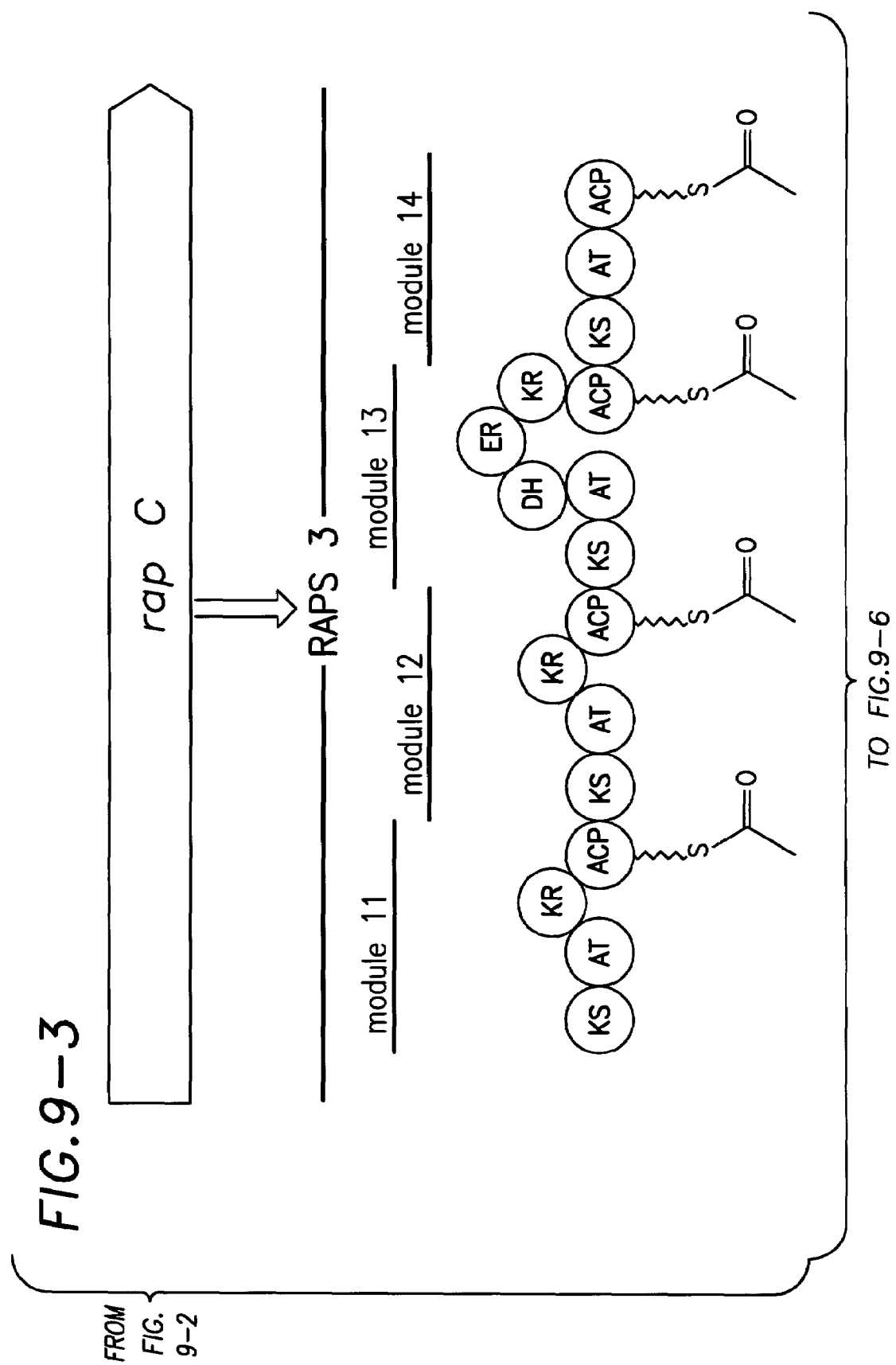
Figures 4, 9:
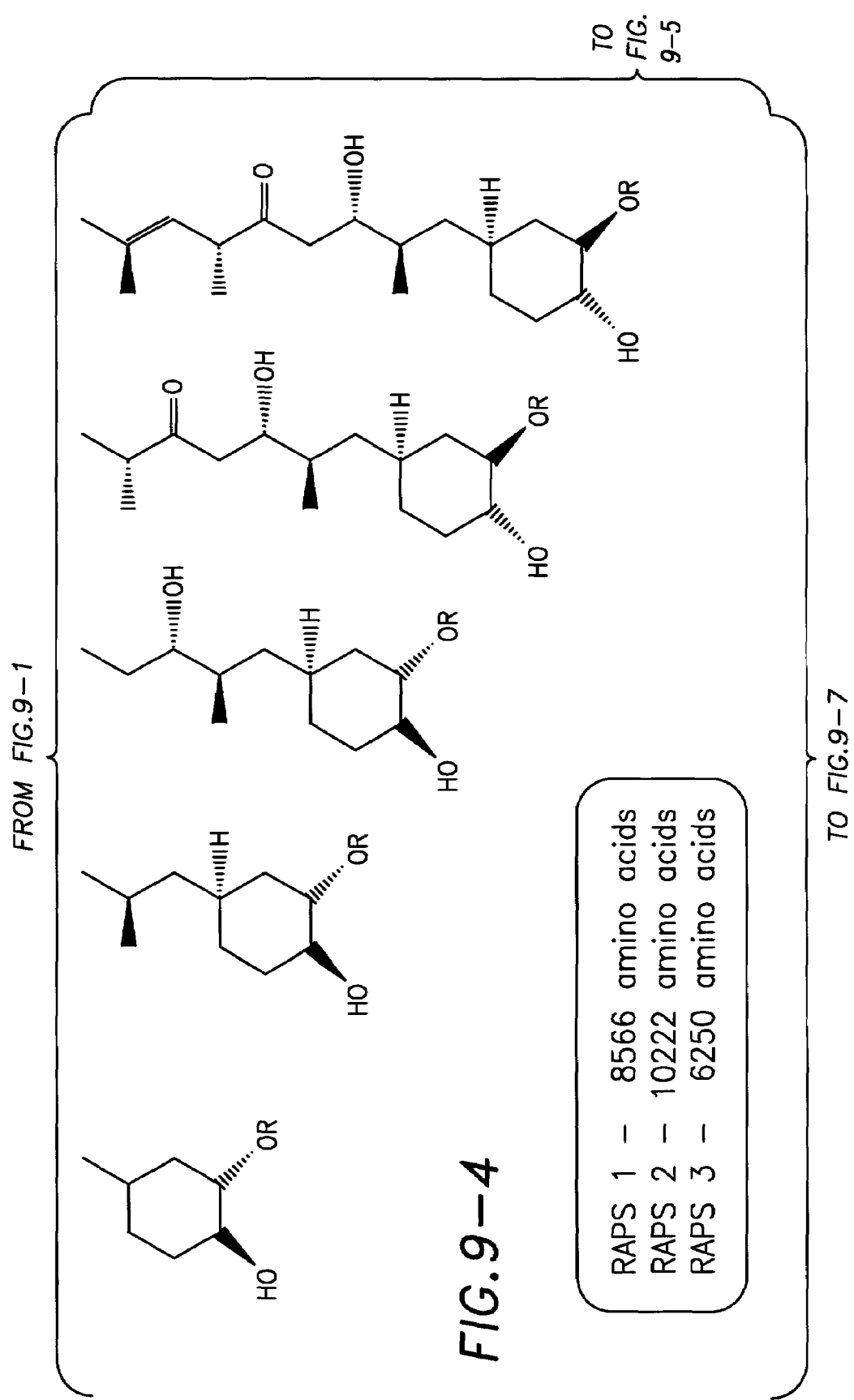

FIGS. 2-4 depict inventive strategies for producing product molecules with 5' overhangs. For example, as shown in FIG. 2, a template molecule may be hybridized with one or more primers including at least one ribonucleotide. For this embodiment of the present invention, it is not required that the ribonucleotide be located at the 5' end of the oligonucleotide, though such is acceptable. The primer may contain 2, 3, 4, 5, 6-10, or more ribonucleotides, and may be wholly ribonucleotides if the DNA polymerase utilized in the extension reaction will extend a ribonucleotide primer. That is, in FIG. 2, at least one of n1 and n2 is a whole number greater than or equal to 1, and n3 and n4 are each a whole number greater than or equal to zero. The particular inventive embodiment depicted in FIG. 3 utilizes two primers. Those of ordinary skill in the art will appreciate that each primer includes a portion, terminating with the 3'-terminal residue of the primer, that hybridizes sufficiently well with the template molecule to allow extension. The sequence of the remainder of the primer, however, need not be complementary to that of the template molecule. Furthermore, those of ordinary skill in the art will also appreciate that if the DNA polymerase being employed includes a 3'→5' exonuclease activity, it is not even essential that the 3'-most residue in the primer hybridize with the template, so long as the exonuclease activity is allowed to chew back to a point in the primer from which extension can occur.

After hybridization with the primer(s), an extension reaction is performed with a DNA polymerase that does not copy ribonucleotides. For example, we have found that Vent$_R$® and Vent$_R$® (exo$^-$) do not use ribonucleotide bases as a template (see Example 1); Tth and Taq polymerases, by contrast, are reported to be able to replicate ribonucleotides (Myers et al., *Biochem.* 6:7661, 1991), as, of course, are reverse transcriptases. Other DNA polymerases may be tested for their ability to copy ribonucleotides according to standard techniques or, for example, as described in Example 3.

The extension reaction shown in FIG. 2 may be iterated as an amplification reaction, if desired. The embodiment depicted in FIG. 2 illustrates such an amplification, from which the product is a double stranded molecule with two 5' overhangs, each of which includes at least one ribonucleotide residue. Those of ordinary skill in the art will appreciate that the sequence and length of each 5' overhang (as well as ribonucleotide composition) is selected by the practitioner, and that the two product molecule overhangs depicted may be the same or different.

This product molecule may then be hybridized with one or more recipient molecules containing a 5' overhang that is complementary to at least the 5'-terminal residue of the product molecule. If gaps remain after hybridization, they may be filled in with DNA polymerase according to known techniques. If the gaps encompass a ribonucleotide residue, it may be preferable to employ a DNA polymerase that will copy RNA in order to ensure that the gap is filled. As mentioned above, such DNA polymerases include, for example, Tth, Taq, and reverse transcriptase. Other DNA polymerases may be tested for their ability to copy RNA according to known techniques or, for example, as described in Example 3.

Once any gaps are filled, the product and recipient molecules may be ligated together. DNA ligase is known to close nicks (i) between adjacent deoxyribonucleotides; (ii) between a deoxyribonucleotide and a ribonucleotide; or (iii) between adjacent ribonucleotides. Thus, a hybrid molecule can be produced containing both DNA and RNA residues. This molecule can be copied into DNA, either in vitro according to standard techniques, or in vivo after introduction in to a host cell capable of copying such a molecule (*Escherichia coli*, for example, have been reported to be able to remove and replace ribonucleotides that are base-paired with deoxyribonucleotides—see Sancar, *Science* 266:1954, 1994). Alternatively, it may be desirable to replicate the hybridized compound into DNA rather than performing a ligation (e.g., by PCR with DNA primers or with a DNA polymerase that can copy ribonucleotides). Also, it should be mentioned that, in some cases, ligation may be accomplished in vivo rather than in vitro, as is known in the art for example for co-transformation of yeast cells.

As depicted in FIG. 2, the product molecule is ligated with only a single recipient molecule and at only one end. Those of ordinary skill in the art will appreciate that a product molecule may alternatively be ligated at both of its ends, either to a single recipient molecule or to two different recipient molecules.

FIG. 3 presents an alternative approach to generating product molecules with one or more 5' overhangs. In this embodiment, instead of employing ribonucleotide primer residues and a DNA polymerase that cannot copy RNA, we utilize a modified base in the primer, which modified base is not copied by the DNA polymerase. A wide variety of modified nucleotides are known in the art (see, for example, U.S. Pat.

No. 5,660,985; see also various catalogs such as that provided by Oligos, Etc. [Bethel, Me.]); those that are not copied by particular DNA polymerases may be identified, for example, by reference to the manufacturer's catalog, by routine screening according to known techniques, or as described, for example, in Example 3.

Modified bases may be removed from the product molecule, before or after its ligation to a recipient molecule, either by DNA replication in vitro or in vivo with a DNA polymerase that will copy the modified base or by removal of the base followed by gap repair, according to standard techniques (see, for example, Sancar, *Science* 266:1954, 1994).

FIG. 4 presents an inventive embodiment for generating a product molecule with at least one 5' overhang. In the particular embodiment depicted in FIG. 4, the inventive strategy is applied to a starting molecule containing one (FIG. 4A) or two (FIG. 4B) 3' overhangs, so that the starting molecule is converted from a 3'-overhang-containing compound to a 5'-overhang-containing molecule. However, those of ordinary skill in the art will appreciate that the same approach could equally well be applied to add one or two 5' overhangs to a starting molecule that is either blunt ended, or contains one or two 3' or 5' overhangs.

Figure 4A:
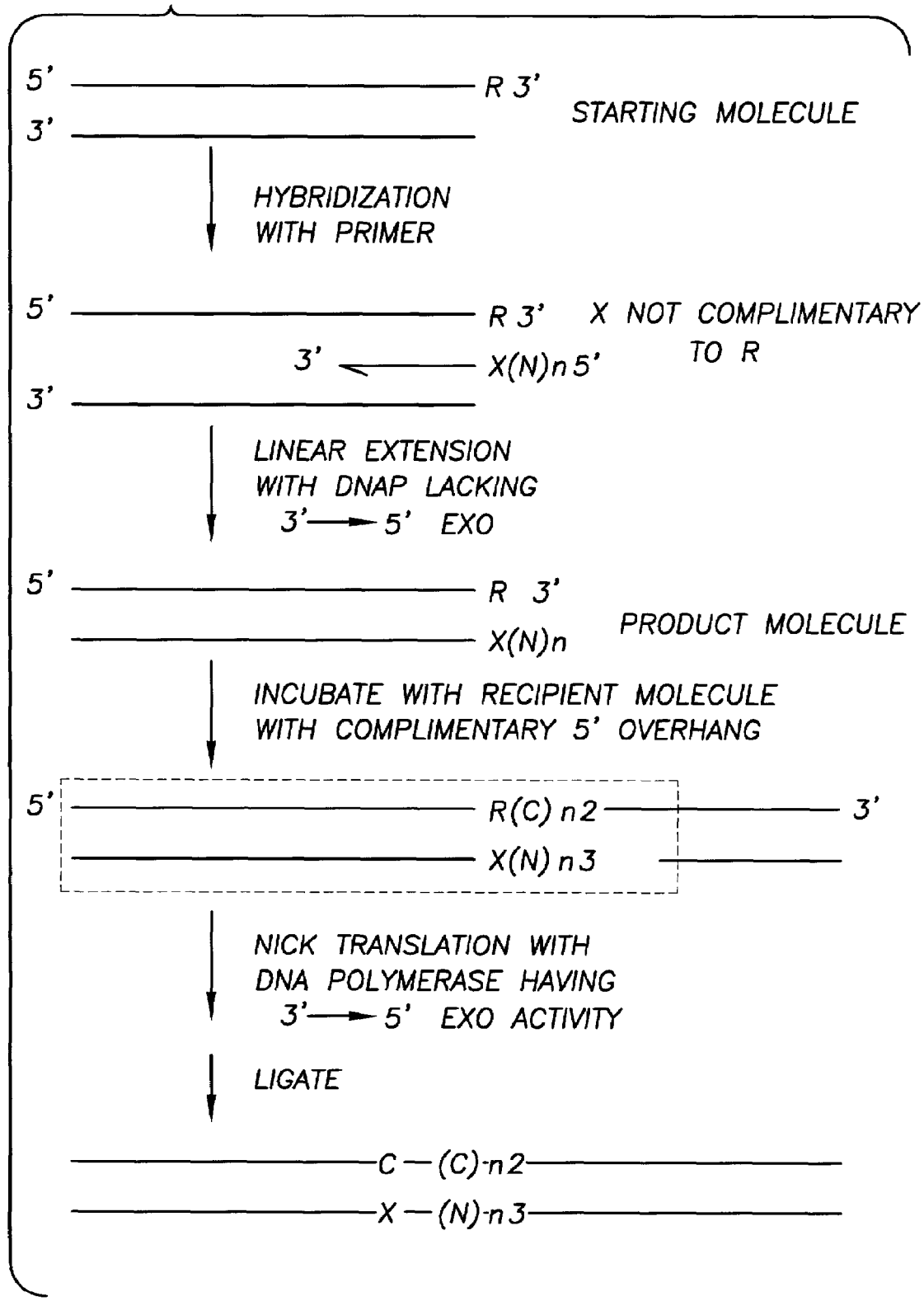
FIG. 4 depicts an alternative inventive process for generating DNA product molecules with one (FIG. 4A) or more (FIG. 4B) 5' overhangs.
Figure 4B:
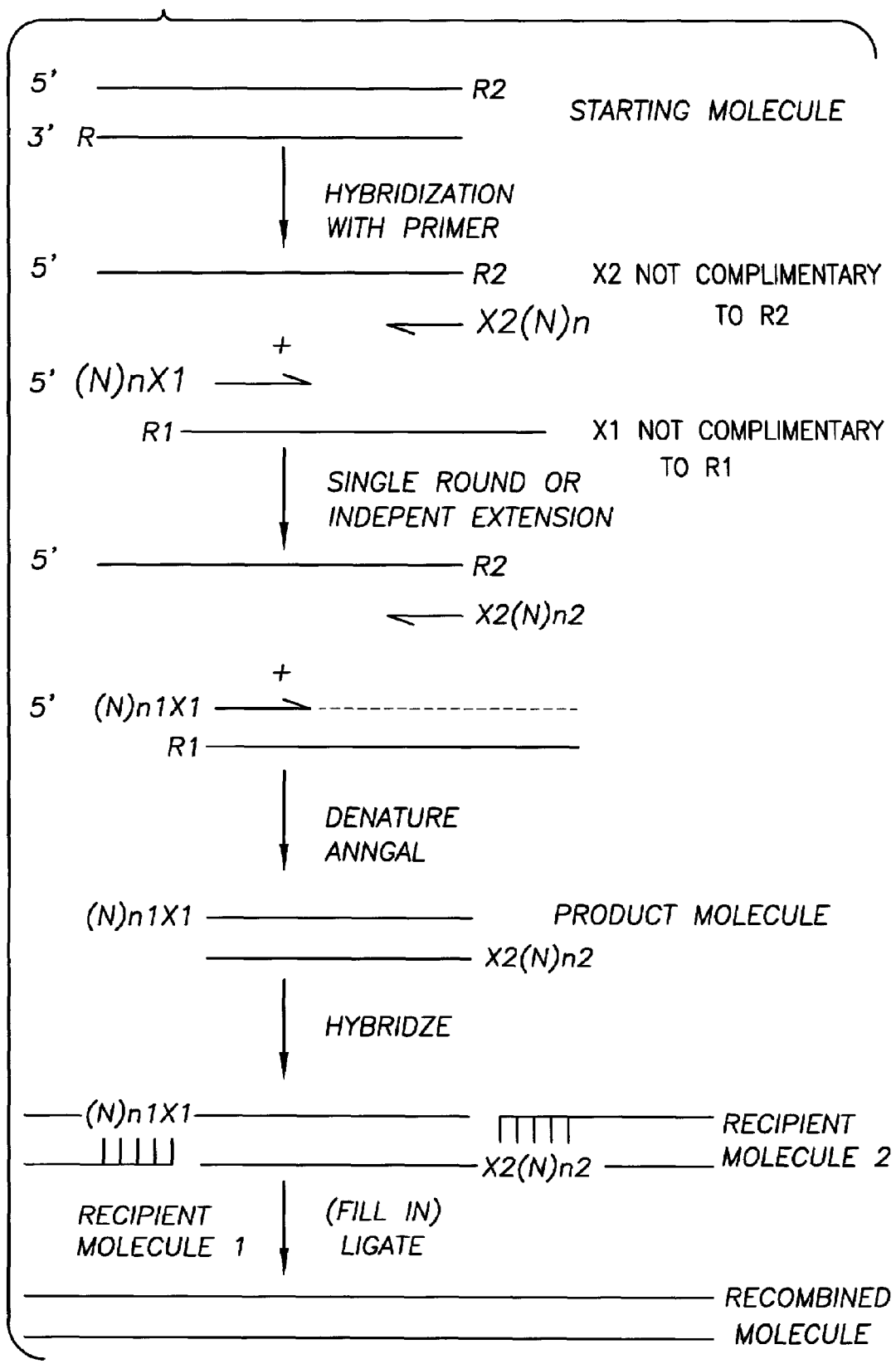

The starting molecule depicted in FIG. 4 may be obtained by any available means. The molecule may have one or two 3' overhangs (meaning that at least one of R1 and R2 is at least one nucleotide long) and may be produced, for example, by restriction endonuclease cleavage of a precursor fragment, by polymerase chain amplification, or by any other means. In certain preferred embodiments of the invention, the starting molecule is produced by PCR and contains a single 3' dATP at each end, as described above. FIG. 4A depicts the application of the inventive method to a starting molecule having only one 3' overhang; FIG. 4B depicts the application of the inventive method to a starting molecule having two 3' overhangs.

With reference to FIG. 4A, the starting molecule is hybridized with at least one primer containing a first portion that hybridizes with a first sequence in the starting molecule that is substantially adjacent to the starting molecule 3' overhang residue, a second portion that aligns with and fails to hybridize to at least one residue of the starting molecule 3' overhang, and a third portion that does not align with the starting molecule but rather extends past (5' in the primer) the last residue of the starting molecule 3' overhang.

The length and sequence of the first portion of the primer is determined by the sequence of the starting molecule adjacent the starting molecule 3' overhang. Hybridization by the first portion of the primer may extend into the 3' overhang, so long as at least one residue of the 3' overhang is aligned with and fails to hybridize with the second portion of the primer. The length and sequence of the second portion of the primer is determined to some degree by the length and sequence of the starting molecule 3' overhang in that the second portion must fail to hybridize with at least one residue of the 3' overhang, preferably but not essentially at least the 3'-terminal residue. So long as such hybridization is avoided, the precise sequence of this second portion of the primer may be selected by the practitioner. The length (i.e., the value of n in FIG. 4A, which must be a whole number greater than or equal to 1) and sequence (i.e., the identities of N in FIG. 4A) of the third portion of the primer is also determined by the practitioner. This third portion will become a 5' overhang in the product molecule.

As depicted in FIG. 4A, single or multiple rounds of extension from the inventive primer is performed. It will be appreciated by those of ordinary skill in the art that, due to the absence of a second primer (and the mismatch between the primer and the starting molecule 3' overhang, which prevents extension of the 3' end of that strand of the starting molecule) only linear, and not exponential, extension is accomplished. Of course, if the DNA polymerase employed in the extension reaction is one that adds one or more terminal 3' residues, the product molecule may have a 3' overhang as well as a 5' overhang.

Once the product molecule with a 5' overhang is produced, it may be hybridized with any recipient molecule that also contains a 5' overhang, at least part of which is complementary to part of the product molecule 5' overhang. The hybridized compound contains a nick on each strand (or may even contain a gap if the 5' overhangs of the product and recipient molecules are imperfectly matched in length) and at least one mismatch immediately prior to the product molecule 5' overhang. This hybridized compound is then exposed to a 3'→5' exonuclease activity to remove the mismatched base(s) (that correspond to the portion of the starting molecule 3' overhang that did not hybridize with the second portion of the primer). The digested compound is then exposed to a DNA polymerase to fill in the gap created by exonuclease digestion, and subsequently to ligase to heal any remaining nicks. Enzymes having 3'→5' exonuclease activity are well known in the art (including, for example, *E. coli* DNA polymerase I, Pfu, Vent$_R$®, Deep Vent$_R$®, etc.); other enzymes may be tested for this ability according to standard techniques.

Those of ordinary skill in the art will appreciate that the method depicted in FIG. 4A may be applied to either strand of a starting molecule, depending on where the 3' overhang is located. As depicted in FIG. 4B, the method may even be applied to both strands simultaneously, although it is important for such an embodiment to perform only a single round extension reaction or to perform independent extension reactions for each strand. Amplification (i.e., multiple rounds of denaturation and extension) is not performed because such amplification would result in the production of a blunt-ended molecule (or one with 3' overhangs if a DNA polymerase that adds 3' nucleotides were employed), having the sequence dictated by the primers, rather than a molecule with a 5' overhang and a mismatch immediately 3' of the 5' overhang.

As shown in FIG. 4B, a starting molecule containing two 3' overhangs is converted to a product molecule containing two 5' overhangs by application of the inventive method. The starting molecule is hybridized with two inventive primers containing first, second, and third portions as described above in the discussion of FIG. 4A. Each primer is then extended in single-round (or independent) extension reactions. It will be understood by those of ordinary skill in the art that both extension reactions need not be performed simultaneously, or on the same exact starting molecule. Extensions of each primer can even be performed in different reaction vesicles.

Each of the double-stranded molecules produced in the extension reaction has a single 5' overhang, whose sequence and length corresponds to that of the third primer portion. The strands of these double stranded molecules are then separated from one another. Individual strands may be separately purified if desired, but such is not required. Strands are then mixed together (if they are not already together) and annealed, so that the two new strands synthesized by extension of the primers have the opportunity to anneal to one another. The product of this annealing reaction is an inventive product molecule with two 5' overhangs. As will be appreciated, these overhangs may be the same or different in length and/or sequence.

This product molecule may be hybridized with one or more recipient molecules, each of which has a 5' overhang whose 5'-terminal portion (at least one nucleotide in length) is complementary with a 5'-terminal portion (of the same length) of the product molecule 5' overhang. Any gaps remaining after hybridization may be filled in with a DNA polymerase; the product and recipient molecules may then be ligated together.

Blunt-ended Product Molecules

Figures 5, 9:
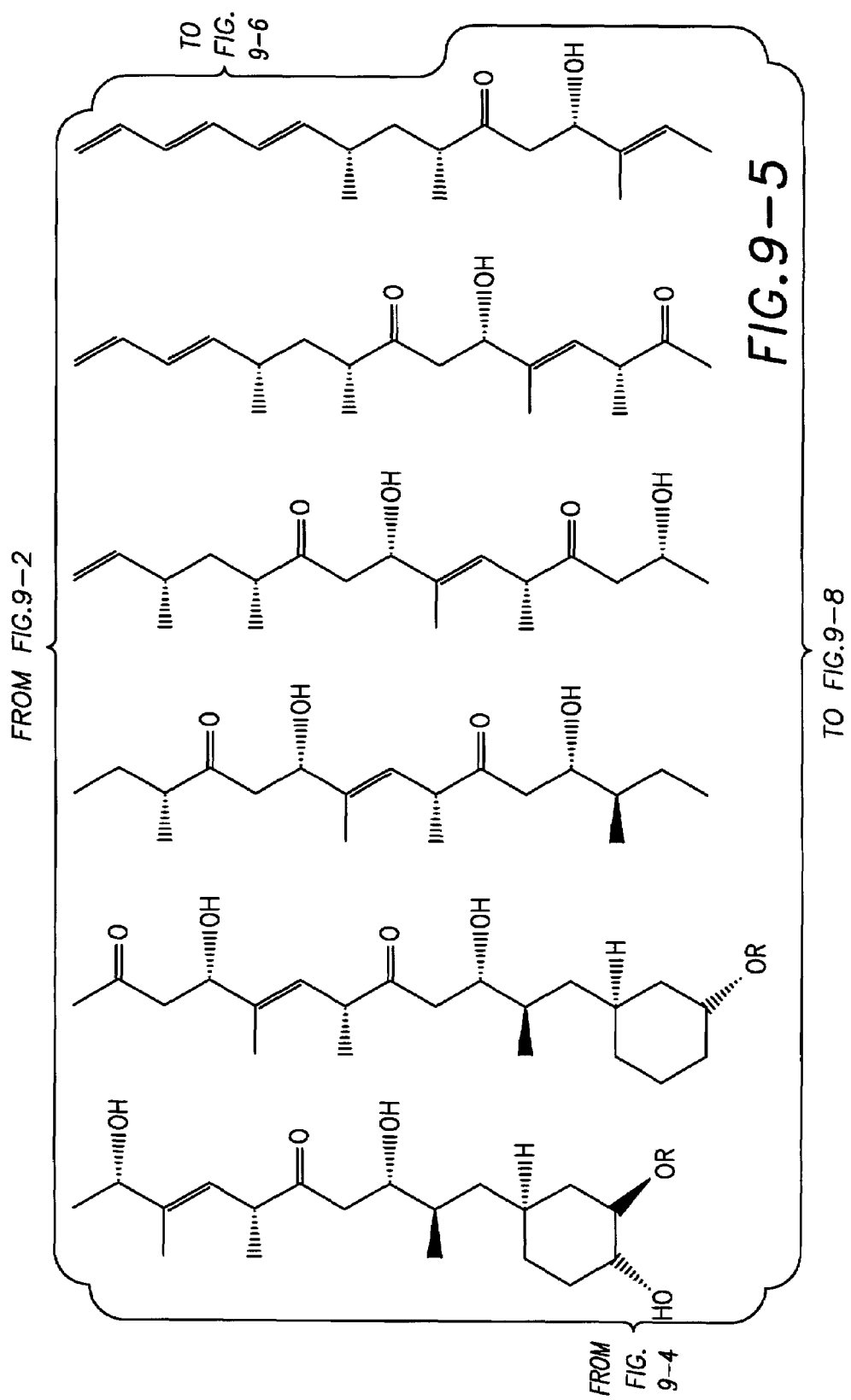
FIG. 5 presents a process that allows ligation of blunt-ended molecules.
Figures 6, 9:
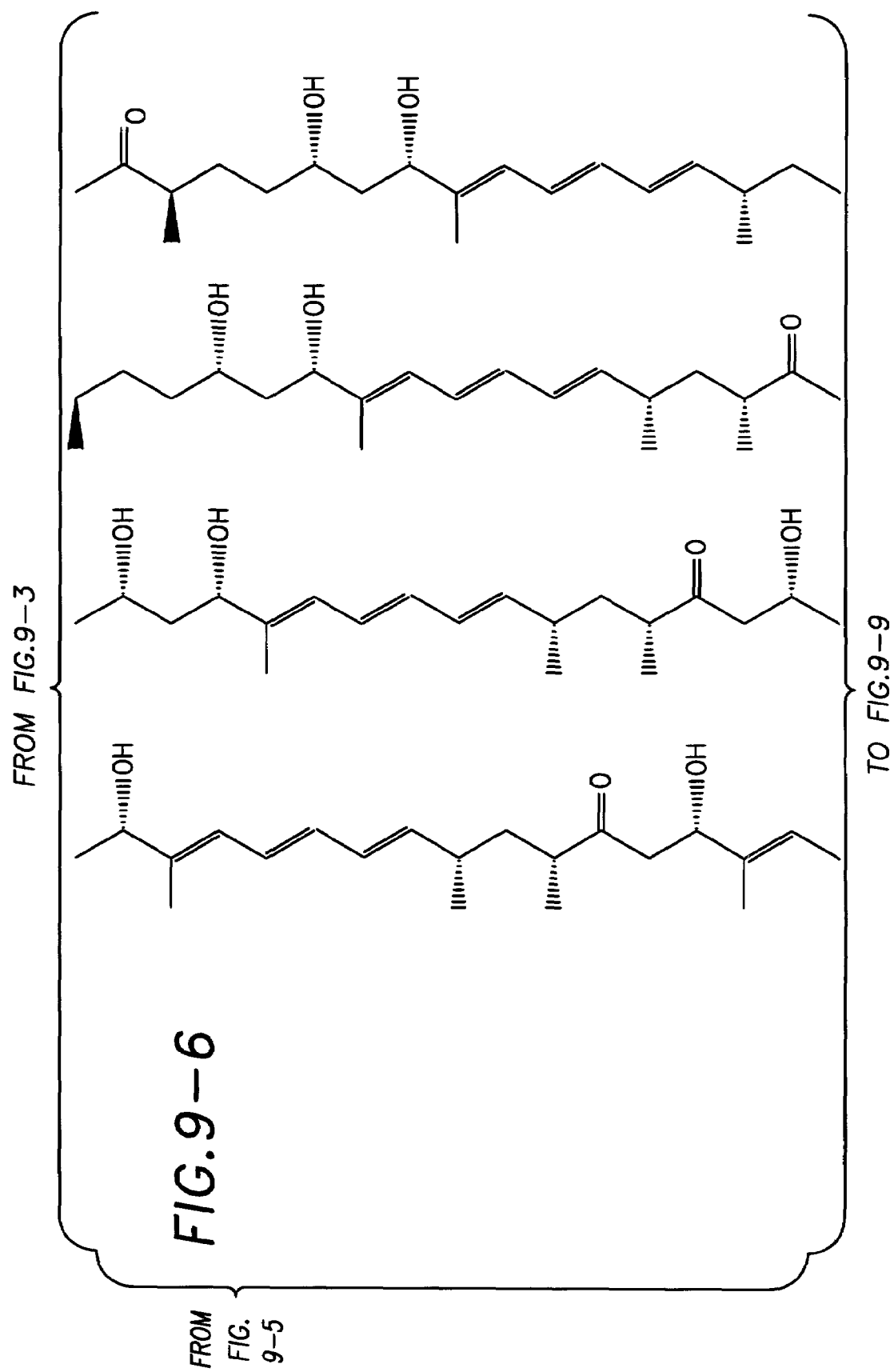

FIG. 5 presents an inventive embodiment that allows ligation of blunt-ended molecules. As shown, blunt ended starting molecules are provided that are to be linked together. Such molecules may be prepared by any available technique including, for example, digestion of a precursor with one or more restriction enzymes (optionally followed by a fill-in or chew-back of any overhanging ends), PCR (e.g., with a DNA polymerase that does not add extraneous 3' nucleotides—reference can be made to manufacturer's catalogs to determine the characteristics of a particular DNA polymerase. For example, $Vent_R$® is reported to generate>95% blunt ends; $Vent_R$® (exo⁻) is reported to generate about 70% blunt ends and 30% single nucleotide 3' overhangs, of any nucleotide; Pfu is reported to produce only blunt-ended molecules), chemical synthesis, etc. The starting molecules may be double stranded or single stranded. As depicted in FIG. 5, the starting molecules are double stranded.

The starting molecules are hybridized to bridging molecules, each of which hybridizes to at least one terminal residue of two different starting molecules that are to be linked together. Clearly, if the starting molecules are double stranded, they should be denatured prior to exposure to the bridging molecules, so that successful hybridization with the bridging molecules may occur. The bridging molecules may hybridize to more than one residue of each starting molecule, and/or may contain non-hybridizing portions between the portions that hybridize to the two starting molecules. Also, the bridging molecules may have sufficient length that they abut one another after hybridization, or may be short enough that gaps are present in the hybridized compound between the individual bridging molecules. Preferably, at least one primer hybridizes to the 3'-terminus of the 3'-most starting molecule in the hybridized compound. This primer may extend past the terminus if desired, so that a 5' overhang is created. No such overhang is depicted in FIG. 5.

The hybridized compound is then converted into a double-stranded DNA molecule by any collection of available techniques. For example, gaps may be filled with DNA polymerase and any remaining nicks sealed with DNA ligase. Or, if no gaps are present in one strand, that strand may first be ligated and DNA polymerase subsequently applied, in vitro or in vivo to seal gaps in the other strand or to synthesize a replacement strand (e.g., primed from the bridging molecule hybridized at the most 3' location with respect to the starting molecules). In one preferred embodiment of the invention, gaps are filled and nicks sealed and the entire recombinant molecule is then replicated by PCR amplification. If desired, a DNA polymerase that adds one or more 3'-terminal residues may be employed, so that the resultant amplified product is likely to have one or more 3' overhangs. As described above, such a product may readily be ligated to another molecule with complementary 3' overhangs, such as occurs in the use of the Invitrogen TA Cloning Kit® system.

Applications

The product molecules and ligation strategies provided above are useful in any of a variety of contexts. For the purposes of clarification only, and not for limitation, we discuss certain of these contexts in more detail here.

As described above, the present invention produced techniques and reagents for providing nucleic acid molecules that can be directly ligated (i.e., without first being digested with a restriction enzyme) to other molecules. The invention also provides techniques for accomplishing such ligation. The present invention may be used to link nucleic acid molecules of any sequence to one another and therefore has the broadest possible application in the field of genetic cloning.

Those of ordinary skill in the art will appreciate that the inventive techniques and reagents may be employed to link any DNA molecule to any other DNA molecule, regardless of the particular sequences of the DNA molecules, their protein-coding capacities, or any other characteristics. This feature distinguishes the present system from traditional, restriction-endonuclease-reliant cloning systems, for which the precise sequences of the molecules being linked can often affect the design of the cloning strategy, as it may be desirable, for example, to avoid cleaving one fragment with a particular enzyme that produces an undesired cleavage in another fragment, or to make other adjustments to accommodate the behavior of the protein enzymes being employed.

Production of Protein-coding Genes

In certain preferred embodiments of the present invention, one or more of the DNA molecules included in an inventive ligation reaction includes open reading frame, i.e., a protein-coding sequence. In particularly preferred embodiments, at least two DNA molecules to be ligated together include open reading frame sequences, and their ligation produces a hybrid DNA containing both open reading frames linked together so that a single polypeptide is encoded. Where ligation of two or more DNA molecules, according to the present invention, generates at least one open reading frame that spans at least one ligation junction, the ligation is considered to have generated a new, hybrid protein-coding gene.

In but one embodiment of the inventive system used to produce protein-coding genes, the DNA molecules to be ligated to one another are selected to encode one or more discrete functional domains of known biological activity, so that the ligation of two or more such DNA molecules produces a hybrid gene encoding a bi- or multi-functional polypeptide. It is well known in the art that many proteins have discrete functional domains (see, for example, Traut, Mol. Cell. Biochem. 70:3, 1986; Go et al., Adv. Biophys. 19:91, 1985). It is also well known that such domains may often be separated from one another and ligated with other discrete functional domains in a manner that preserves the activity of each individual functional domain.

Those of ordinary skill in the art will appreciate that some flexibility is allowed in the selection of precise DNA sequences encoding functional protein domains. For example, it is often not desirable to limit the DNA sequences to only those that encode for exactly the amino acid residues contained in a functional domain of a naturally-occurring protein. Additional DNA sequences may be included, for example, encoding linker sequences that can provide flexibility between the particular selected functional domain and any other functional domain to which it is to be linked.

Alternatively or additionally, in some contexts researchers have found that it is useful to select DNA sequences encoding less than all of the amino acids comprising a particular functional domain (see, for example, WO 98/01546); in such cases, the other amino acids can be added back as a result of the subsequent ligation (i.e., can be encoded by an adjacently-ligated DNA molecule), or can be left out completely. Those of ordinary skill in the art will readily be able to familiarize themselves with the application of these basic principles to their particular experimental question after appropriate consultation with the literature describing the protein domains in which they are interested.

To give but a few examples of the types of functional protein domains that could be encoded by individual DNA molecules, or combinations of DNA molecules, to be ligated according to the present invention, well known modular domains include, for example DNA binding domains (such as zinc fingers, homeodomains, helix-turn-helix motifs, etc.), ATP or GTP binding domains, transmembrane spanning domains, protein-protein interaction domains (such as leucine sippers, TPR repeats, WD repeats, STYX domains [see, for example, Wishart et al., *Trends Biochem. Sci.* 23:301, 1998], etc.), G-protein domains, tyrosine kinase domains (see, for example, Shokat, *Chem. Biol.* 2:509, 1995), SRC homology domains (see, for example, Sudol, *Oncogene* 17:1469, 1998), SH2 domains (see, for example, Schaffhausen, *Biochim. Biophys. Acta* 28:61, 1995), PTB domains (see, for example, van der Greer et al., *Trends Biochem Sci* 20:277, 2995), the PH domain (see, for example, Musacchio et al., *Trends Biochem Scie* 18:343, 1993), certain catalytic domains, cell surface receptor domains (see, for example, Campbell et al., *Immunol. Rev.* 163:11, 1998), carbohydrate recognition domains (see, for example, Kishore et al., *Matrix Biol.* 15:583, 1997), immunoglobulin domains (see, for example, Rapley, *Mol. Biotechnol.* 3:139, 1995), etc. (see also, Hegyi et al., *J. Protein. Chem.* 16:545, 1997; Baron et al., *Trends Biochem. Sci.* 16:13, 1997).

Typically, such domains are identified by homology comparisons that identify regions of sequence similarity within proteins of known biological activity (at least as relates to the portion of the protein showing the homology). The spatial coherence of any particular functional domain is often confirmed by structural studies such as X-ray crystallography, NMR, etc.

According to the present invention, a useful "functional domain" of a protein is any portion of that protein that has a known biological activity that is preserved with the portion is separated from the rest of the protein, even if the portion must continue to be embedded within a larger polypeptide molecule in order to maintain its activity. The relevant biological activity need not, and typically will not, constitute the complete biological activity of a particular protein in which the domain is naturally found, but rather will usually represent only a portion of that activity (e.g., will represent an ability to bind to a particular other molecule but will not include a further activity to cleave or modify the bound molecule). As noted, many such domains have already been described in the literature; others can be identified by homology search, preferably in combination with mutational studies as is known in the art to define sequences that participate in biological activity.

The present invention encompasses the recognition, now virtually universally accepted, that the production of new genes during evolution has often involved the novel combination of DNA sequences encoding two or more already-existing functional protein domains (see, for example, Gilbert et al., *Proc Natl Acad Sci USA,* 94:7698, 1997; Strelets, et al., *Biosystems,* 36:37, 1995). In fact, protein "families" are often defined by their common employment of particular functional domains, even though the overall biological roles played by different family members may be quite unrelated (see further discussion of such families below, in section discussing exon shuffling). The present invention therefore provides techniques and reagents that can be used to mimic an evolutionary process in the laboratory. The universality and experimental simplicity of the system provide researchers, who may select particular DNA modules to link to one another in desired orders, with significant advantages over Mother Nature, who must wait for stochastic processes to produce interesting new results.

Figure 6:
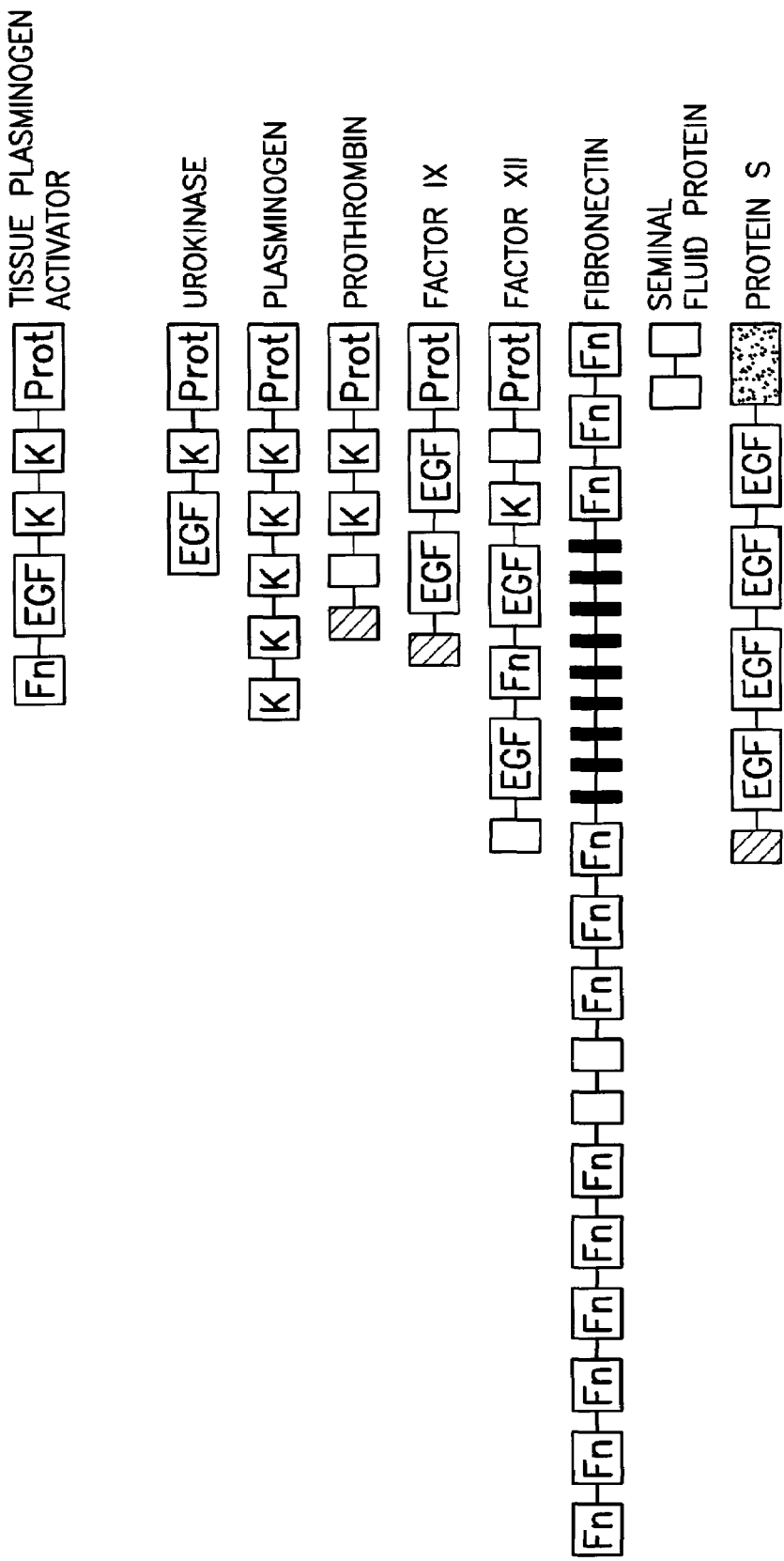
FIG. 6 shows members of the tissue plasminogen activator gene family.

Accordingly, preferred protein functional domains to be employed in accordance with the present invention include those that have been re-used through evolution to generate gene families (i.e., collections of genes that encode different members of protein families). Exemplary gene families created by re-use of particular protein domains include, for example, the tissue plasminogen activator gene family (see, for example FIG. 6); the family of voltage-gated sodium channels (see, for example, Marban et al., *J. Physiol.* 508:647, 1998); certain families of adhesion molecules (see, for example, Taylor et al., *Curr. Top. Microbiol. Imunol.* 228:135, 1998); various extracellular domain protein families (see, for example, Engel, *Matrix Biol.* 15:295, 1996; Bork, *FEBS Lett.* 307:49, 1992; Engel, *Curr. Opin. Cell. Biol.* 3:779, 1991); the protein kinase C family (see, for example, Dekker et al., *Curr. Op. Struct. Biol.* 5:396, 1995); the tumor necrosis factor receptor superfamily (see, for example, Naismith et al., *J. Inflamm* 47:1, 1995); the lysin family (see, for example, Lopez et al., *Microb. Drug Resist.* 3:199, 1997); the nuclear hormone receptor gene superfamily (see, for example, Ribeiro et al., *Annu. Rev. Med.* 46:443, 1995; Carson-Jurica et al., *Endocr. Rev.* 11:201, 1990); the neurexin family (see, for example, Missler et al., *J. Neurochem.* 71:1339, 1998); the thioredoxin gene family (see, for example, Sahrawy et al., *J. Mol. Evol.,* 42:422, 1996); the phosphoryl transfer protein family (see, for example, Reizer et al., *Curr. Op. Struct. Biol.* 7:407, 1997); the cell wall hydrolase family (see, for example, Hazlewood et al., *Prog. Nuc. Acid Res. Mol. Biol.* 61:211, 1998); as well as certain families of synthetic proteins (e.g., fatty acid synthases, polyketide synthases [see, for example, WO 98/01546; U.S. Pat. No. 5,252,474; U.S. Pat. No. 5,098, 837; EP Patent Application Number 791,655; EP Patent Application Number 791,656], peptide synthetases [see, for example, Mootz et al., *Curr. Op. Chem. Biol.* 1:543, 1997; Stachelhaus et al., *FEMS Microbiol. Lett* 125:3, 1995], and terpene synthases).

The present invention allows DNA molecules encoding different functional domains present in these families to be linked to one another to generate in-frame fusions, so that hybrid genes are produced that encode polypeptides containing different arrangements of the selected functional domains. It will be appreciated that experiments can be performed in which (i) only the domains utilized in a particular gene family in nature are linked to one another (in new arrangements), or in which (ii) domains naturally utilized in different gene families are linked to one another.

In one particularly preferred embodiment of the present invention, the DNA modules selected to be ligated together comprise modules encoding at least one functional domain, or portion of a functional domain, of a member of a synthetic enzyme family. As mentioned above, a variety of enzyme families are known whose members are responsible for the synthesis of related biologically active compounds. Families of particular interest include the fatty acid synthase family, the polyketide synthase family, the peptide synthetase family, and the terpene synthase family (sometimes called the terpenoid synthase family, or the isoprenoid synthase family). The individual members of these enzyme families are multi-domain proteins that catalyze the synthesis of particular biologically active chemical compounds. For any particular family member, different protein domains catalyze different steps in the overall synthesis reaction. Each family member catalyzes the synthesis of a different chemical compound because each contains a different collection or arrangement of protein functional domains. As will be understood in the context of the present application, the instant invention provides a system by which the various protein domains utilized in these gene families may be linked to one another in new ways, to generate novel synthase enzymes that will catalyze the production of new chemical entities expected to have biological activities related to those produced by naturally-occurring members of the gene family from which the functional domains were selected.

In order to more clearly exemplify this aspect of the present invention, we discuss below certain characteristics and attributes of each of the above-mentioned particularly preferred synthetic enzyme protein families:

Animal Fatty Acid Synthase Family

The aminal fatty acid synthase comprises two multifunctional polypeptide chains, each of which contains seven discrete functional domains. Fatty acid molecules are synthesized at the interface between the two polypeptide chains, in a reaction that involves the iterative condensation of an acetyl moiety with successive malonyl moieties (see, for example, Smith, *FASEB J.* 8:1248, 1994; Wakil, *Biochemistry* 28:4523, 1989, each of which is incorporated herein by reference). Most commonly, the β-keto intermediate produced in this condensation reaction is completely reduced to produce palmitic acid; in certain instances, however, alternative substrates or alternative chain-terminating mechanisms are employed so that a range of products, including branched-chain, odd carbon-numbered, and shorter-chain-length fatty acid molecules. These molecules have a range of roles in biological systems, including (i) acting as precursors in the production of a variety of singalling molecules, such as steroids, as well as (ii) participating in the regulation of cholesterol metabolism.

Those of ordinary skill in the art, considering the present disclosure, will readily recognize that the techniques and reagents described herein can desirably be applied to DNA molecules encoding one or more of the functional domains of a fatty acid synthase molecule, so that the molecules may be linked to other DNA molecules to create interesting new hybrid DNAs, preferably encoding hybrid animal fatty acid synthase genes that may have novel synthetic capabilities.

Polyketide Synthase Family

Figures 7, 9:
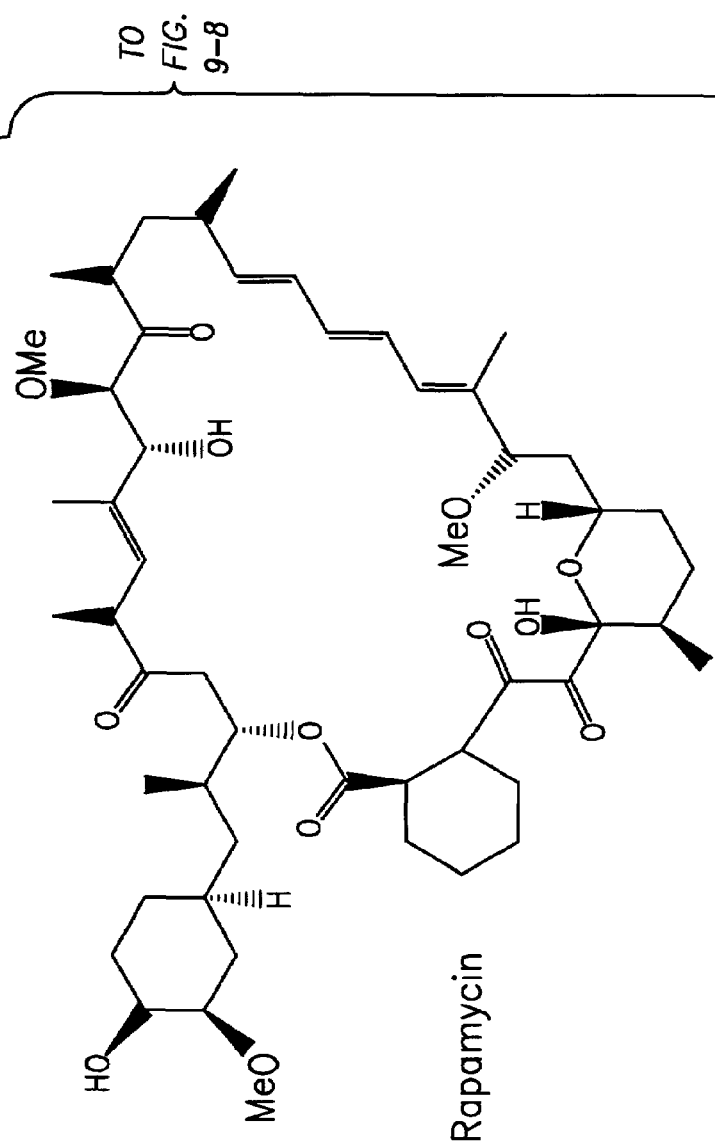
FIG. 7 presents a list of certain polyketide compounds that are currently used as pharmaceutical drugs for the treatment of human and animal disorders.
Figure 9:
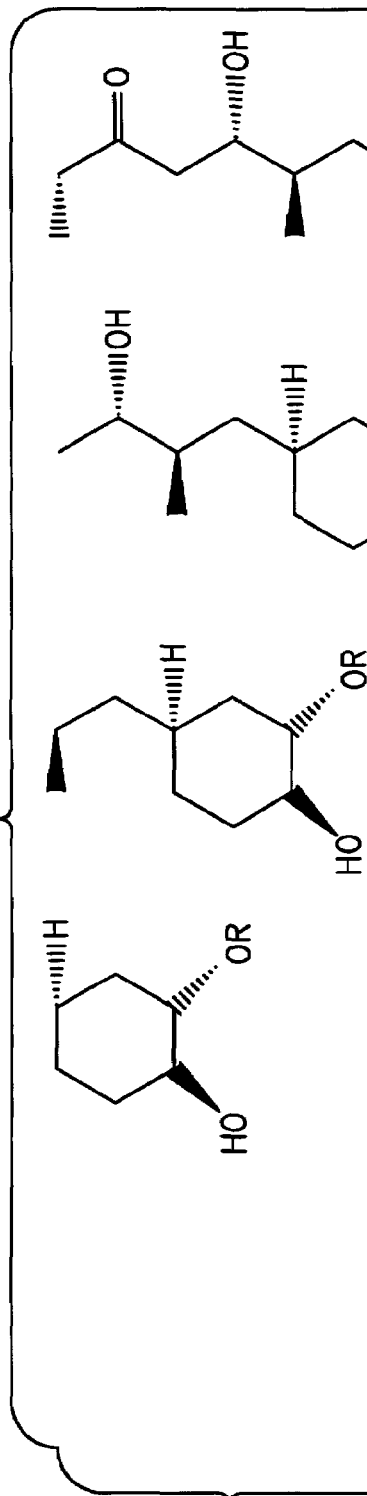
Figure 8:
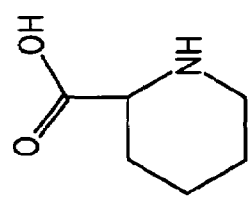
Figure 9:
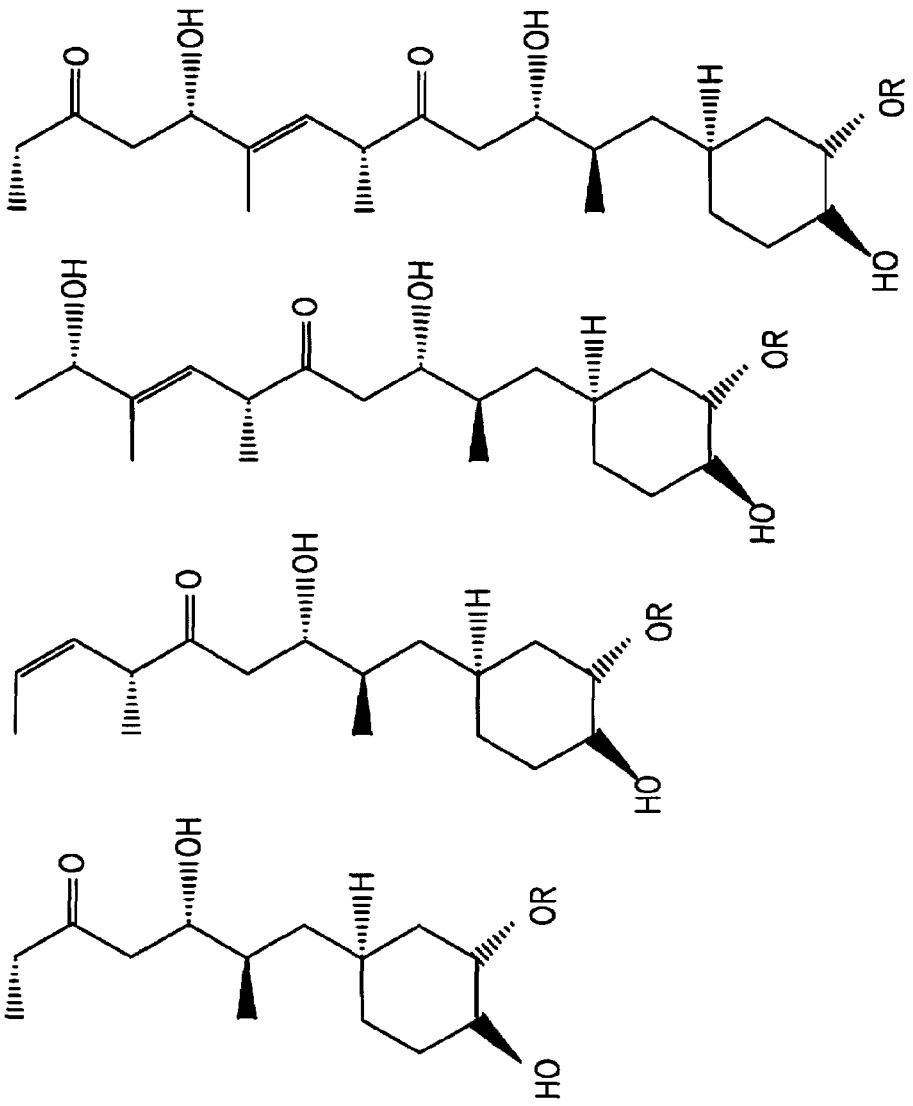

Polyketides represent a large and structurally diverse class of natural products that includes many important antibiotic, antifungal, anticancer, antihelminthic, and immunosuppressant compounds such as erythromycins, tetracylcines, amphotericins, daunorubicins, avermectins, and rapamycins. For example, FIG. 7 presents a list of certain polyketide compounds that are currently used as pharmaceutical drugs in the treatment of human and animal disorders.

Polyketides are synthesized by protein enzymes, aptly named polyketide synthases, that catalyze the repeated stepwise condensation of acylthioesters in a manner somewhat analogous to that employed by the fatty acid synthases. Structural diversity among polyketides is generated both through the selection of particular "starter" or "extender" units (usually acetate or proprionate units) employed in the condensation reactions, and through differing degrees of processing of the β-keto groups observed after condensation. For example, some β-keto groups are reduced to β-hydroxyacyl-groups; others are both reduced to this point, and are subsequently dehydrated to 2-enoyl groups; still others are reduced all the way to the saturated acylthioester.

Figures 1, 8:
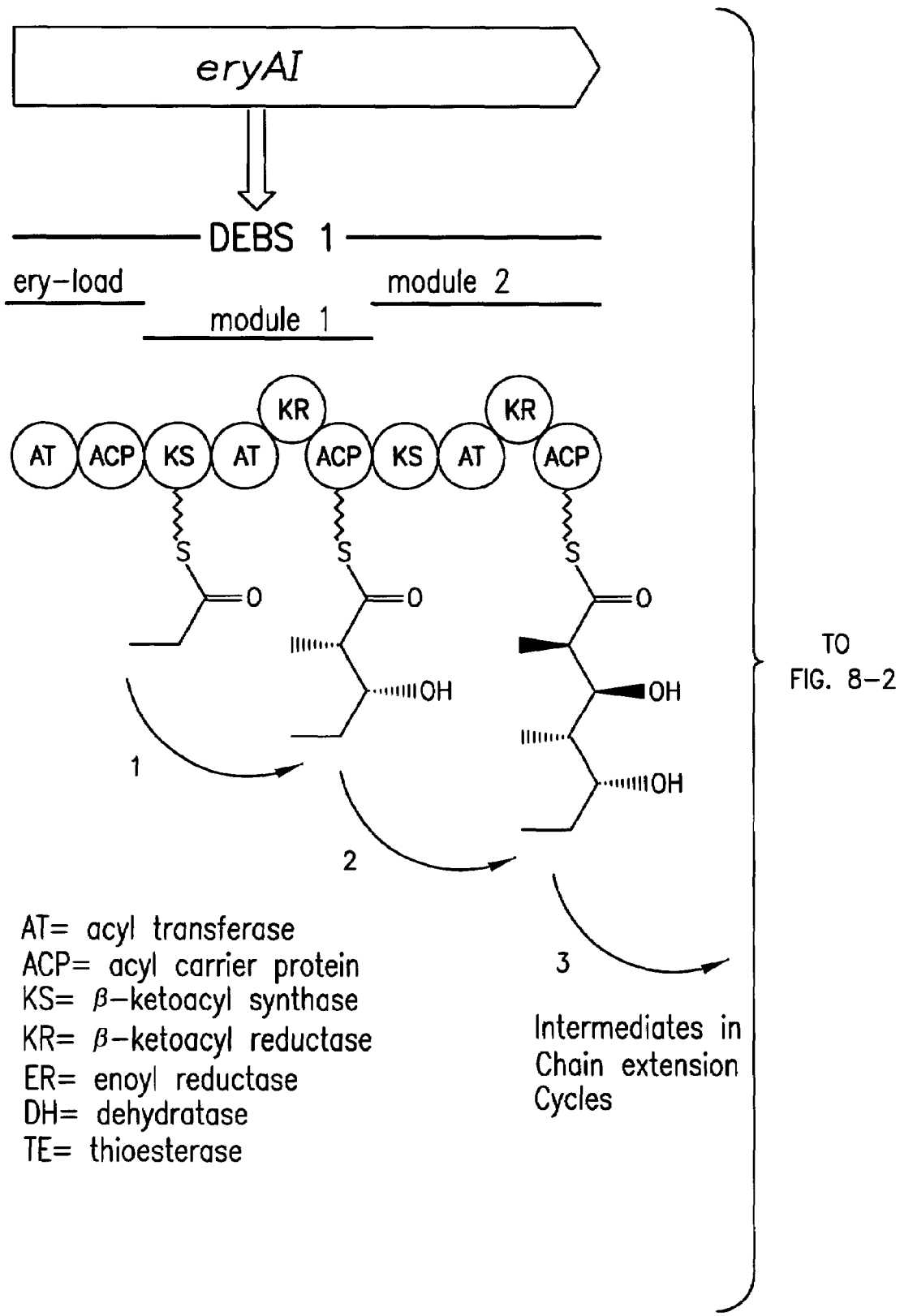
FIG. 8 depicts the different functional domains of bacterial polyketide synthase genes responsible for the production of erythromycin and rapamycin.
Figures 2, 8:
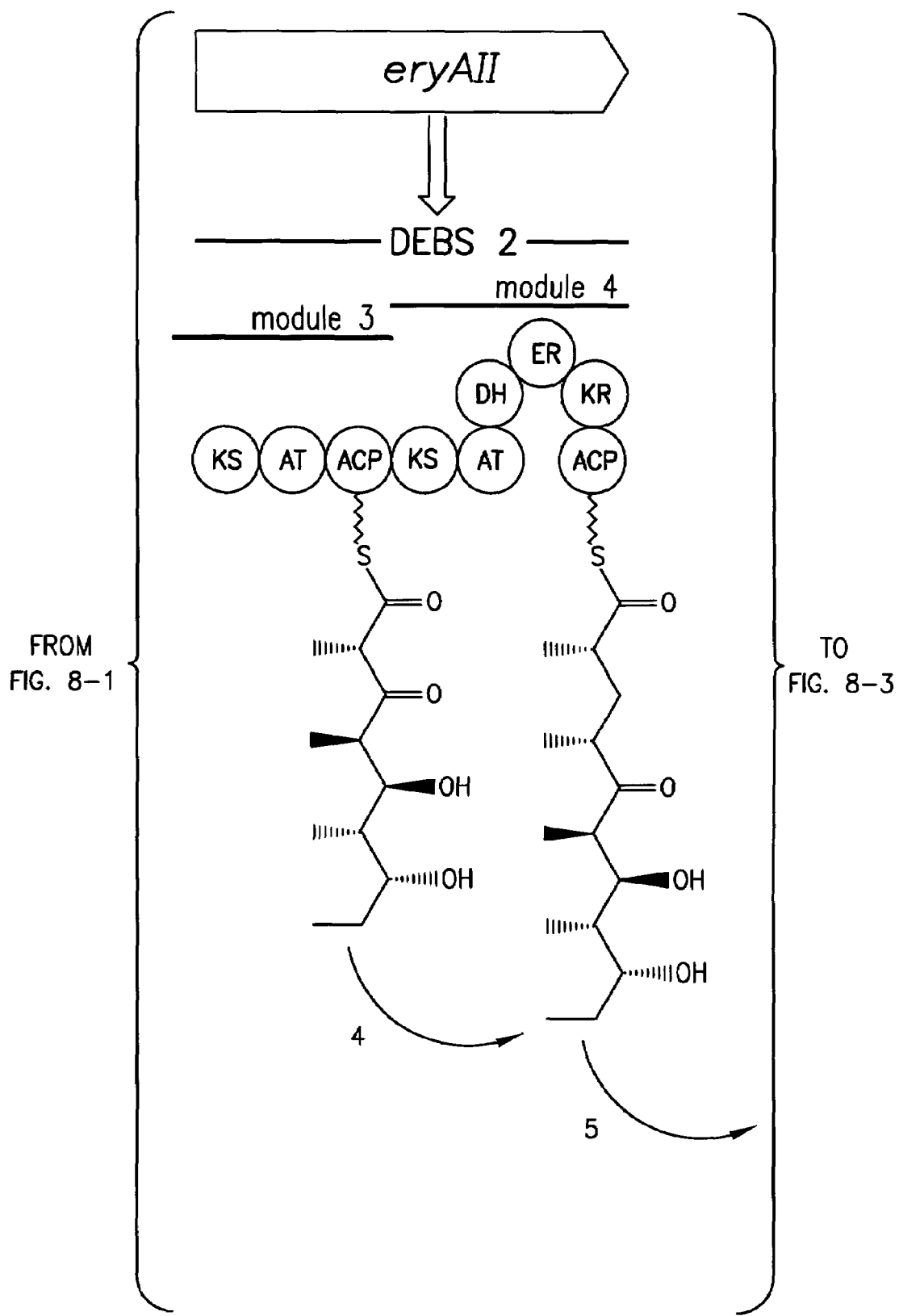
Figures 3, 8:
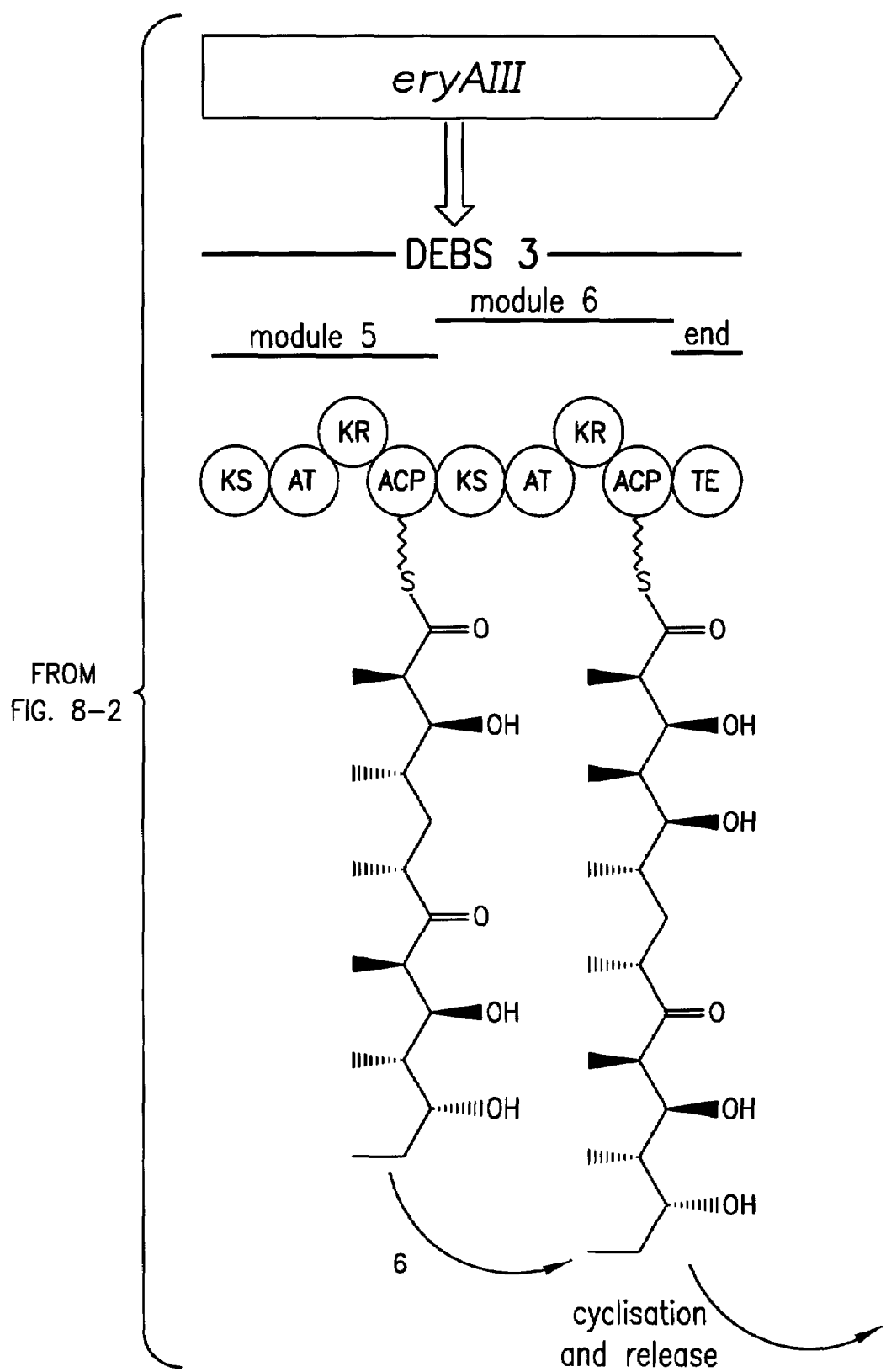
Figure 10:
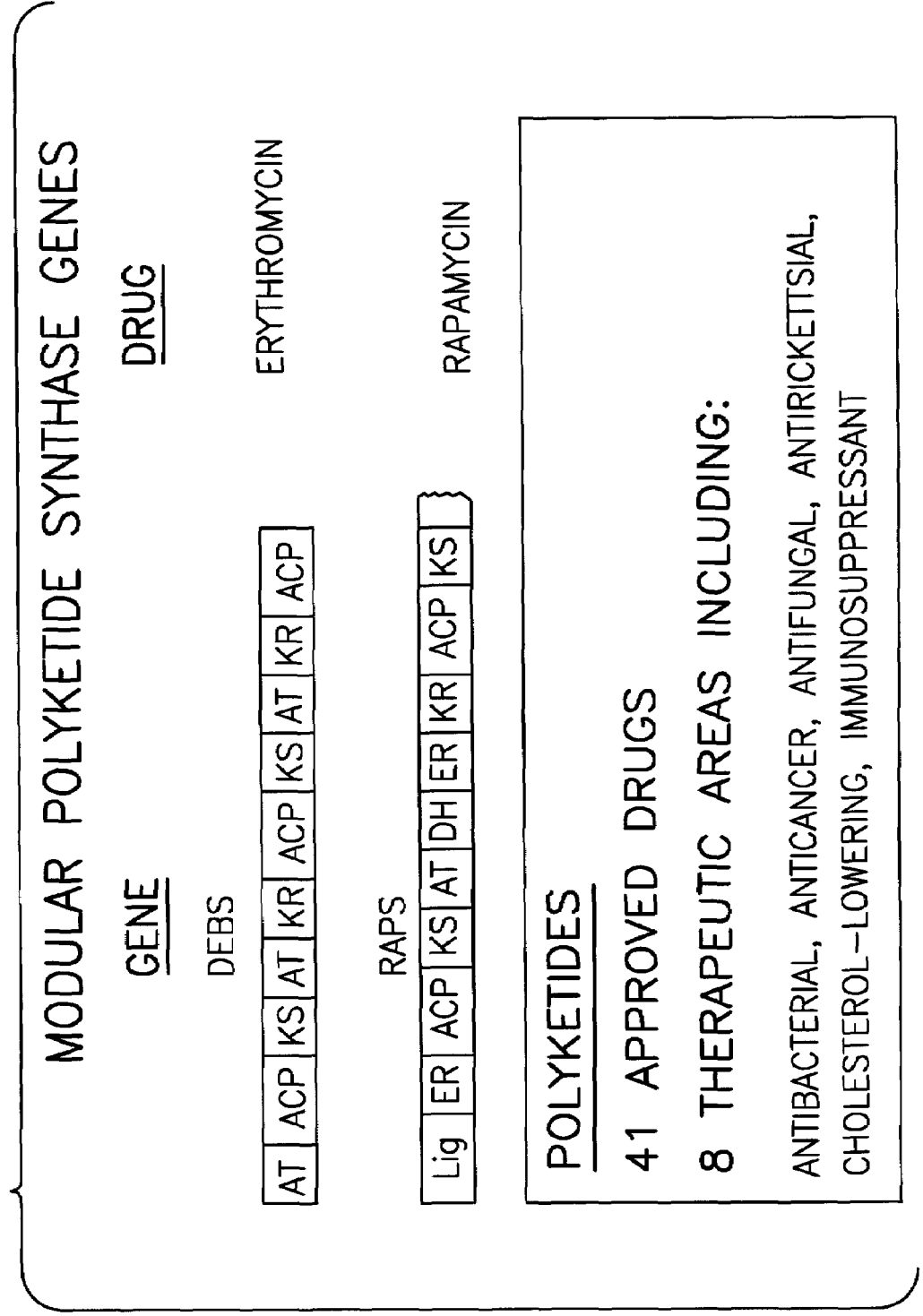
FIG. 10 depicts the protein functional domains of certain modular polyketide synthase genes.

Polyketide synthases (PKSs) are modular proteins in which different functional domains catalyze different steps of the synthesis reactions (see, for example, Cortes et al., *Nature* 348:176, 1990; MacNeil et al., *Gene* 115:119, 1992; Schwecke et al., *Proc. Natl. Acad. Sci. USA* 92:7839, 1995). For example, FIGS. 8 and 9 (from WO 98/01546) depict the different functional domains of bacterial polyketide synthase genes responsible for the production of erythromycin and rapamycin, respectively (see also FIG. 10). Each of these genes is an example of a so-called "class I" bacterial PKS gene. As shown, each cycle of polyketide chain extension is accomplished by a catalytic unit comprising a collection of functional domains including a β-ketoacyl ACP synthase domain (KS) at one end and an acyl carrier protein (ACP) domain at the other end, with one or more other functional domains (selected from the group consisting of an acyl transferase [AT] domain, a β-ketoacyl reductase [KR] domain, an enoyl reductase [ER] domain, a dehydratase [DH] domain, and a thioesterase [TE] domain).

Class II bacterial PKS genes are also modular, but encode only a single set of functional domains responsible for catalyzing chain extension to produce aromatic polyketides; these domains are re-used as appropriate in successive extension cycles (see, for example, Bibb et al., *EMBO J.* 8:2727, 1989; Sherman et al., *EMBO J.* 8:2717, 1989; Fernandez-Moreno et al., *J. Biol. Chem.* 267:19278, 1992; Hutchinson et al., *Annu. Rev. Microbiol.* 49:201, 1995). Diversity is generated primarily by the selection of particular extension units (usually acetate units) and the presence of specific cyclases (encoded by different genes) that catalyze the cyclization of the completed chain into an aromatic product.

It is known that various alterations in and substitutions of class I PKS functional domains can alter the chemical composition of the polyketide product produced by the synthetic enzyme (see, for example, Cortes et al., *Science* 268:1487, 1995; Kao et al., *J. Am. Chem. Soc.* 117:9105, 1995; Donadio et al., *Science* 252:675, 1991; WO 93/1363). For class II PKSs, it is known that introduction of a PKS gene from one microbial strain into a different microbial strain, in the context of a different class II PKS gene cluster (e.g., different cyclases) can result in the production of novel polyketide compounds (see, for example, Bartel et al., *J. Bacteriol.* 172: 4816, 1990; WO 95/08548).

The present invention provides a new system for generating altered PKS genes in which the arrangement and/or number of functional domains encoded by the altered gene differs from that found in any naturally-occurring PKS gene. Any PKS gene fragment can be used in accordance with the present invention. Preferably, the fragment encodes a PKS functional domain that can be linked to at least one other PKS functional domain to generate a novel PKS enzyme. A variety of different polyketide synthase genes have been cloned (see, for example, Schwecke et al., *Proc. Natl. Acad. Sci. USA* 92:7839, 1995; U.S. Pat. No. 5,252,474; U.S. Pat. No. 5,098, 837; EP Patent Application Number 791,655; EP Patent Application Number 791,656, each of which is incorporated herein by reference; see also WO 98/51695, WO 98/49315, and references cited therein, also incorporated by reference.), primarily from bacterial or fungal organisms that are prodigious producers of polyketides. Fragments of any such genes may be utilized in the practice of the present invention.

Peptide Synthetase Family

Peptide synthetases are complexes of polypeptide enzymes that catalyze the non-ribosomal production of a variety of peptides (see, for example, Kleinkauf et al., *Annu. Rev. Microbiol.* 41:259, 1987; see also U.S. Pat. No. 5,652,116; U.S. Pat. No. 5,795,738). These complexes include one or more activation domains (DDA) that recognize specific amino acids and are responsible for catalyzing addition of the amino acid to the polypeptide chain. DDA that catalyze the addition of D-amino acids also have the ability to catalyze the recemization of L-amino acids to D-amino acids. The complexes also include a conserved thioesterase domain that terminates the growing amino acid chain and releases the product. FIG. 11 presents an exemplary list of products generated by peptide synthetases that are currently being used as pharmacologic agents.

Figure 12:
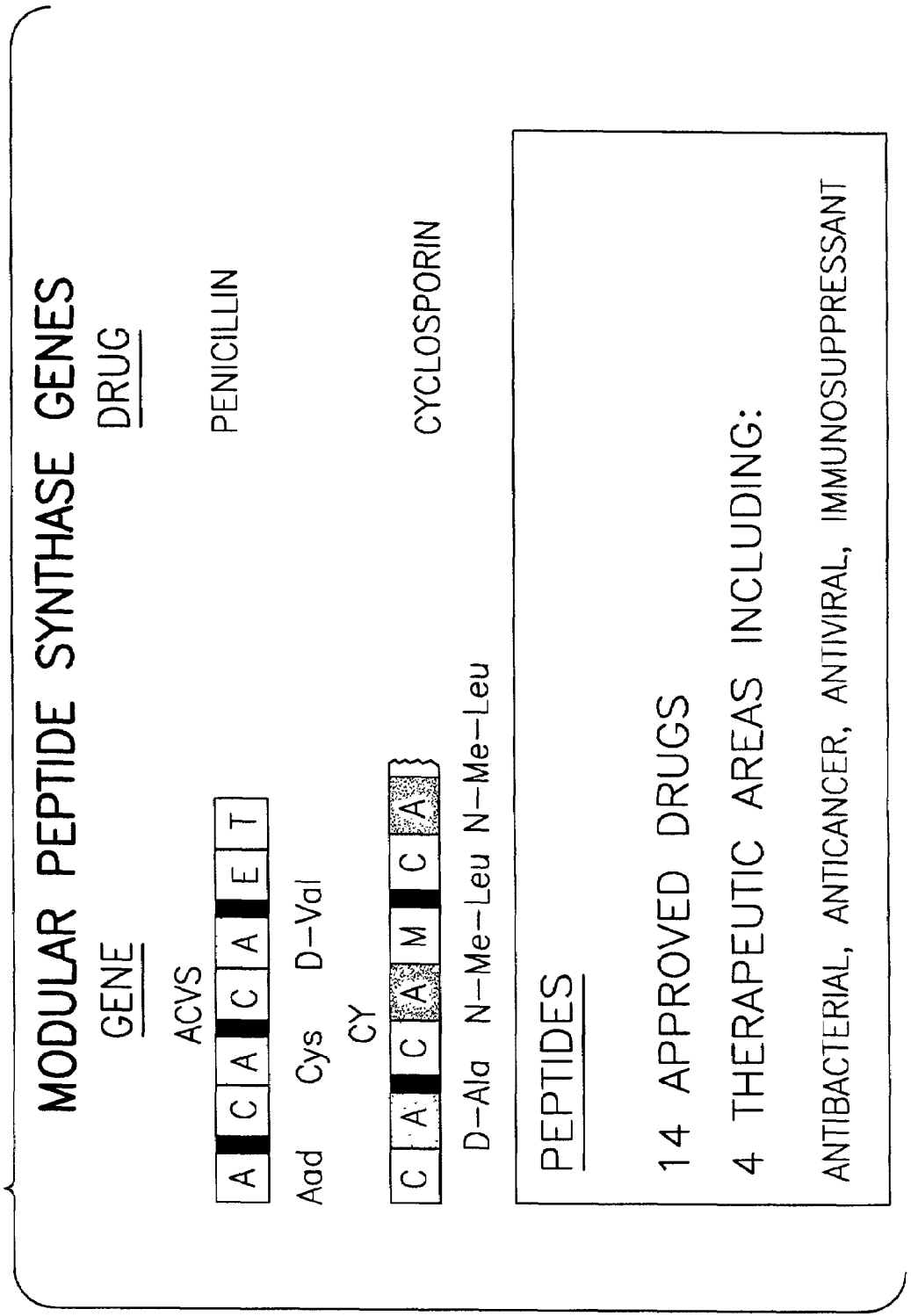
FIG. 12 depicts the protein functional domains of certain modular peptide synthetase genes.
Figure 13:
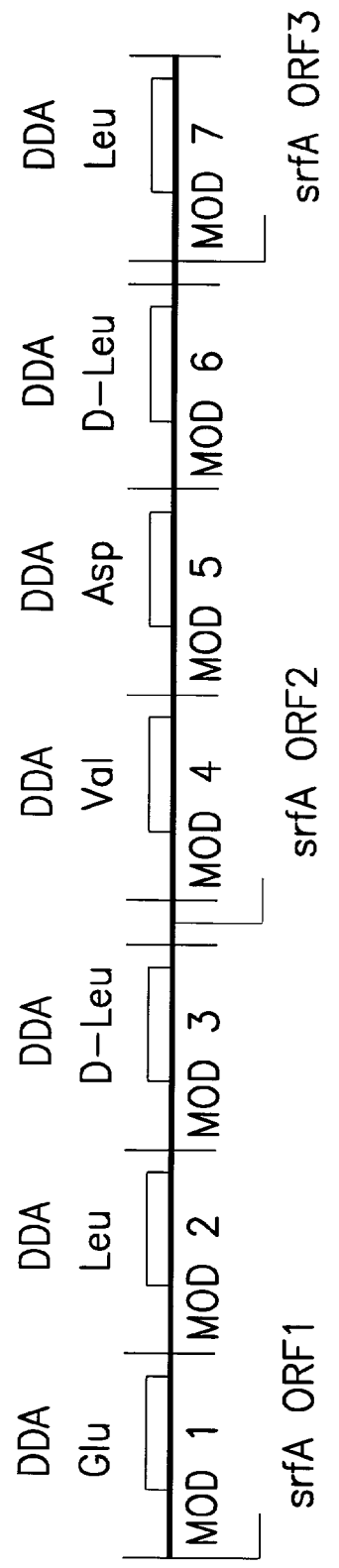
FIG. 13 depicts the structure of the srfA peptide synthetase operon.

The genes that encode peptide synthetases have a modular structure that parallels the funcitonal domain structure of the enzymes (see, for example, Cosmina et al., *Mol. Microbiol* 8:821, 1993; Kratxxchmar et al., *J. Bacteriol.* 171:5422, 1989; Weckermann et al., *Nuc. Acids res.* 16:11841, 1988; Smith et al., *EMBO J.* 9:741, 1990; Smith et al., *EMBO J.* 9:2743, 1990; MacCabe et al., *J. Biol. Chem.* 266:12646, 1991; Coque et al., *Mol. Microbiol.* 5:1125, 1991; Diez et al., *J. Biol. Chem.* 265:16358, 1990; see also FIG. 12). For example, FIG. 13 (from U.S. Pat. No. 5,652,116) presents the structure of one exemplary peptide synthetase gene operon, the srfA operon.

The sequence of the peptide produced by a particular peptide synthetase is determined by the collection of functional domains present in the synthetase. The present invention, by providing a system that allows ready linkage of particular peptide synthetase functional domains to one another, therefore provides a mechanism by which new peptide synthase genes can be produced, in which the arrangement and/or number of functional domains is varied as compared with naturally-occurring peptide synthase genes. The peptide synthase enzymes encoded by such new genes are expected to produce new peptide products. The present invention therefore provides a system for the production of novel peptides, through the action of hybrid peptide synthase genes.

Terpene Synthase Family

Isoprenoids are chemical compounds whose structure represents a modification of an isoprene building block. The isoprenoid family includes a wide range of structurally diverse compounds that can be divided into classes of primary (e.g., sterols, carotenoids, growth regulators, and the polyprebol substitutents of dolichols, quinones, and proteins) and secondary (e.g., monoterpenes, sesquiterpenes, and diterpenes) metabolites. The primary metabolites are important for biological phenomena such as the preservation of membrane integrity, photoprotection, orchestration of developmental programs, and anchoring of essential biochemical activities to specific membrane systems; the secondary metabolites participate in processes involving inter-cellular communication, and appear to mediate interactions between plants and their environment (see, for example, Stevens, in *Isopentoids in Plants* [Nes et al., eds], Macel Dekker et al., New York, pp. 65-80, 1984; Gibson et al., *Nature* 302:608, 1983; and Stoessl et al., *Phytochemistry* 15:855, 1976).

Figure 14:
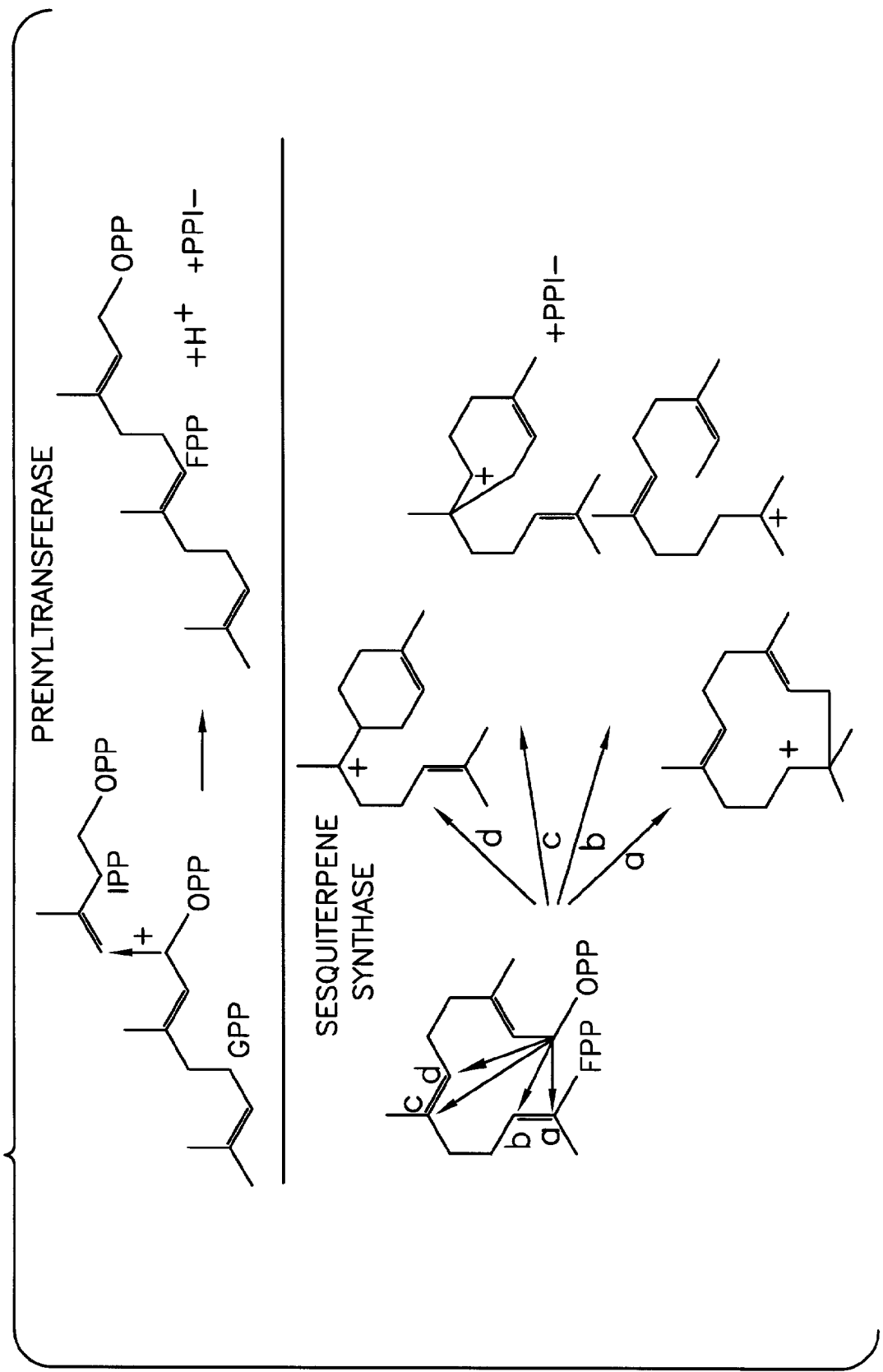
FIG. 14 depicts the synthesis of isoprenoids through the polymerization of isoprene building blocks.
Figure 15:
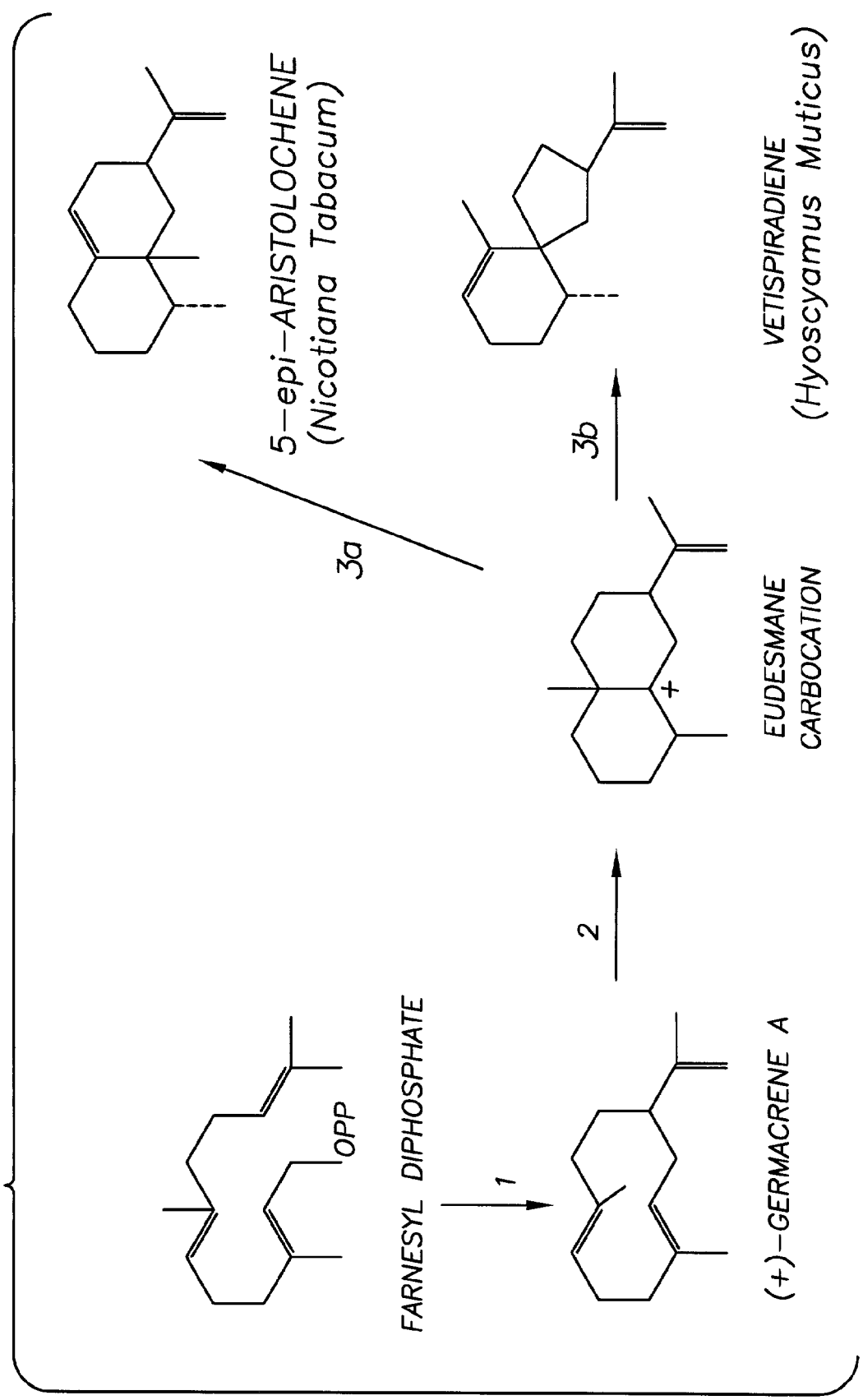
FIG. 15 depicts certain cyclization and intermolecular bond formation reactions catalyzed by isoprenoid, or terpene synthases.

Isoprenoids are synthesized through the polymerization of isoprene building blocks, combined with cyclization (or other intramolecular bond formation) within intermediate or final product molecules. The polymerization reactions are catalyzed by prenyltransferases that direct the attack of an electron deficient carbon on the electron-rich carbon atom in the double bond on the isoprene unit (see FIG. 14, from U.S. Pat. No. 5,824,774). Cyclizations and other intramolecular bond formation reactions are catalyzed by isoprenoid, or terpene, synthases (see FIG. 15, from U.S. Pat. No. 5,824,774).

Figure 16:
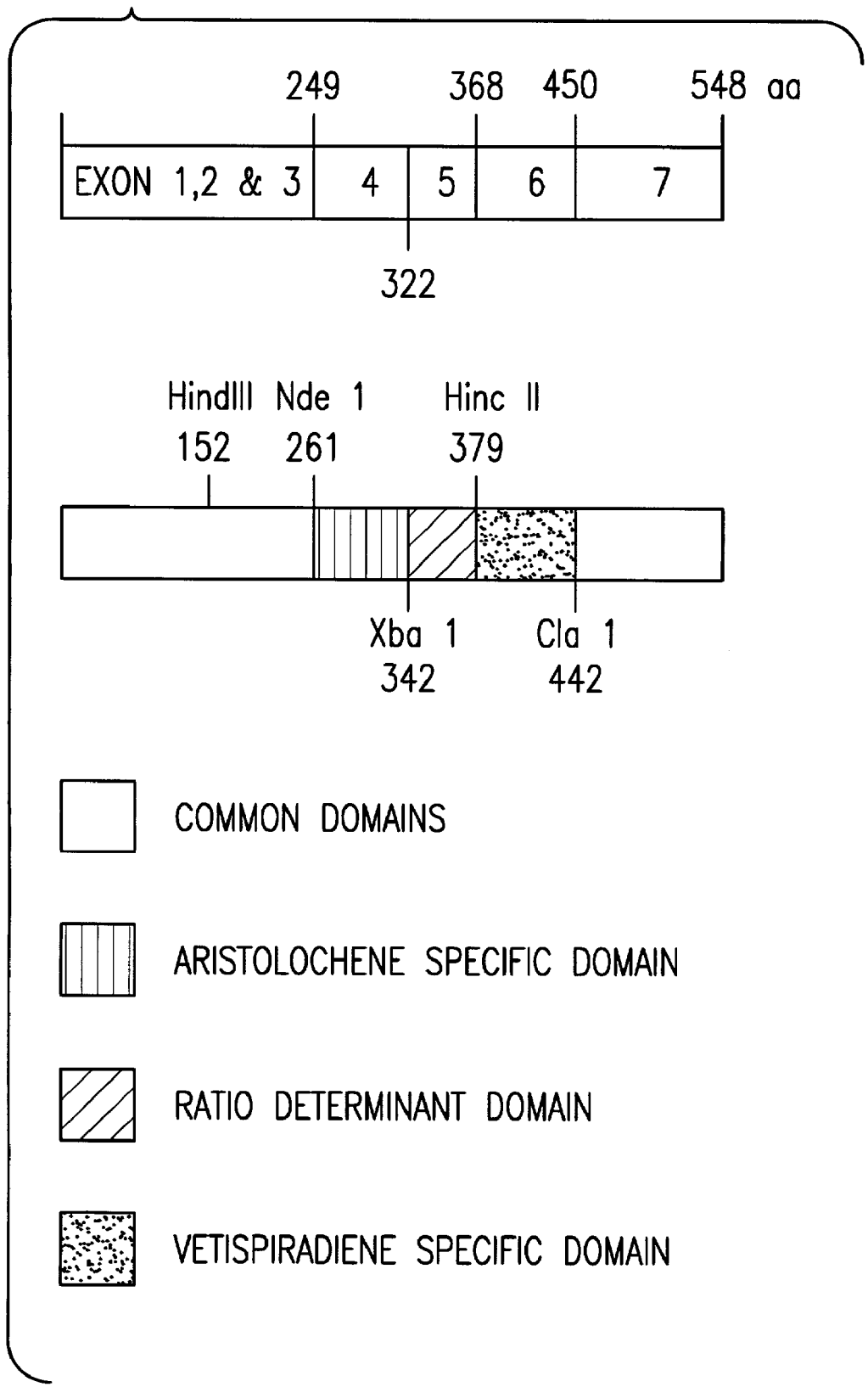
FIG. 16 presents a schematic illustration of the correspondence between natural exons and functional domains within isoprenoid synthases.

The terpene synthase proteins are modular proteins in which functional domains tend to correspond with natural exons (see, for example, U.S. Pat. No. 5,824,774, incorporated herein by reference). FIG. 16, from U.S. Pat. No. 5,824, 774, presents a schematic illustration of the correspondence between natural exons and funcitonal domains within isoprenoid synthases. The upper diagram represents the organization of exons within the TEAS gene, which is nearly identical to that of the HVS and casbene synthase genes; the lower diagram shows the alignment of functional domains to the exonic organization of the TEAS and HVS genes.

As will be appreciated in light of the present application, the instant invention provides a system by which DNA molecules encoding isoprenoid synthase functional domains may be linked to one another to generate novel hybrid isoprenoid synthase genes in which the arrangement and/or number of functional domains is varied as compared with those observed in naturally-occurring isoprenoid synthase genes. These novel hybrid genes will encode novel hybrid proteins that are expected to catalyze the synthesis of new isoprenoid compounds.

As mentioned above, in some embodiments of the invention, DNA molecules encoding functional domains from one protein family are linked to DNA molecules encoding functional domains from a different protein family. Of particular interest in accordance with the present invention are reactions in which DNAs encoding polyketide synthase functional domains are linked with DNAs encoding peptide synthetase functional domains. Alternative preferred embodiments involve linkage of fatty acid synthase functional domains with either or both of polyketide synthase functional domains and peptide synthetase functional domains. The hybrid genes created by such inter-family ligation reactions can then be tested according to known techniques to determine their ability to encode proteins that catalyze the synthesis of novel chemical compounds related to polyketides, fatty acids, and/or peptides.

As also mentioned above, it will be appreciated that the DNA molecules selected to be linked to one another in a particular experiment are not limited to molecules encoding functional domains or portions thereof, molecules encoding "linker" amino acids may additionally or alternatively be employed, as can non-coding molecules, depending on the desired final product.

To give but one example, it may sometimes be desirable to include in a final ligated molecule certain control sequences that will regulate expression of other DNA sequences to which the control sequences are linked when the ligated molecule is introduced into a host cell or an in vitro expression system. For example, transcriptional control sequences, RNA splicing control sequences, other RNA modification control sequences, and/or translational control sequences may be included in one or more of the DNA molecules to be linked together. A wide variety of such expression control sequences are well known in the art (see, for example, Sambrook et al., *Molecular Cloning: A Laboratory Manual*, 2nd Ed., Cold Spring Harbor Press, Cold Spring Harbor, N.Y., 1989, incorporated herein by reference); those of ordinary skill in the art will be familiar with considerations relevant to selecting desirable control sequences for use in their particular application. In general, so long as such control sequences direct expression of other DNA sequences to which they are linked when those DNA sequences are introduced into a cell or an in vitro expression system, they are appropriate for use in accordance with the present invention.

Other DNA modules that could desirably be used in accordance with the present invention include, for example, modules encoding a detectable protein moiety (e.g., an enzyme moiety that catalyzes a detectable reaction such as a color change or induction of fluorescence or luminescence, or a moiety that interacts with a known monoclonal antibody, etc), modules encoding a moiety that allows ready purification of any polypeptide encoded by the ligated product DNA molecule (e.g., a GST domain, a copper chelate domain, etc.), or any other module desired by the researcher.

Directional Ligation

As discussed herein, one particularly valuable application of the inventive techniques is for the linkage of multiple different nucleic acid molecules to one another. Because the embodiments of the invention that provide product molecules with 3' or 5' overhangs allow the sequence and length of those overhangs to be selected at the practitioner's discretion, molecules can readily be prepared for ligation only to certain designated partners, in certain designated orders, so that multi-member ligation reactions can be performed with only minimal generation of spurious or undesired ligation products.

Figure 17:
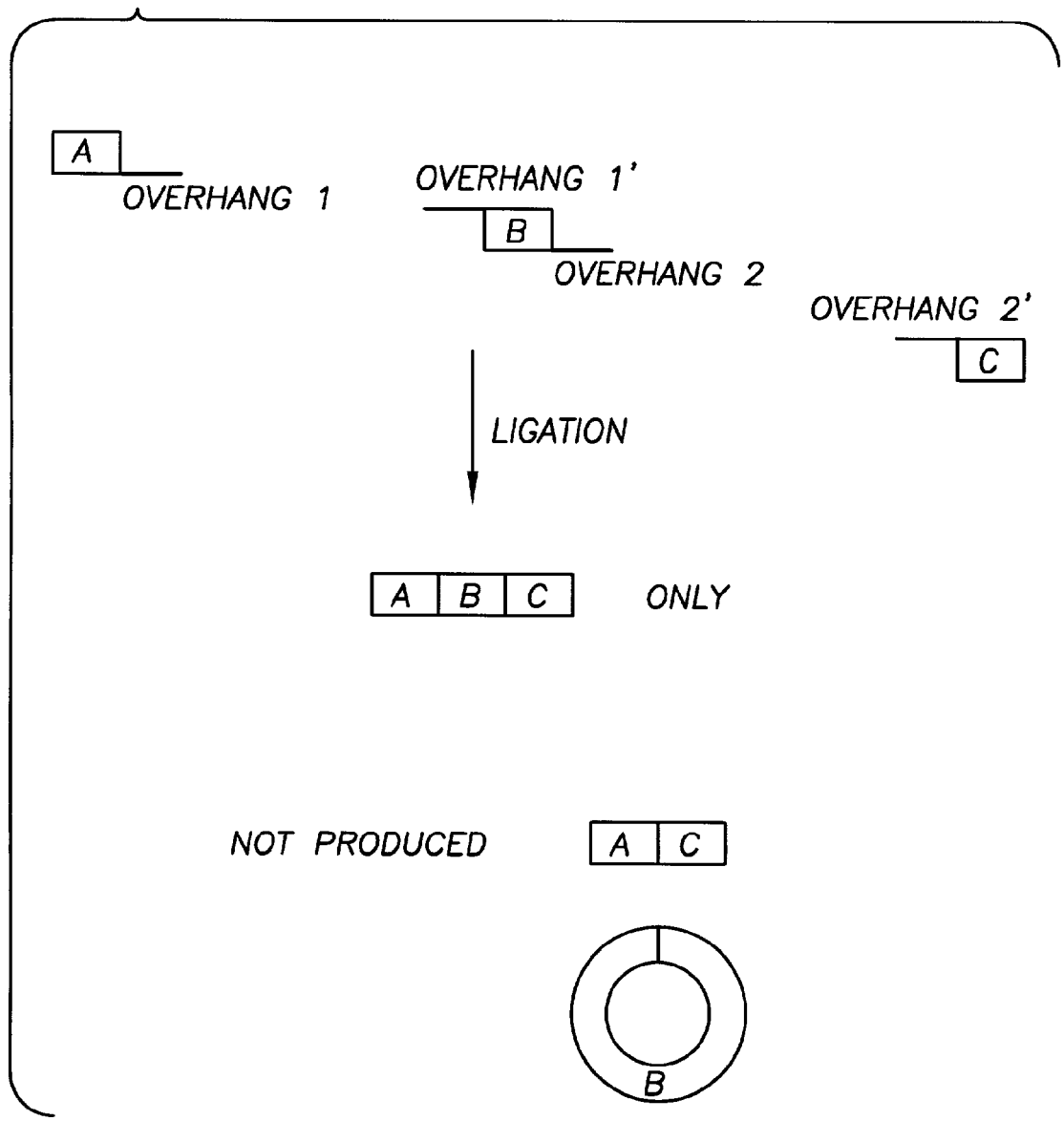
FIG. 17 depicts one generic example of a directional ligation reaction.

FIG. 17 presents a schematic depiction of one generic example of such a directional ligation reaction according to the present invention (FIGS. 18-22 and Example 1 describe a specific example). As shown, a first nucleic acid molecule, designated "A", contains a first overhang, designated "overhang 1" on one end. A second nucleic acid molecule, "B" is flanked by a second overhang, "overhang 1'", that is complementary to overhang 1, and a third overhang, "overhang 2", that is preferably unrelated to, and certainly not identical with, overhang 1, A third nucleic acid molecule, "C", contains a fourth overhang, "overhang 2'", that is complementary with overhang 2. As will be appreciated by those of ordinary skill in the art, a ligation reaction including all three of these nucleic acid molecules will produce only a single reaction product, "ABC", and will not produce "AC" or circular "B" products due to the incompatibility of the ends that would have to be ligated together to generate such products.

Mutagenesis

In another particularly useful application, the inventive techniques and reagents may be utilized to alter the nucleotide sequence of nucleic acid molecules that are being linked together. A separate mutagenesis reaction is not required. Rather, primers and/or overhangs whose sequence and length may be selected by the practitioner are utilized to create single-stranded regions between molecules to be ligated, which single-stranded regions include new or altered sequences as desired. These single-stranded regions can subsequently be filled in with a polymerase that will synthesize a strand complementary to the new sequence. Alternatively or additionally, primers may be employed that add sequence to a particular product molecule strand that will be copied in an extension or amplification reaction.

Exon Shuffling

One particular application of the techniques and reagents described herein is in the production of libraries of hybrid nucleic acid molecules in which particular collections of DNA molecules, or "exons" have been linked to one another. That is, an "exon shuffling" reaction is one in which a single reaction mixture (e.g., a ligation mixture or a splicing reaction—discussed further below) generates at least two, and preferably at least 10, 100, 1000, 10,000, 100,000, or 1,000,000 different product molecules.

As used herein, the term "exon" refers to any DNA molecule that is to be ligated to another DNA molecule. An exon may include protein-coding sequence, may be exclusively protein-coding, or may not include protein-coding sequence at all. The term "exon shuffling" is intended to indicate that, using the techniques and reagents of the present invention, collections of exons can be produced that can be ligated to one another in more than one possible arrangement. For example, as depicted in FIG. 23, the inventive techniques and reagents may be employed in a ligation reaction in which a single upstream exon, A, can be ligated to any one of a collection of different internal exons (B1-B4 in FIG. 23), which in turn is further ligated to a downstream exon, C.

Figure 23:
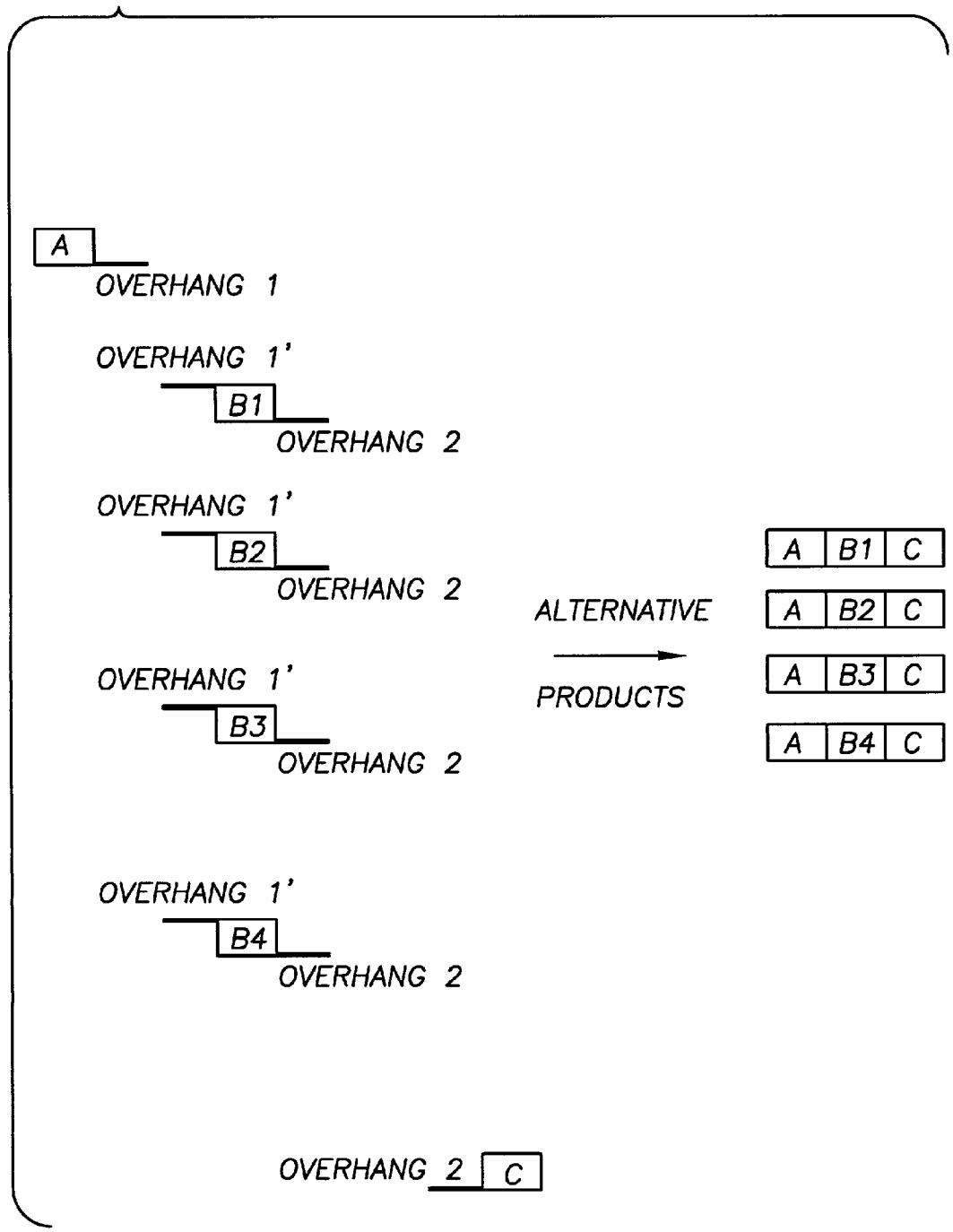
FIG. 23 shows an inventive identity exon shuffling reaction.

Those of ordinary skill in the art will readily appreciate that FIG. 23 presents just one particular embodiment of an "identity exon shuffling" reaction (i.e., one in which the identity of a particular exon is different in different products of the shuffling reaction) according to the present invention. A wide array of related reactions is included within the inventive "exon shuffling" concept, and particularly within the concept of "identity exon shuffling". For example, more than one exon may be varied in a particular shuffling reaction. In fact, it is not necessary to have upstream and downstream terminal exons that are uniform among shuffling products, as is depicted in FIG. 23. Such consistency may provide certain advantages, however, including an ability to amplify all shuffling products with a single set of amplification primers (discussed in more detail below). Even if invariant flanking exons are preserved, however, more than one internal exon may be varied; even if additional invariant internal exons are also provided.

FIG. 24 presents an embodiment of a different sort of exon shuffling reaction that may be performed according to the present invention. In the particular embodiment shown in FIG. 24, upstream (A) and downstream (H) exons are provided in combination with a wide variety of possible internal exons (B-G). All exons have compatible overhangs. In such a reaction, the possibilities for internal exons arrangements to be found in product molecules are infinite. Also, because no exons (other than the optional flanking exons) are restricted to a particular position in the exon chain, this type of shuffling is referred to as "positional shuffling".

Of course, those of ordinary skill in the art will appreciate that FIG. 24 is but an exemplary embodiment of inventive positional shuffling systems. For example, it may well be desirable to employ at least two sets of compatible overhangs and to ensure that potential internal exons are not flanked by compatible ends; otherwise, intramolecular circularization can present serious complications as a competing reaction in inventive ligations. Also, it is possible to perform an exon shuffling reaction that represents a compromise between the extremes of allowing identity shuffling at a single position while holding all other positions fixed (e.g., FIG. 17) and allowing complete shuffling at all positions. Merely by selecting the compatibility of the overhangs, the practitioner may limit the number of exons able to incorporate at a particular chain site, while allowing more variability at a different site.

One of the advantages of the present invention is that it allows simultaneous multi-site variation, optionally in combination with positional variation (i.e., the possibility that a particular exon sequence could end up in different positions in different product molecules. To give but one example of the significance of this phenomenon, FIG. 25 shows that other techniques might allow production of libraries in which a single position in an exon chain can be varied at one time. For a three-exon chain in which 10 different exons could be employed at each of the positions, 30 different variants can be produced (A1BC, A2BC, A3BC, . . . A10BC, AB1C, AB2C, . . . AB10C, ABC1, ABC2, . . . ABC10). By contrast, if all three positions can be varied simultaneously, as is possible in accordance with the present invention, 1000 different variants can be produced.

As discussed above, it is now accepted that the evolutionary process often produces new genes by re-sorting existing exons. Large gene families have apparently been produced by exon shuffling. According to the present invention, it is desirable to employ the inventive techniques both to link particular selected functional domains to one another (see above) and to shuffle exons found in those gene families, so that a library of (at least two) product genes is generated.

The inventive exon shuffling techniques may be applied to any desired collection of exons. Preferably, they are applied to exons including protein-coding sequences. More preferably, they are applied to protein-coding exons that have been re-used in evolution in different members of gene families (see discussion above). In one particularly preferred embodiment of the exon shuffling system of the present invention, the exons to be shuffled represent functional domains of synthetic enzymes. As discussed above with respect to ligation, re-sort exons from within family or between or among families.

Particularly preferred gene families to which inventive exon shuffling techniques may be applied include, but are not limited to, the tissue plasminogen activator gene family, the animal fatty acid synthase gene family, the polyketide synthase gene family, the peptide synthetase gene family, and the terpene synthase gene family. The class I bacterial polyketide synthase gene family presents a particularly attractive target for application of the inventive exon shuffling techniques in that the co-linearity of functional domains and catalytic capabilities is so well established for this family.

Also, the close mechanistic relationship between class I polyketide synthases and animal fatty acid synthases, class II polyketide synthases, and/or intermediate class polyketide synthases (e.g., fungal polyketide synthases, whose funcitonal organization and catalytic characteristics are apparently intermediate between those of the bacterial class I and class II polyketide synthases) renders shuffling reactions that admix DNAs encoding functional domains of two or more of these different families particularly intriguing. Such reactions will generate libraries of new synthetic enzymes, which in turn will generate libraries of new chemical compounds that can be assayed according to any available technique to determine whether they have interesting or desirable biological activities.

Integration with Existing Technologies

It will be appreciated that the present invention does not describe the only available method for linking selected nucleic acid molecules to one another. For example, the established restriction-enzyme-based technology clearly allows cleavage and ligation of nucleic acid molecules, albeit without the convenience and other advantages of the inventive system. Also, techniques have been developed by which ribozymes can be employed to mediate cleavage and ligation of nucleic acids at the RNA or DNA level (see, for example, U.S. Pat. No. 5,498,531; U.S. Pat. No. 5,780,272; WO 9507351; WO 9840519, and U.S. Patent Application Ser. No. 60/101,328, filed Sep. 21, 1998, each of which is incorporated herein by reference; see also Example 4).

Each of these different systems for nucleic acid manipulation offers certain advantages and disadvantages. For example, ribozyme-mediated systems offer the distinct advantage that shuffling reactions may be performed in vivo if desired (see, for example, U.S. Patent Application Ser. No. 60/101,328, filed Sep. 21, 1998). Furthermore, once a shuffling cassette is generated in which an exon of interest is linked to a first trans-splicing ribozyme component, that exon may be ligated to any other exon that is linked to a second trans-splicing component that is compatible with the first trans-splicing component in a simple trans-splicing reaction. Thus, the more the ribozyme-mediated system is utilized, and the larger the number of shuffling cassettes generated by its use, the more powerful it becomes.

Ribozyme-mediated nucleic acid manipulation, like the techniques described herein, can be used for exon shuffling, and can be engineered to direct seamless ligation of any selected nucleic acid molecules. Furthermore, like the inventive system, the ribozyme-mediated system may be engineered so that the agents that mediate ligation (the ribozyme components in the ribozyme-mediated system; the overhangs in the inventive system) are only compatible with certain selected other ligation-mediating agents. This ability allows one to perform directed ligation reactions analogous to those depicted in FIG. 17, in which a collection of exons is incubated together but only certain selected exons can become ligated to one another (see, for example, Example 4 and FIG. 29).

One particularly preferred embodiment of the present invention represents an integration of the primer-based manipulation techniques described herein with the ribozyme-mediated techniques described in the above-referenced patents and patent applications. Specifically, the primer-based nucleic acid manipulation techniques described herein are utilized to construct ribozyme-associated shuffling cassettes that are then employed in splicing reactions to generate hybrid nucleic acid molecules that can subsequently be cloned and manipulated using inventive primer-based strategies.

Figure 26:
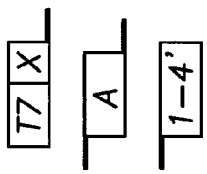
FIG. 26 presents one version of a combined primer-based/ribozyme-mediated nucleic acid manipulation scheme according to the present invention.

FIG. 26 presents one version of such a combined primer-based/ribozyme-mediated nucleic acid manipulation scheme. As depicted, nine different product molecules are produced using inventive primer-based nucleic acid manipulation strategies. These molecules are designed to be ligated together to produce three different shuffling cassettes. The first shuffling cassette comprises (i) a promoter that will direct transcription of the cassette; (ii) a first tag sequence; (iii) an upstream terminal exon; and (iv) a first ribozyme component. The second shuffling cassette comprises (i) a promoter that will direct transcription of the cassette; (ii) a second ribozyme component, compatible with the first ribozyme component; (iii) an internal exon; and (iv) a third ribozyme component (optionally not compatible with the second ribozyme component). The third shuffling cassette comprises (i) a promoter that will direct transcription of the cassette; (ii) a fourth ribozyme component that is compatible with the third ribozyme component (and optionally not with the first ribozyme component); (iii) a downstream terminal exon; and (iv) a second tag sequence.

Given the ease with which shuffling cassettes may be generated using the inventive primer-based technology, there is no need for shuffling cassettes to be introduced into vectors; they may be transcribed directly. Of course, they may be introduced into vectors if so desired, preferably by means of the inventive primer-based nucleic acid manipulation techniques. Each cassette is transcribed and the transcription products are incubated with one another under splicing conditions, either in vitro or in vivo, to produce a hybrid molecule containing each of the three exons. The hybrid molecule may then be introduced into a vector or further manipulated, again preferably using the inventive primer-based manipulation technology.

Those of ordinary skill in the art will appreciate that more than one internal cassette may be employed in the system of FIG. 26, either in an exon shuffling (involving positional and/or identity shuffling) reaction or in a directed ligation reaction in which only one copy of each exon will be introduced into the hybrid molecule, in a pre-determined order. Alternatively or additionally, multiple alternative upstream or downstream exons may be employed, or such terminal exons may be left out. In a particularly preferred embodiment of an identity exon shuffling reaction, multiple alternative exons are provided, and are simultaneously shuffled, for at least two positions (e.g., one internal position and one terminal position, two internal positions, or two terminal positions) in the hybrid molecule.

One advantage of the combined primer-based/ribozyme-mediated system depicted in FIG. 26 can be appreciated through consideration of the number of primers required to generate the indicated molecules, and/or to clone them into vectors or other desirable locales, according to the inventive methods. For example, sixty-seven primers are required to generate the initial product molecules if 10 different possible exon product molecules are produced for each of the "A", "B", and "C" exons. This is a relatively large number of primers, but is justified by the ease with which the product molecules are generated and ligated together using the inventive system, as compared with alternative methods (e.g., standard restriction-enzyme-based cloning techniques) available for the production of the shuffling cassettes. Only four primers are required to amplify the resulting shuffling cassettes, or to ligate them to other DNA molecules (e.g., a vector). Most importantly, only two primers are required to amplify (or ligate) assembled genes. Particularly where exon shuffling reactions have been performed, and a library of assembled genes is generated, it is valuable to be able to amplify all members of the library with the same two primers.

Automation

One particularly attractive feature of the inventive techniques and reagents is their susceptibility to automation. In particular, where large libraries of novel hybrid nucleic acids are being produced in inventive exon shuffling reactions, it may be desirable to employ an automated system (e.g., the Beckman 2000 Laboratory Automation Work Station) to accomplish the simultaneous manipulation of a large number of different samples.

Figure 27:
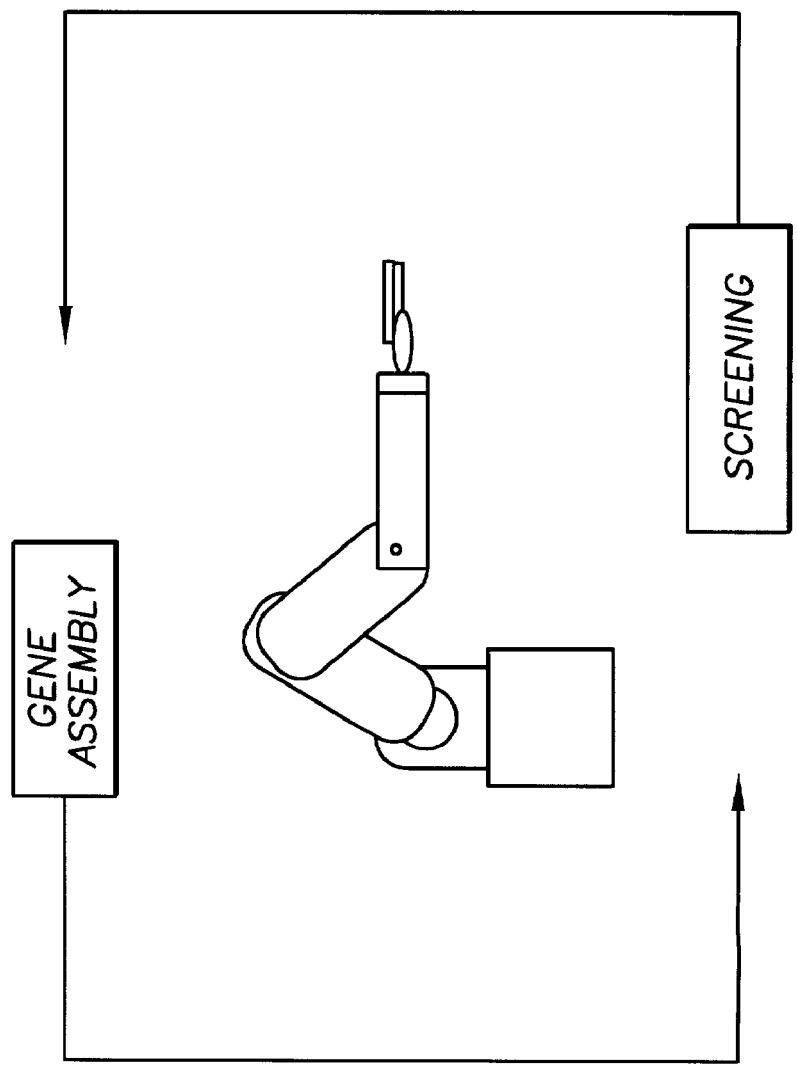
FIG. 27 depicts a robotic system that could be utilized in the practice of certain inventive methods.

To give but one example of a preferred automated application of the present inventive methods, FIG. 27 depicts a robotic system that could be utilized, for example, to accomplish exon shuffling as depicted in FIG. 27 and further to screen the products of the shuffling reaction for desired activities. For example, the product molecules depicted in the first column of FIG. 26 could be generated by PCR in 96 well plates using a Biomek 2000 system in combination with a multimek 96 automated 96-channel pipetter and a PTC-225 DNA engine (MJ Research), relying on the ORCA robot arm to move the plates from one location to another as necessary.

Preferably, multiple alternatives are simultaneously prepared of each exon product molecule (e.g., n "A" exons, A1-An, are prepared; as are x "B" exons, B1-Bx; and y "C" exons, C1-Cy), along with T7/X, 1-4', T7/5,6, and Y products. As discussed above, 67 different primers are required to produce these product molecules according to the inventive methodologies described herein.

The automated system is then programmed to pipette the appropriate product molecules together, along with desired ligation reagents, to produce 30 shuffling cassettes of the types depicted in the second column of FIG. 26. The system is then programmed to generate RNA from these shuffling cassettes using T7 RNA polymerase. The "A"-type, "B"-type, and "C"-type transcripts are then mixed together in all possible combinations, and are incubated (still in the robotic system) under trans-splicing conditions. All together, 1000 different splicing reactions will be performed.

A small aliquot of each splicing reaction is then removed and amplified with inventive primers so that the amplification products can readily be ligated with a recipient molecule such as a vector. The resulting plasmids may then be introduced into host cells (e.g., bacterial cells) for further amplification, or alternatively may be introduced into an in vivo or in vitro expression system so that any protein products encoded by the assembled shuffled genes may be assayed. Desirable expression systems will depend on the nature of the nucleic acid sequences that were shuffled. To give but one example, if fungal polyketide synthase gene fragments (e.g., encoding functional domains of fungal polyketide synthase proteins) were shuffled according to this approach, it may be desirable to express the hybrid proteins thereby generated in one or more fungal or mammalian cells types in order to assess their synthetic capabilities.

Kits

Reagents useful for the practice of the present invention may desirably be provided together, assembled in a kit. Certain preferred kits will include reagents useful for both primer-mediated and ribozyme-mediated nucleic acid manipulation reactions.

EXAMPLES

Example 1

Preparation and Ligation of Product Molecules with 5' Overhang Sequences

This Example describes the preparation and ligation of product molecules having 5' overhangs, using hybrid primers containing deoxyribonucleotides at their 3' ends and ribonucleotides at their 5' ends.

Figure 18:
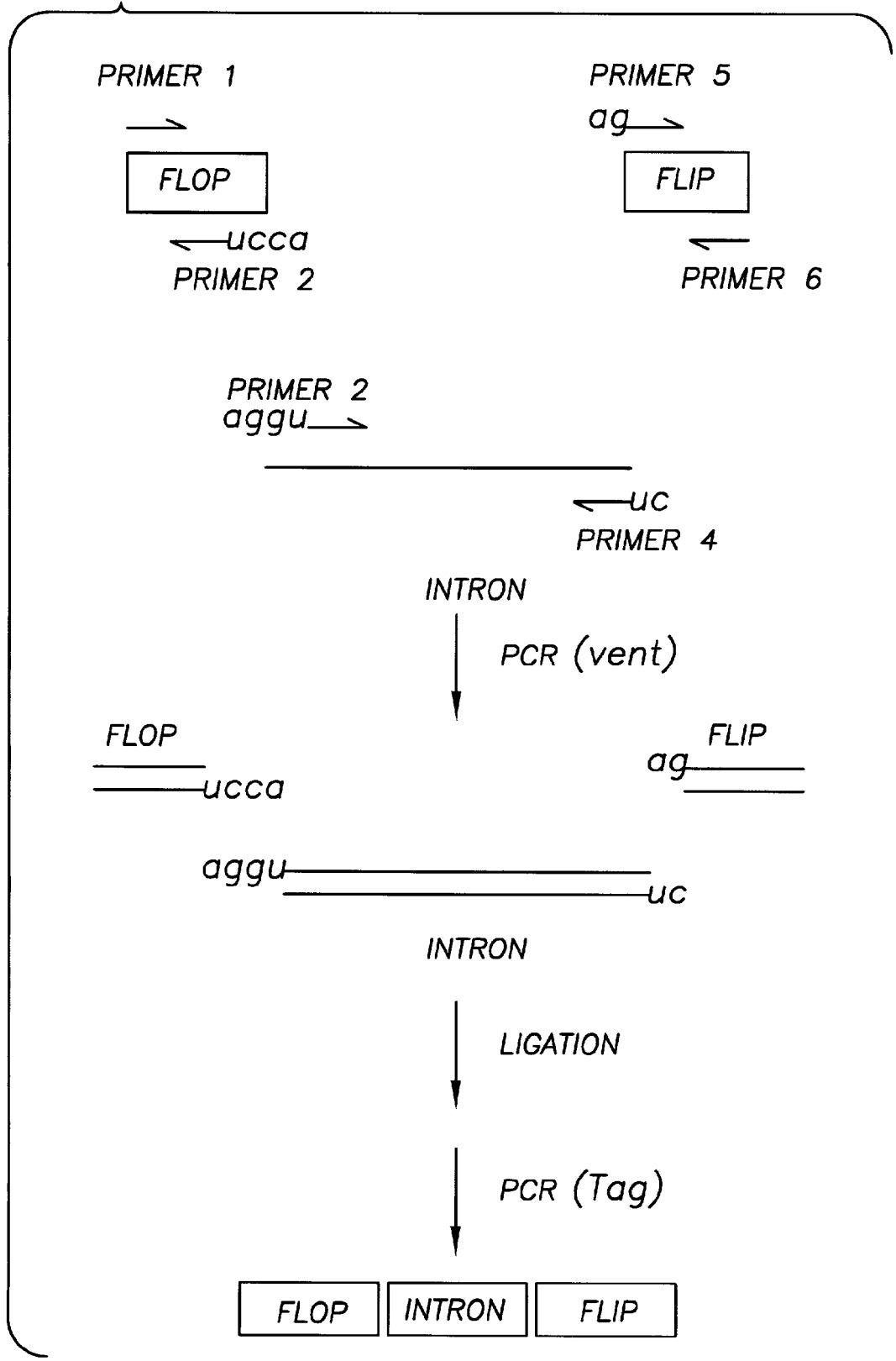
FIG. 18 presents a schematic representation of an inventive specific directional ligation reaction.

FIG. 18 presents a schematic of the particular experiment that was performed. As shown, three different product molecules were generated, two of which correspond to exons of the gene for subunit B of the human glutamate receptor, and one of which corresponds to an intron from the unrelated human β-globin gene. The particular glutamate receptor exons we utilized are known as Flip and Flop, and are indicated in FIGS. 19A and 19B, which present the nucleotide sequences of each of these exons (GenBank accession numbers X64829 and X64830, respectively).

We prepared each of our three product molecules by PCR, using Vent® DNA polymerase and plasmids Human GluR-B #7 (a cloned genomic fragment containing exons 13-16 of the human glutamate receptor B subunit) or HβT7 (a cloned genomic fragment containing exons 1-2 of the human β-globin gene).

The Flop exon was amplified with a 5' primer (primer 1 in FIG. 18; 5'-AAATGCGGTTAACCTCGCAG, SEQ ID NO 1) that is entirely DNA and corresponds to the first 20 bases of the Flop exon, in combination with a 3' primer (primer 2 in FIG. 18; 5'-accuTGGAATCACCTCCCCC SEQ ID NO 2) whose 5'-most four residues are RNA, as indicated by lower case letters in FIG. 18. This primer corresponds to the last 18 bases of the Flop exon plus 2 bases of intron. Together, these primers amplify a fragment corresponding to all of the human glutamate receptor Flop exon (115 basepairs) plus the first two residues at the 5' end of the intron.

Intron 1 was amplified with a 5' primer (primer 3 in FIG. 18; 5'-agguTGGTATCAAGGTTACA, SEQ ID NO 3) whose sequence corresponds to the first 18 bases of the human β-globin intron 1, and whose 5'-most four residues are RNA, and are complementary to the four RNA residues at the 5' end of primer 2; in combination with a 3' primer (primer 4 in FIG. 18, 5'-cuAAGGGTGGGAAAATAGAC, SEQ ID NO 5) corresponding to the last 20 bases of the human β-globin intron 1, whose 5'-most two residues are RNA. These primers together amplify a fragment corresponding to the entire intron (129 bp), and 2 add two residues corresponding to the last two residues at the 3' end of the Flop exon.

The Flip exon was amplified with a 5' primer (primer 5 in FIG. 18, 5'-agAACCCCAGTAAATCTTGC, SEQ ID NO 4) corresponding to the first 18 bases of the human glutamate receptor Flip exon, whose 5'-most two residues are RNA and are complementary to the two RNA residues at the 5'-end of primer 4; in combination with a 3' primer (primer 6 in FIG. 18, 5'-CTTACTTCCCGAGTCCTTGG, SEQ ID NO 6) corresponding to the last 20 exon bases, that was entirely DNA. These primers together amplify a fragment corresponding to the entire Flip exon (115 bp) and the last two nucleotides at the 3' end of the intron.

Each amplification reaction included 400 μmole of each primer, kinased (using T4 polynucleotide kinase in 100 μl 1×NEB T4 ligase buffer [50 mM Tris-HCl pH 7.8, 10 mM MgCl$_2$, 10 mM DTT, 1 mM ATP, 25 μg/ml BSA] for 30 minutes at 37° C., followed by dilution to 10 pmol/μl with 200 μl nuclease-free dH$_2$O); 2 units Vent$_R$® (exo$^-$) polymerase (NEB, Beverly, Mass.), 100 μl 1×Vent buffer (10 mM KCl, 10 mM (NH$_4$)$_2$SO$_4$, 20 mM Tris, 2 mM MgSO$_4$, 0.1% Triton X-100); 200 μM dNTPs; and 5 ng of template plasmid. One cycle of (i) 95° C., 3 minutes; (ii) 60° C., 3 minutes; (iii) 72° C., 3 minutes was followed by 35 cycles of (i) 95° C., 15 seconds; (ii) 60° C., 15 seconds; (iii) 72° C., 30 seconds, in a Robocycler® gradient 40 (Stratagene, La Jolla, Calif.) thermalcycler.

We found that Vent$_R$® and Vent$_R$® (exo–) did not copy the ribonucleotides in our primers, so that, after amplification, each product molecule contained a 5' ribonucleotide overhang at one or both ends (4 nucleotides at the 3'-end of the Flop product; 4 nucleotides at the 5'-end of the β-globin intron product; 2 nucleotides at the 3'-end of the β-globin intron product; and 2 nucleotides at the 5'-end of the Flip product).

Each amplified product was precipitated with ethanol (EtOH) and was resuspended in 10 μL, 2 of which were run on a 6% polyacrylamide gel in order to verify the presence of all three amplification products. Aliquots (2-4 μL each) containing approximately equimolar quantities of each fragment were then combined in a ligation reaction containing 1× New England Biolabs (NEB) T4 ligase buffer (50 mM Tris, pH 7.8, 10 mM MgCl$_2$, 10 mM DTT, 1 mM ATP, 25 μg/ml BSA) and 0.5 U of T4 DNA ligase (NEB, Beverly, Mass.). The 20 μL reaction was incubated overnight at 4° C. to allow ligation to occur. Products of ligation were then amplified using primers 1 and 3 and Taq polymerase, which does copy RNA (Myers et al., *Biochem.* 6:7661, 1991). The amplification reaction contained 1× Taq buffer (20 mM Tris, pH 9.0, 50 mM KCl, 0.1% Triton X-100), 200 μM dNTPs, 5 Units of Taq polymerase (Promega, Madison, Wis.), 2 μL of the ligation mix, and 400 μmol of each primer.

Figure 20:
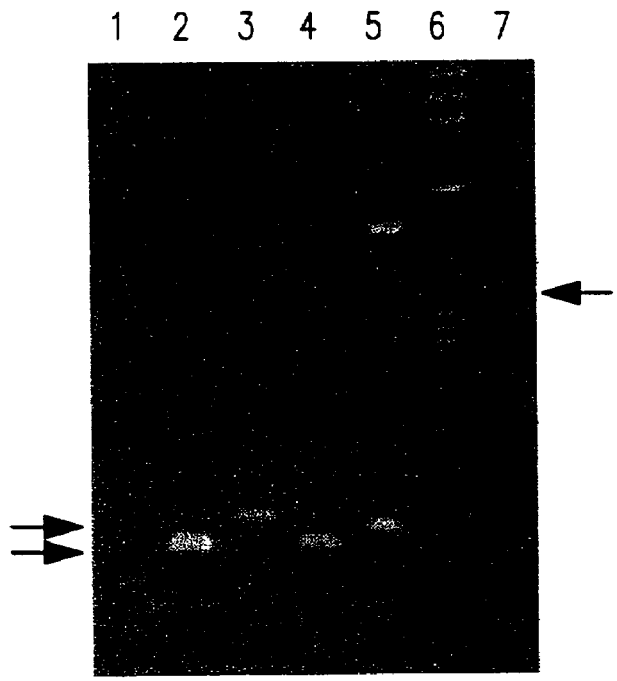
FIG. 20 shows the amplified hybrid molecules produced in an inventive directional ligation reaction.
Figure 21:
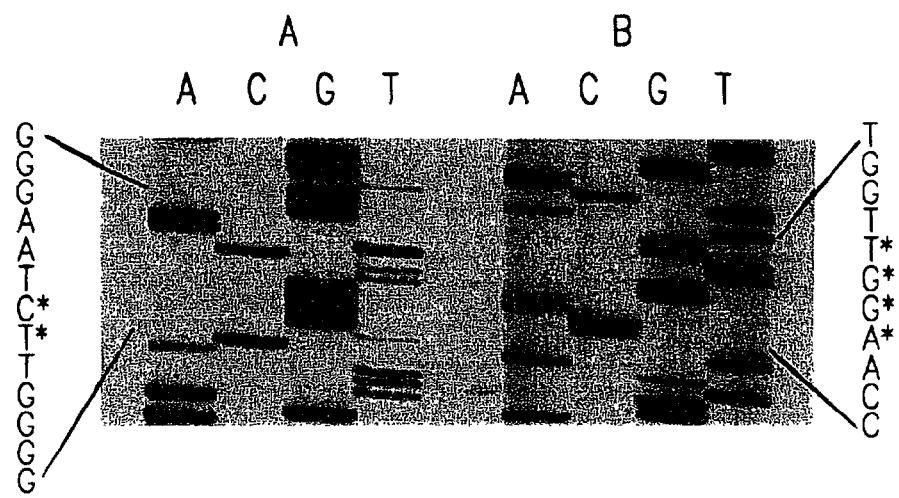
FIG. 21 presents the nucleotide sequence of the ligation junction in the hybrid molecules of FIG. 20.
Figures 1, 22A:
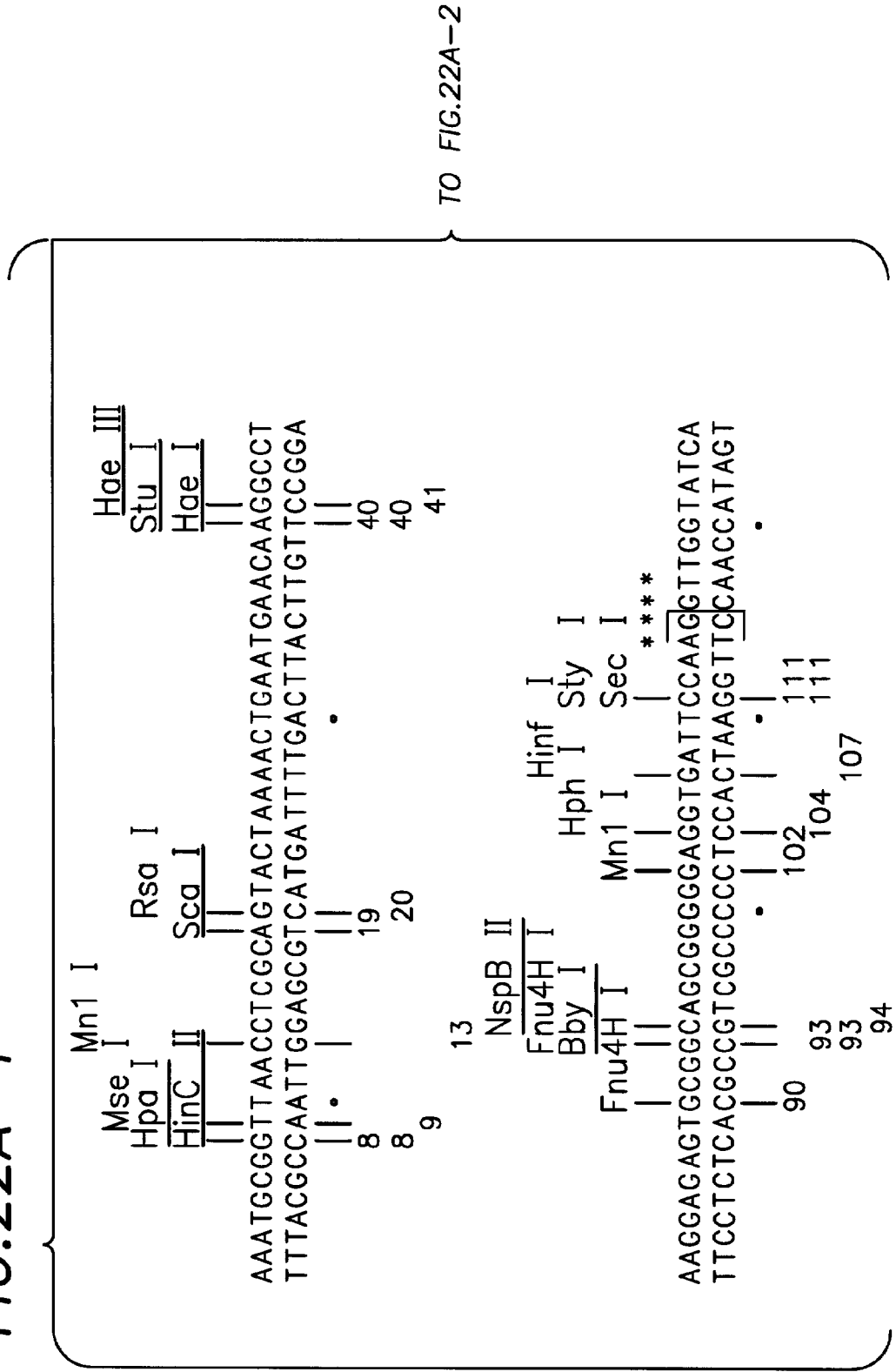
Figures 2, 22A:

The product of the Taq amplification is shown in FIG. 20, and was ligated into the PCR 2.1 vector (Invitrogen, Carlsbad, Calif.) using the TA Cloning Kit according to manufacturer's instructions. Sequence analysis (using standard dideoxy sequencing methods, and Universal and Reverse primers from United States Biochemical, Cleveland, Ohio) of multiple (9) clones confirmed that all ligation junctions were correct (see FIGS. 21 and 22).

Because this strategy ligated product molecules with rubonucleotide overhangs, it is sometimes referred to as Ribonucleotide overhang cloning (ROC).

Example 2

Preparation and Ligation of Product Molecules with 3' Overhang Sequences

This Example describes the preparation and ligation of product molecules having 3' overhangs, using hybrid primers containing deoxyribonucleotides at their 3' ends and ribonucleotides at their 5' ends.

Figure 28:
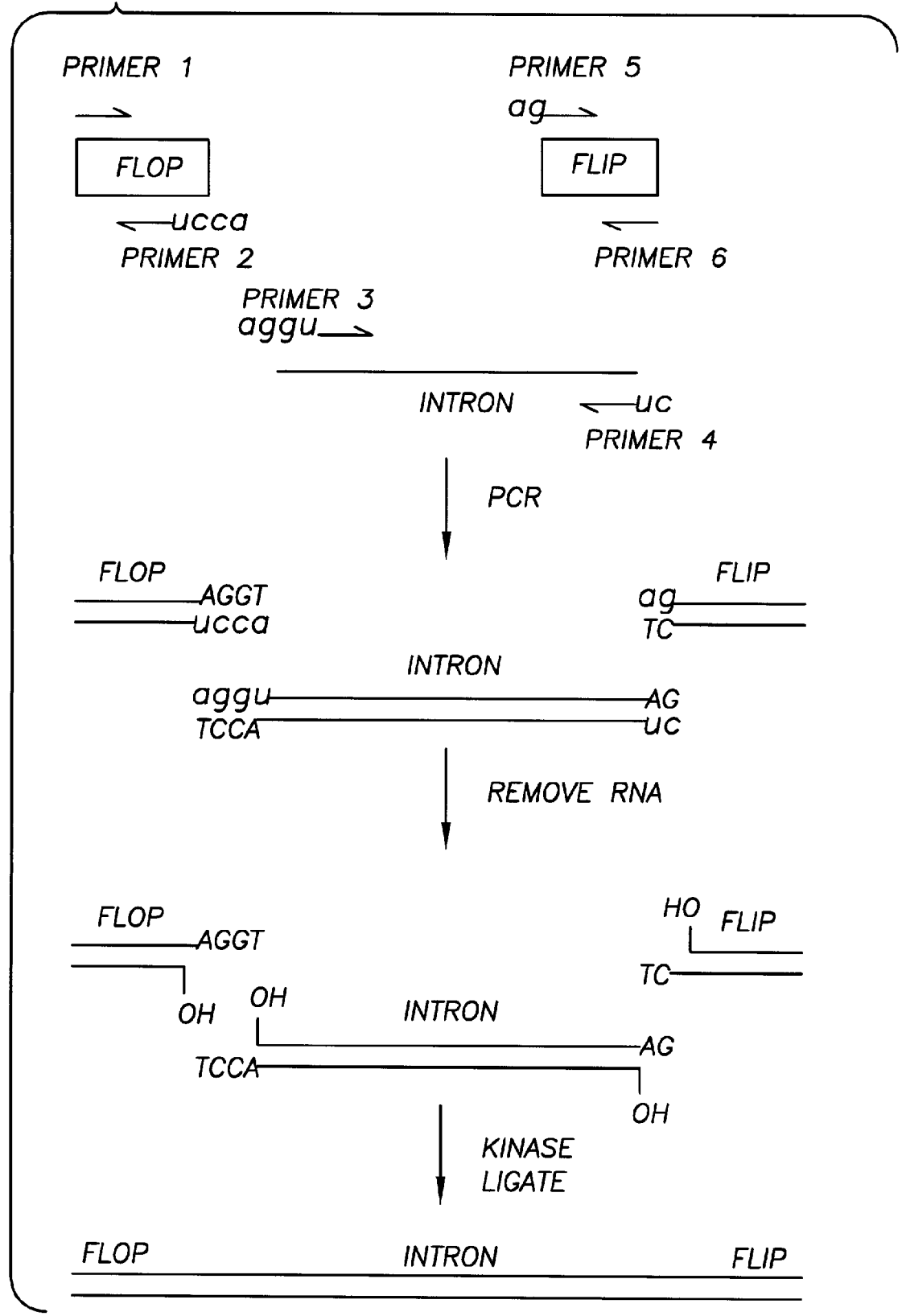
FIG. 28 depicts a schematic representation of a directional ligation reaction employing inventive product molecules containing 3' overhangs.

FIG. 28 presents a schematic of the particular experiment that was performed. As shown, three different product molecules were generated, two of which correspond to the Flip and Flop exons of the gene for subunit B of the human glutamate receptor, and one of which corresponds to an intron from the unrelated human β-globin gene (see Example 1).

Each of the three product molecules was prepared by PCR, using a Pfu polymerase which copies RNA nucleotides, and either human genomic DNA or HBT7 (see Example 1). The Flop exon was amplified with primers 1 and 2 from Example 1; intron 1 was amplified either with primers 3 and 4 from Example 1 or with primer 3 and an alternative primer 4 (5'uucuAAGGGTGGGAAAATAG-3'; SEQ ID NO 24); the Flip exon was amplified either with primers 5 and 6 or with an alternative primer 5 (5'agaaCCCAGTAAATCTTGC; SEQ ID NO 25); and primer 6.

Each 100 μL reaction contained 2.5 U of Pfu Turbo® polymerase (Stratagene), 1× Cloned Pfu buffer (10 mM (NH$_4$)$_2$SO$_4$, 20 mM Tris pH=8.8, 2 mM Mg SO$_4$, 10 mM KCl, 0.1% Triton X-100 and 0.1 mg/ml BSA), 200 μM of each dNTP, 1 mM MgSO$_4$, and primers at a final concentration of 0.5 μM each. The Flop and Flip reactions contained 375 ng of human genomic DNA, while the β-globin reaction contained 5 ng of HBT7 DNA. The PCR step program was one cycle of 95° C., 5 min; 50° C., 3 min; 72° C. 3 min; followed by 40 cycles of 95° C., 30 sec; 50° C., 30 sec; 72° C., 45 sec; followed by one cycle of 72° C., 5 min in Robocycler gradient 40 for the Flip and Flop fragments. The same program was used to amplify β-globin intron 1, except the annealing temperature was 46° C. Since Pfu polymerase does not copy RNA (stratagene product literature), the PCR products contained 5' overhangs. These overhangs were filled in during an incubation at 72° C. for 30 minutes with 5 U of Tth polymerase (Epicentre Technolgies, Madison, Wis.), to fill in the 5'-RNA overhangs (Note, in more recent experiments, M-MLV RT was used, rather than Tth, to fill in the overhangs. When M-MLV RT was used, the fragments were separated on agarose gels prior to treatment with 200 U of M-MLV RT in 1× First strand buffer (50 mM Tris pH=8.3, 75 mM KCl, 3 mM MgCl$_2$), 10 mM DTT and 0.5 mM dNTP in 20 μL.). This strategy allowed us to use Pfu polymerase, which has the highest fidelity of available thermostable DNA polymerases, during the amplification reaction but still generate blunt-ended reaction products.

The amplified parental PCR products were excised from an agarose gel and purified. Five μl of each purified sample were fractionated on an agarose gel for quantitation. We then converted the blunt-ended products to products containing 3' overhangs by removing the ribonucleotides through exposure to mild base. NaOH (1 N) was added to 8 μl of each of the gel isolated fragments to a final concentration of 0.2 N and the samples were incubated at 45° C. for 30 min. The base was neutralized by addition of 2 μl of 1 N HCl. Since NaOH hydrolysis generates a 3'-phosphate and a 5'-OH, we had to phoshoylate the products to be able to ligate them. The DNA fragments were phosphorylated in 1×T4 ligase buffer (USB) in a total of 20 μl for 30 min at 37° C. using 10 U of PNK (USB). Approximately 25 ng (3-6 μl) of each phosphorylated product were combined in a final volume of 20 μl and ligated for 16 hours at 14 μC in 1×T4 ligase buffer with 5 Weiss U of T4 DNA ligase (USB).

To produce the chimeric Flop-β-Flip product, a secondary PCR amplication was performed as described above for the primary PCRs using 1 μl of ligation reaction as template, primers 1 and 6, and an annealing temperature of 58° C. A chimeric product of the expected size (360 bp) was observed. This product was cloned and sequenced; both ligation junctions were correct in 6 of 8 clones that were sequenced. Two clones each had an error at one of the ligation sites. In one clone, three base pairs were lost at the boundary between the β-globin intron and Flip. In the other clone, an A was changed to a T (data not shown). We suspect that Tth polymerase introduced these errors during the fill in step of the procedure. Because the strategy described here involved ligation of molecules containing DNA overhangs, it is sometimes referred to as DNA Overhang Cloning (DOC).

Example 3

Bioassays for Determining Success of Primer Copying and/or Ligation

The present Example describes techniques that could be used to evaluate the ability of a particular DNA polymerase to copy (i.e., to use as a template) a particular modified oligonucleotide primer. For example, the techniques described herein might be useful to determine whether a particular modified nucleotide or ribonucleotide (or collection thereof) can be replicated by one or more DNA polymerases.

Figure 29:
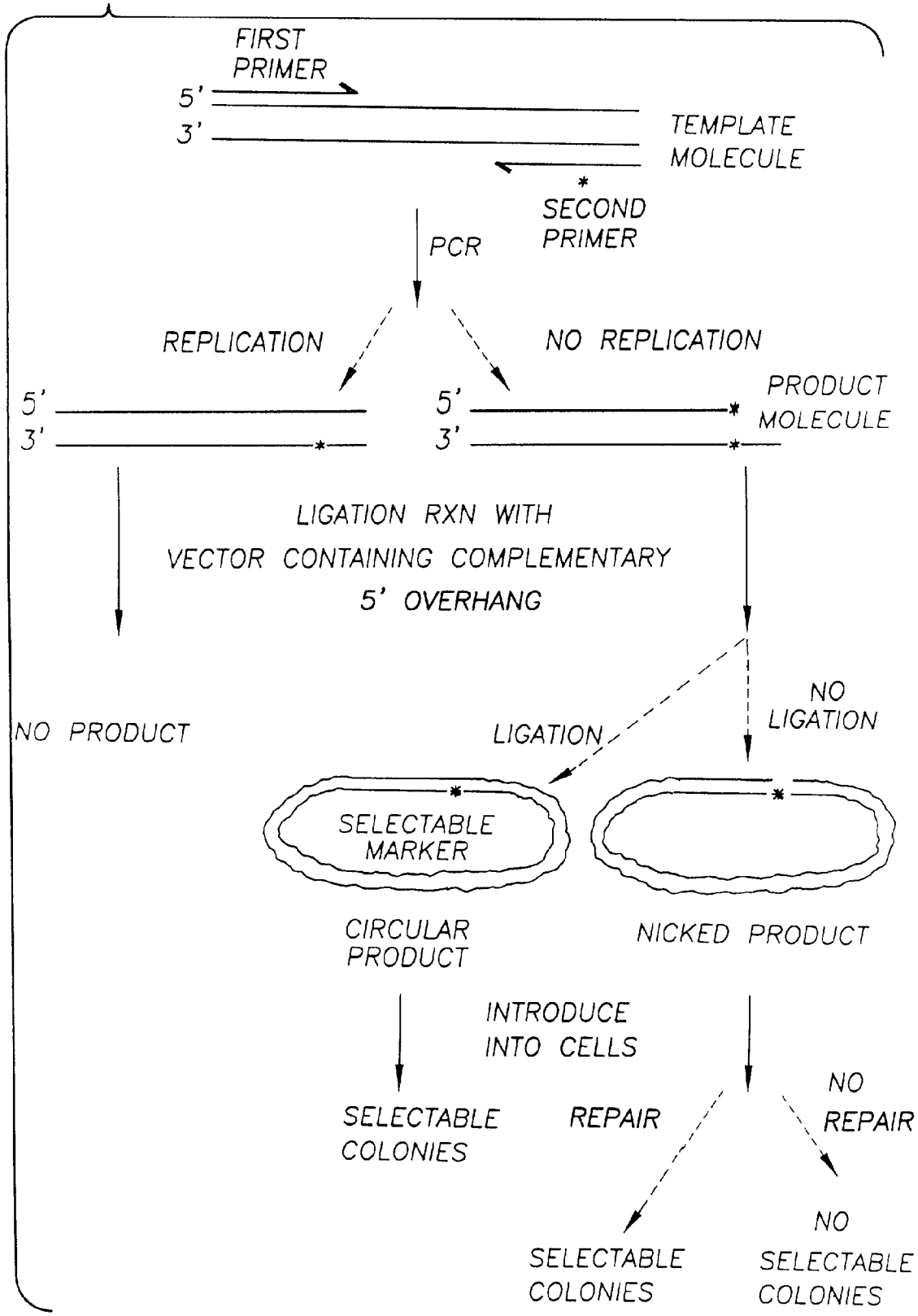
FIG. 29 presents a schematic of certain bioassay techniques that can be employed to determine the success of primer copying and/or ligation in inventive reactions.

FIG. 29 presents one embodiment of the present bioassay techniques. As shown, two primers are provided that hybridize with a template molecule. The first primer is known to be extendible by a particular DNA polymerase; the second primer includes one or more modified nucleotides or ribonucleotides whose ability to block replication by the DNA polymerase is unknown. Any nucleotide modification may be studied in the system.

As shown in FIG. 29, both primers are extended, so that, if replication is blocked, a product molecule with a 5' overhang is produced; a blunt-ended product molecule (or a molecule containing a single-nucleotide 3'-overhang, depending on the DNA polymerase employed) is generated if replication is not blocked.

The product molecule is then incubated with a vector containing a complementary 5' overhang and carrying a selectable marker (or a marker identifiable by screening). Only if replication was blocked will hybridization occur. Ligation is then attempted and should succeed unless the particular modification interferes with ligation of a nick on the complementary strand (unlikely) or the modification is present at the 5' end of the overhang and is of a character that interferes with ligation to an adjacent 3' end. In order to simplify the experiment and minimize the number of variables in any particular reaction, it is expected that modifications will only be incorporated at the very 5' end of a primer if their ability to block replication is already known and the desire is to asses only their ability to interfere with ligation.

The ligation product is then introduced into host cells, preferably bacteria. Selectable (or otherwise identifiable) cells will grow and proliferate only if the modification in question did block replication and either (i) did not block ligation on the complementary strand; or (ii) did block ligation on the complementary strand but did not block in vivo nick repair. If the modification were at the 5' end of the primer, cells will only grow if the modification did block replication and did not block ligation of both strands.

Of course, where the modification constitutes one or more ribonucleotides, or other removable nucleotides, absence of colonies due to inability to block replication can be distinguished from other absence of colony results by treating the original product molecule with an agent that will remove the modified nucleotide(s), along with any more 5' nucleotides, and then incubating the resulting secondary product molecule, which contains a 3' overhang complementary to the modified nucleotide and any more 5' nucleotides, with a vector containing a compatible 3' overhang.

Example 4

Directional Ligation of Multiple Nucleic Acid Molecules by Engineered Selective Compatibility of Catalytic Ribozyme Elements FIG. 30 shows a directional ligation reaction that allowed selective ligation of particular exons through use of incompatible ribozyme components. As indicated, transcripts were generated in which (i) a first exon (A) was linked to a first ribozyme component from the aI5γ group II intron; (ii) a second exon (B) was flanked by (a) a second ribozyme component, also from the aI5γ group II intron, that is compatible with the first ribozyme component, and (b) a third ribozyme component, from the LTRB intron of *Lactococus lacti*, that is not compatible with the second intron component; and (iii) a third exon was linked to a fourth ribozyme component, also from the LTRB intron, that is compatible with the third intron component but not with the first intron component. These three transcripts were incubated together under splicing conditions and, as shown, only the ABC product (and not the AC nor the circular B product) was produced.

In all, nine plasmids were used in the study: pJD20, pB.E5.D4, pD4.E3(dC).B(2), pLE12, pB.5'Lac, p3'Lac.B, pD4.E3(dC)B(2).5'Lac, and p3'Lac.B.E5.D4. Two PCR amplifications were performed using plasmid pJD20, which contains the full-length aI5γ intron (Jarrell et al., *Mol. Cell. Biol.* 8:2361, 1988), as a template. The first reaction amplified part of the intron (domains 1-3 and 73 nt of domain 4), along with part (27 nt) of the 5' exon. The primers utilized, BamHI.E5 (5'-ACGGGATCCATACTTACTACGTGGTGGGAC; SEQ ID NO 7) and D4.SalI (5'-ACGGTCGACCCTC-CTATCTTTTTTAATTTTTTTTT; SEQ ID NO 8), were designed so that the PCR product had unique BamHI and SalI sites at its ends. The PCR product was digested with BamHI and SalI, and was ligated into the PBS-vector (Stratagene), digested with the same enzymes, so that it was positioned downstream of the T7 promoter. The resulting plasmid was designated pB.E5.D4, and encodes the B.5'γ shuffling cassette (see FIG. 31).

The second PCR reaction that utilized pJD20 as a template amplified a different part of the intron (the remaining 65 nt of domain 4 plus domains 5-6), along with part (29 nt) of the 3' exon. The primers utilized, KpnI.D4 (5'-ACGGGTACCTT-TATATATAACTGATAAATATTTATT; SEQ ID NO 9) and E3.BamHI (5'-ACGGGATCCAGAAAATAGCACCCAT-TGATAA; SEQ ID NO 10), were designed so that the PCR product had unique KpnI and BamHI sites at its ends. The PCR product was digested with KpnI and BamHI, and was ligated into the PBS-vector, digested with the same enzymes, so that it was positioned downstream of the T7 promoter. The resulting plasmid was called pD4.E3(dC).B (see FIG. 31).

Sequence analysis of the pD4.E3(dC).B plasmid revealed an unexpected point mutation in the 3' exon sequence. The expected sequence was ACTATGTATTATCAATGGGTGC-TATTTTCT (SEQ ID NO 11); the observed sequence was ACTATGTATTATAATGGGTGCTATTTTCT (SEQ ID NO 12).

A site directed mutagenesis reaction was then performed, using the QuickChange® Site-Directed Mutagenesis Kit (Stratagene, catalog number 200518) to insert an additional BamHI site into the 3' exon sequence. The primers utilized were designated E3.BamHI(2) (5'-CTCTAGAGGATCCA-GAAAATAGGATCCATTATAATACATAGTATCCCG; SEQ ID NO 13) and E3.BamHI(2)complement (5'-CGG-GATACTATGTATTATAATGGATC-CTATTTTCTGGATCCTCTAGAG; SEQ ID NO 14). The plasmid generated as a result of the site-directed mutagenesis reaction was designated pD4.E3.(dC).B(2), and encoded the 3'γ.B shuffling cassette (see FIG. 31), in which the length of the 3' exon was shortened to 13 nt.

Two additional PCR reactions were performed, in which the plasmid pLE12, which encodes the full-length LTRB intron flanked by its natural 5' and 3' exons (Mills et al., *J. Bacteriol.* 178:3531, 1996), was used as a template. In the first reaction, primers 5'transM.E.5' (5'-CACGGGATC-CGAACACATCCATAACGTGC; SEQ ID NO 15) and 5'sht3' (5'-CAGCGTCGACGTACCCCTTTGCCATGT; SEQ ID NO 16) were used to amplify part of the LTRB intron (domains 1-3), and part (15 nt) of the 5' exon. The PCR product was generated with Taq polymerase and was cloned into the PCR2.1 Topo vector (Invitrogen) using the Topo® TA Cloning® kit (Invitrogen). The resulting plasmid was designated pB.5'Lac, and encodes the B.5'Lac shuffling cassette (see FIG. 31).

Figure 31:
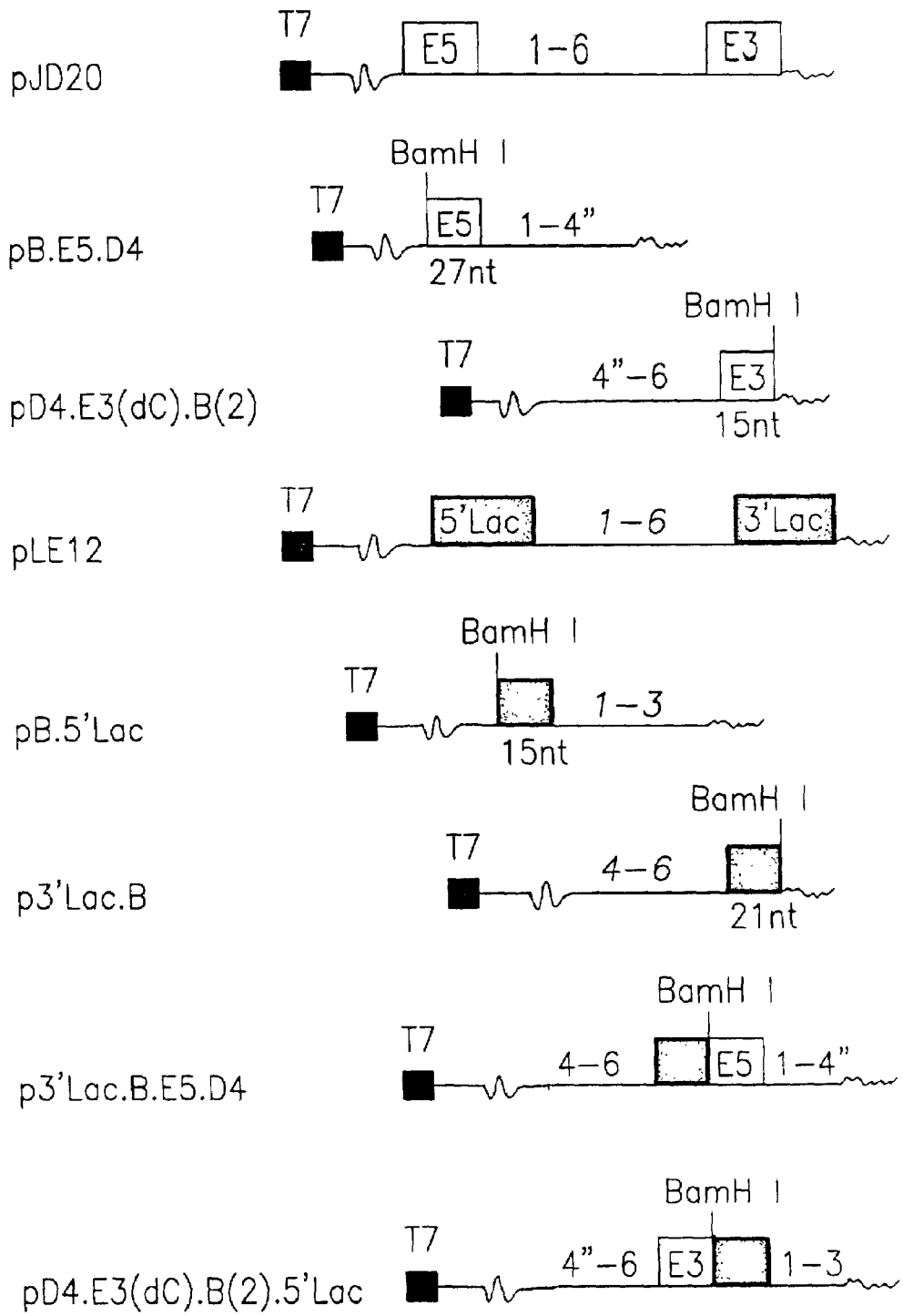
FIG. 31 shows constructs employed in the reaction of FIG. 30.

The same PCR product was also digested with BamHI and SalI, and was ligated into pD4.E3(dC).B(2), cut with the same enzymes, to produce pD4.E3(dC)B(2).5'Lac, which encodes the 3'γ.B.5'Lac shuffling cassette (see FIG. 31).

Additionally, plasmid pB.5'Lac was digested with SpeI and Asp718 to remove some unwanted restriction sites. Overhangs were filled in with Klenow fragment, and the resulting blunt ends were ligated to reseal the vector. The plasmid thereby produced was designated pB.5'Lac(K) (see FIG. 31).

The second PCR reaction that utilized pLE12 as a template involved the use of primers 3'transM.E.5' (5'-CACG-GAGCTCTTATTGTGTACTAAAAT-TAAAAATTGATTAGGG; SEQ ID NO 17) and 3'transM.E.3' (5'-CAGCGGATCCCGTAGAATTAAAAAT-GATATGGTGAAGTAG; SEQ ID NO 18) to amplify part of the PTRB intron (domains 4-6), attached to part (21 nt) of the 3' exon. The primers were designed so that the PCR product had unique SacI and BamHI sites at its ends. The PCR products was generated with Taq polymerase and was cloned into the pCR2.1 Topo vector. The resulting plasmid was designated 3'Lac.B, and encoded the 3'Lac.B shuffling cassette (see FIG. 31).

Plasmid p3'Lac.B was digested with SacI and BamHI, and the 1993 bp band thereby generated was purified from an agarose gel using the Geneclean II kit (BIO 101). The purified fragment was then ligated into pE5.D4, digested with the same enzymes, to produce plasmid p3'Lac.B.E5.D4, encoding the 3'Lac.B.5'γ shuffling cassette (see FIG. 31).

Plasmids pB.E5.D4, pD4.E3(dC).B(2), pB.5'Lac, p3'Lac, B, and pD4.E3(dC)B(2).5'Lac were linearized with HindIII and were transcribed in vitro with T7 RNA polymerase (Stratagene, catalog number 600123) at 40° C. for 1 hour in 100 μL reactions containing 6 μg of linearized template DNA and 0.5 mM unlabeled ATP, CTP, GTP, and UTP. The RNAs produced in these transcription reactions were treated with 1 U of RQ1 RNase-free DNase, were extracted with phenol-chloroform, were desalted on a Sephadex G25 column, and were precipitated with EtOH. Precipitates were subsequently resuspended in 6 μL water.

One μL of each resuspended RNA transcript was then used in a trans-splicing reaction carried out at 45° C. for 60 minutes, in 40 mM Tris-HCl, pH 7.6, 100 mM $MgCl_2$, and either 0.5 M $NH_4Cl$ or 0.5M $(NH_4)_2SO_4$.

Figure 32:
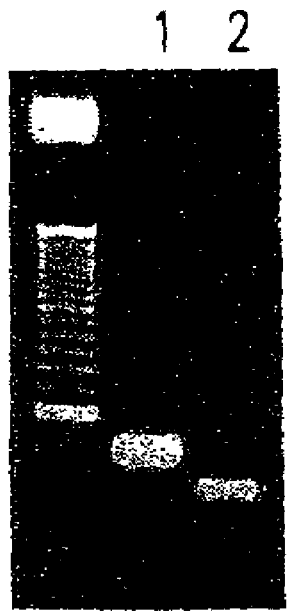
FIGS. 32 and 33 show products of the reaction of FIG. 30.
Figure 33:
Figure 34:
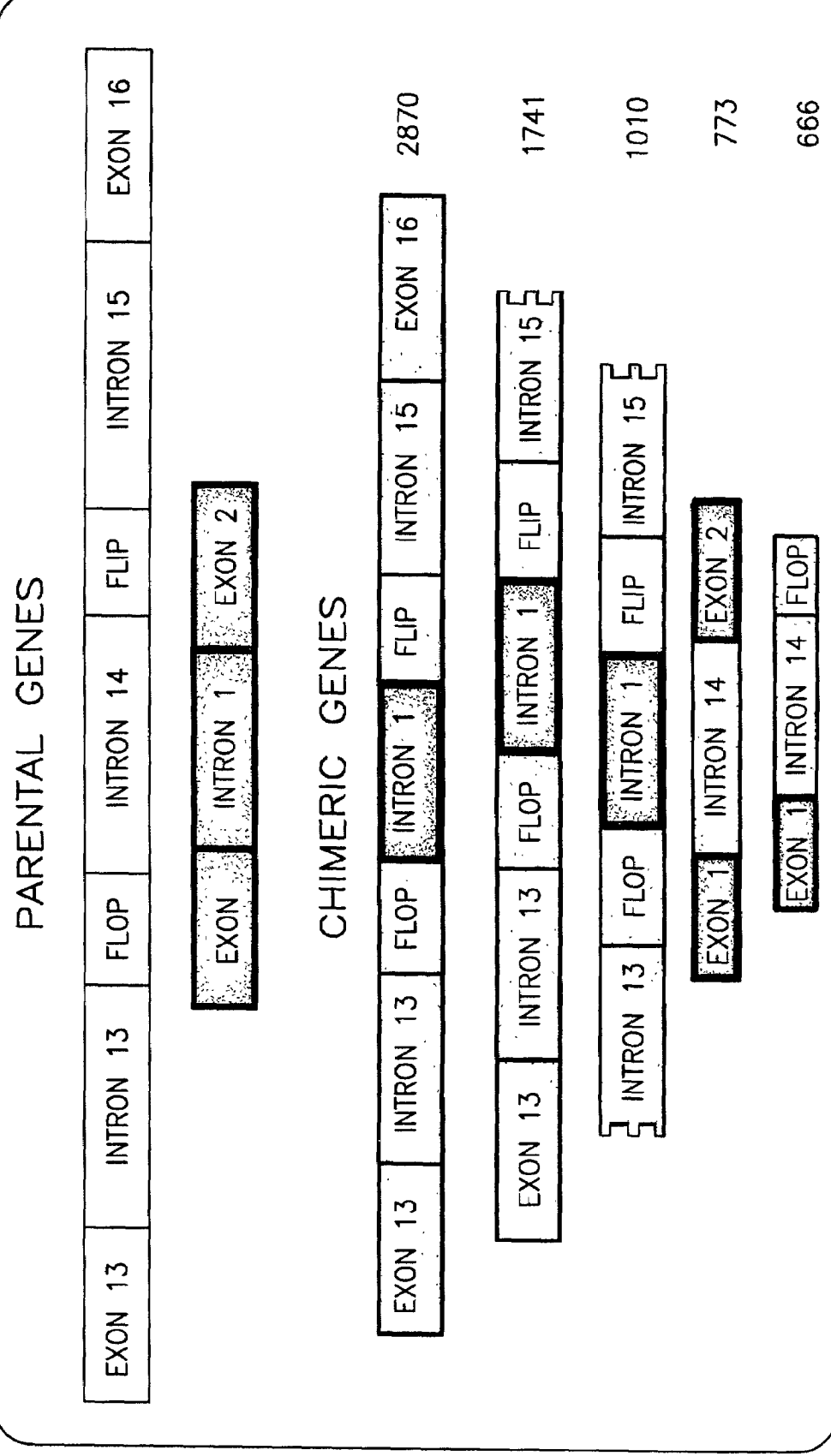
FIG. 34 shows a variety of chimeras generated using DNA-Overhang Cloning ("DOC"). The parental genes qare shown in lines 1 and 2. The five chimeric genes are shown below the parental genes. Jagged edges indicate that only a portion of introns 13 and 15 were amplified. Lengths of chimeric genes (in basepairs) are indicated.

After the trans-splicing reaction, a reverse transcription/PCR reaction was performed to identify ligated splicing products. The detected products were: (i) ligated alγ5 exons E5 and E3 produced by trans-splicing of B.E5.D4 and D4.E3 (dC).B(2) (lane 1, FIG. 32); (ii) ligated LTRB 5' and 3' exons produced by trans-splicing of 3'Lac.B and 3'Lac.B (lane 2, FIG. 33); and (iii) the three-molecule ligation product produced by trans-splicing of B.E5.D4, D4.E3(dC).B(2).5'Lac, and 3'Lac.B (lanes 2 and 3, FIG. 33).

Example 5

Cloning Products of 3'-overhang Product Ligation without Amplification of Chimeric Product We found that the products of a DOC ligation reaction could be cloned directly into a vector for replication in bacteria without a chimeric amplification step. As was described above in Example 2, we designed chimeric primers that, when used in a DOC experiment, generated Flop, intron 1, and Flip PCR products that could be ligated directionally. In addition, the primers were designed such that NaOH treatment of the PCR products creates an upstream overhang on the Flop exon that is compatible with an Apa I overhang, and a downstream overhang on the Flip exon that is compatible with a Pst I overhang. All three fragments were incubated together in the presence of ligase and pBluescript II SK (−) that had been digested with ApaI and PstI. An aliquot of the ligation mixture was transformed directly into *E. coli*, and the expected chimeric clone was readily isolated, sequenced, and found to be perfect (data not shown).

Example 7

Construction of Multiple Chimeric Products by DNA-Overhang Cloning

To demonstrate the generality of the procedures described herein, we applied the techniques of Example 2 and to a variety of different molecules and produced five different chimeras, shown in FIG. 35. All five chimeras were generated by directional three-molecule ligation. Note that these chimeras were generated using M-MLV reverse transcriptase, rather than Tth, to fill in 5' RNA overhangs. When M-MLV RT was used, no errors were detected at any of the ligation points.

OTHER EMBODIMENTS

Those of ordinary skill in the art will appreciate that the foregoing has been a description merely of certain preferred embodiments of the present invention; this description is not intended to limit the scope of the invention, which is defined with reference to the following claims:

We claim:

1. A method of generating a nucleic acid molecule, the method comprising steps of:

providing a first precursor nucleic acid molecule including a first double stranded portion flanked by first and second single-stranded overhangs;

providing a second precursor nucleic acid molecule including a second double-stranded portion flanked by third and fourth single-stranded overhangs, the third single-stranded overhang being complementary with the second overhang of the first precursor nucleic acid molecule;

providing a third precursor nucleic acid molecule including a third double-stranded portion flanked by fifth and sixth single-stranded overhangs, the fifth overhang being complementary with the fourth overhang of the second precursor nucleic acid molecule and the sixth overhang being complementary with the first overhang of the first nucleic acid molecule; and combining the first, second, and third precursor nucleic acid molecules together in a single reaction under conditions that allow for hybridization of the complementary overhangs, so that a new nucleic acid molecule is generated;

wherein at least one of the precursor nucleic acid molecules is generated by extending first and second primers in a polymerase-mediated extension reaction, at least one of the first and second primers including at least one base-containing residue, which base-containing residue is not used as a template by the polymerase employed in the polymerase-mediated extension reaction, but which is capable of being used as a template by a different polymerase.

2. The method of claim 1, further comprising a step of:
ligating the hybridized precursor nucleic acid molecules together.

3. The method of claim 2, wherein the step of ligating comprises ligating in vitro.

4. The method of claim 2, wherein the step of ligating comprises ligating in vivo.

5. The method of claim 1, wherein at least one of the steps of providing a precursor nucleic acid molecule comprises:
extending first and second primers in a polymerase-mediated extension reaction, at least one of the primers including at least one residue that renders the primer susceptible to cleavage under conditions in which DNA is not normally susceptible to cleavage.

6. A method of generating a protein coding gene, the method comprising steps of:
providing a plurality of first precursor nucleic acid molecules, each first precursor nucleic acid molecule including a first double stranded portion flanked by at least a one first single-stranded overhang and having a nucleotide sequence that encodes a first open reading frame;
providing a plurality of second precursor nucleic acid molecules, each of which includes a second double-stranded portion flanked by at least one second single-stranded overhang, at least part of which is complementary to at least part of the first single-stranded overhang, wherein each such second precursor nucleic acid molecule has a nucleotide sequence that encodes a second open reading frame;
admixing the first and second pluralities of nucleic acid molecules together under conditions that allow for hybridization of the complementary overhangs, so that a plurality of new nucleic acid molecules is generated, wherein each such generated new nucleic acid molecule has a nucleotide sequence that encodes a third open reading frame comprising both of the first and second open reading frames
wherein at least one of the precursor nucleic acid molecules in at least one of the provided pluralities is generated by extending first and second primers in a polymerase-mediated extension reaction, at least one of the first and second primers including at least one base-containing residue, which base-containing residue is not used as a template by the polymerase employed in the polymerase-mediated extension reaction, but which is capable of being used as a template by a different polymerase.

7. The method of claim 6 wherein the second double-stranded portion of each of the second precursor nucleic acid molecules is identical, and wherein at least two second precursor nucleic acid molecules differ from each other at one or more positions in the second single-stranded portion.

8. The method of claim 6, wherein the second single-stranded portion of each of the second precursor nucleic acid molecules is identical, and wherein the second double-stranded portions of each of the second precursor nucleic acid molecules differ from one another.

9. The method of claim 8, wherein the open reading frames encoded by the second double-stranded portions each encode a functional domain of a protein.

10. The method of claim 9, wherein the open reading frames encoded by the second double-stranded portions each encode a different version of the same functional domain.

11. The method of claim 9, wherein the second double-stranded portions of each of the second precursor nucleic acid molecules are substantially similar, but non-identical to one another.

12. The method of claim 9 or 11, wherein the second double-stranded portions of each of the second precursor nucleic acid molecules are identical lengths.

13. The method of claim 6, further comprising a step of ligating the hybridized precursor nucleic acid molecules together.

14. The method of claim 13, wherein the step of ligating comprises ligating in vitro.

15. The method of claim 13, wherein the step of ligating comprises ligating in vivo.

16. The method of claim 6 wherein the third open reading frame encodes at least part of a protein selected from the group consisting of: animal fatty acid synthases, polyketide synthases, peptide synthetases and terpene synthases.

17. The method of claim 6, further comprising the step of providing a plurality of third precursor nucleic acid molecules, each third precursor nucleic acid molecule including a third double-stranded portion flanked by at least a third single-stranded overhang, wherein each such third precursor nucleic acid molecule has a nucleotide sequence that encodes a third open reading frame, and wherein the third single-stranded overhang is complementary to either the first single-stranded overhang or the second single-stranded overhang.

18. The method of claim 17, wherein the first, second and third pluralities of precursor nucleic acid molecules are admixed simultaneously.

19. The method of claim 17, wherein the first, second and third pluralities of precursor nucleic acid molecules are admixed sequentially.

20. A method of generating a protein coding gene, the method comprising steps of:
providing at least two collections of precursor nucleic acid molecules, wherein each of said collections comprises at least two nucleic acid molecules that each contain a nucleotide sequence that encodes an open reading frame;
selecting an individual nucleic acid molecule, or portion of a nucleic acid molecule, from each of said collections; and
admixing the selected nucleic acid molecules or portions together under conditions that allow for hybridization of the complementary overhangs, so that a new nucleic acid molecules is generated that contains a nucleotide sequence that encodes an open reading frame comprising the open reading frames of each of the selected nucleic acid molecules
wherein at least one of the selected nucleic acid molecules is generated by extending first and second primers in a polymerase-mediated extension reaction, at least one of the first and second primers including at least one base-containing residue, which base-containing residue is not used as a template by the polymerase employed in the polymerase-mediated extension reaction, but which is capable of being used as a template by a different polymerase.

21. The method of claim 20, wherein the open reading frames encoded by the nucleic acid molecules of one of the collections encode a functional domain of a protein.

22. The method of claim 21, wherein the open reading frames encoded by the nucleic acid molecules of one of the collections encode a different version of the same functional domain.

23. The method of claim 21, wherein the open reading frames encoded by the nucleic acid molecules of one of the collections are substantially similar, but non-identical to one another.

24. The method of claim 21 or 23, wherein the open reading frames encoded by the nucleic acid molecules of one of the collections are identical lengths.

25. The method of claim 20, further comprising a step of ligating the hybridized precursor nucleic acid molecules together.

26. The method of claim 25, wherein the step of ligating comprises ligating in vitro.

27. The method of claim 25, wherein the step of ligating comprises ligating in vivo.

28. The method of claim 20 wherein the new nucleic acid molecule generated comprises an open reading frame encoding a protein selected from the group consisting of: animal fatty acid synthases, polyketide synthases, peptide synthetases and terpene synthases.

29. The method of claim 20, wherein the selected nucleic acid molecules or portions are admixed simultaneously.

30. The method of claim 20, wherein the selected nucleic acid molecules or portions are admixed sequentially.

31. A method of generating a protein coding gene, the method comprising steps of:
providing a first plurality of first precursor nucleic acid molecules, each first precursor nucleic acid molecule including a first double stranded portion flanked by at least a first single-stranded overhang and having a nucleotide sequence that encodes a first open reading frame;
providing a second precursor nucleic acid molecule that includes a second double stranded portion flanked by at least a second single-stranded overhang, the second single-stranded overhang being complementary to the first single-stranded overhang of the plurality of precursor nucleic acid molecules wherein the second precursor nucleic acid molecule has a nucleotide sequence that encodes a second open reading frame;
admixing the plurality of nucleic acid molecules and the second nucleic acid molecule together in a single reaction under conditions that allow for hybridization of the complementary overhangs, so that a plurality of new nucleic acid molecules is generated wherein each such generated new nucleic acid molecule has a nucleotide sequence that encodes a third open reading frame comprising both of the first and second open reading frames
wherein at least one of the first precursor nucleic acid molecules in the first plurality or the second precursor nucleic acid molecule is generated by extending first and second primers in a polymerase-mediated extension reaction, at least one of the first and second primers including at least one base-containing residue, which base-containing residue is not used as a template by the polymerase employed in the polymerase-mediated extension reaction, but which is capable of being used as a template by a different polymerase.

32. The method of claim 31 wherein the first double-stranded portion of each of the first precursor nucleic acid molecules is identical, and wherein at least two second precursor nucleic acid molecules differ from each other at one or more positions in the second single-stranded portion.

33. The method of claim 31, wherein the first single-stranded portion of each of the second precursor nucleic acid molecules is identical, and wherein the first double-stranded portions of each of the second precursor nucleic acid molecules differ from one another.

34. The method of claim 33, wherein the open reading frames encoded by the first double-stranded portions each encode a functional domain of a protein.

35. The method of claim 34, wherein the open reading frames encoded by the first double-stranded portions each encode a different version of the same functional domain.

36. The method of claim 34, wherein the first double-stranded portions of each of the first precursor nucleic acid molecules are substantially similar, but non-identical to one another.

37. The method of claim 34 or 36, wherein the first double-stranded portions of each of the first precursor nucleic acid molecules are identical lengths.

38. The method of claim 31, further comprising a step of ligating the hybridized precursor nucleic acid molecules together.

39. The method of claim 38, wherein the step of ligating comprises ligating in vitro.

40. The method of claim 38, wherein the step of ligating comprises ligating in vivo.

41. The method of claim 31 wherein the new nucleic acid molecules generated comprise open reading frames encoding proteins selected from the group consisting of: animal fatty acid synthases, polyketide synthases, peptide synthetases and terpene synthases.

42. The method of claim 31, further comprising the step of providing a plurality of third precursor nucleic acid molecules, each third precursor nucleic acid molecule including a third double-stranded portion flanked by at least a third single-stranded overhang, wherein each such third precursor nucleic acid molecule has a nucleotide sequence that encodes a third open reading frame, and wherein the third single-stranded overhang is complementary to either the first single-stranded overhang or the second single-stranded overhang.

43. The method of claim 42, wherein the first and third pluralities of precursor nucleic acid molecules and the second precursor nucleic acid molecules are admixed simultaneously.

44. The method of claim 42, wherein the first and third pluralities of precursor nucleic acid molecules and the second precursor nucleic acid molecules are admixed sequentially.

45. The method of claim 31, further comprising the step of providing a third precursor nucleic acid molecule that includes a third double-stranded portion flanked by at least a third single-stranded overhang, wherein the third precursor nucleic acid molecule has a nucleotide sequence that encodes a third open reading frame, and wherein the third single-stranded overhang is complementary to either the first single-stranded overhang or the second single-stranded overhang.

46. The method of claim 45, wherein the first plurality of precursor nucleic acid molecules and the second and third precursor nucleic acid molecules are admixed simultaneously.

47. The method of claim 45, wherein the first plurality of precursor nucleic acid molecules and the second and third precursor nucleic acid molecules are admixed sequentially.

* * * * *